US008883079B2

(12) United States Patent
Clark

(10) Patent No.: US 8,883,079 B2
(45) Date of Patent: Nov. 11, 2014

(54) AQUATIC ENVIRONMENT WATER-QUALITY MONITOR HAVING A SUBMERSIBLE CHEMICAL INDICATOR WHEEL

(71) Applicant: Step Ahead Innovations, Inc., Williston, VT (US)

(72) Inventor: James E. Clark, South Burlington, VT (US)

(73) Assignee: Step Ahead Innovations, Inc., South Burlington, VT (US)

( * ) Notice: Subject to any disclaimer, the term of this patent is extended or adjusted under 35 U.S.C. 154(b) by 0 days.

(21) Appl. No.: 13/713,537

(22) Filed: Dec. 13, 2012

(65) Prior Publication Data

US 2014/0017143 A1 Jan. 16, 2014

Related U.S. Application Data

(63) Continuation of application No. PCT/US2012/069209, filed on Dec. 12, 2012.

(60) Provisional application No. 61/630,450, filed on Dec. 12, 2011.

(51) Int. Cl.
*G01N 21/00* (2006.01)
*G01N 33/18* (2006.01)
(Continued)

(52) U.S. Cl.
CPC ........ *G01N 21/88* (2013.01); *G01N 2021/7793* (2013.01); *G01N 33/18* (2013.01);
(Continued)

(58) Field of Classification Search
CPC .......... G01N 2021/7793; G01N 21/64; G01N 21/78; B01L 3/502761; B01L 2200/0621; B01L 2200/0647; B01L 2200/0673; B01L 2200/10; B01L 2200/16; B01L 2300/0816; B01L 2300/0887; B01L 2300/123; B01L 2300/1805; B01L 2300/1822; B01L 2300/1883; B01L 2300/0803

USPC .......... 422/52, 68.1, 73, 82.01, 82.05, 82.06, 422/82.07, 82.08, 82.09, 82.11, 407, 501, 422/502, 503, 504, 507; 436/164, 177, 43, 436/63, 149, 172, 174, 518, 805, 809; 435/29, 4, 7.1
See application file for complete search history.

(56) References Cited

U.S. PATENT DOCUMENTS

| 4,205,043 A | 5/1980 | Esch et al. |
| 5,110,724 A | 5/1992 | Hewett |

(Continued)

FOREIGN PATENT DOCUMENTS

| EP | 1217373 A1 | 6/2002 |
| EP | 1225442 A2 | 7/2002 |

(Continued)

OTHER PUBLICATIONS

Photonic BioSystems. Oxygen Sensing Overview. http://www.photonicsystems.com/oxygen.html. Accessed on Jul. 12, 2012.
(Continued)

*Primary Examiner* — Dennis M White
(74) *Attorney, Agent, or Firm* — Birch, Tree IP Law & Strategy PLLC

(57) ABSTRACT

A water-quality monitoring system for an aquatic environment that includes a monitoring unit and a chemical indicator wheel designed and configured to be submerged in the water being monitored. The chemical indicator wheel includes a holder that supports a number of chemical indicators selected for use in measuring levels of constituents of the water. When in use, the wheel is drivingly engaged with a monitoring/measuring unit that includes at least one reader for reading the chemical indicators. In some embodiments, each apparatus includes a plurality of immobilized-dye-based chemical indicators that undergo an optically detectable physical change as levels of one or more constituents of the water change. Also disclosed are a variety of features that can be used to provide the monitoring system with additional functionalities.

24 Claims, 28 Drawing Sheets

(51) Int. Cl.

| | | |
|---|---|---|
| *G01N 31/22* | (2006.01) | |
| *G01N 21/85* | (2006.01) | |
| *G01N 21/88* | (2006.01) | |
| *G01N 21/78* | (2006.01) | |
| *C02F 1/00* | (2006.01) | |
| *G01N 21/15* | (2006.01) | |
| *F21V 8/00* | (2006.01) | |
| *G01N 21/77* | (2006.01) | |
| *G01N 21/64* | (2006.01) | |

(52) U.S. Cl.
CPC ........... *G01N 31/22* (2013.01); *G01N 21/8507* (2013.01); *G01N 21/78* (2013.01); *C02F 1/008* (2013.01); *G01N 21/15* (2013.01); *G02B 6/0001* (2013.01); *G01N 21/6428* (2013.01); *G01N 21/77* (2013.01); *Y10S 436/805* (2013.01); *Y10S 436/809* (2013.01)
USPC ........... 422/82.05; 422/52; 422/68.1; 422/73; 422/82.01; 422/82.06; 422/82.07; 422/82.08; 422/82.09; 422/82.11; 422/407; 422/501; 422/502; 422/503; 422/504; 422/507; 436/164; 436/177; 436/43; 436/63; 436/149; 436/172; 436/174; 436/518; 436/805; 436/809

(56) References Cited

U.S. PATENT DOCUMENTS

| | | | |
|---|---|---|---|
| 5,350,694 | A | 9/1994 | Zimmerle |
| 5,411,889 | A | 5/1995 | Hoots et al. |
| 5,547,578 | A | 8/1996 | Nielsen |
| 5,895,565 | A | 4/1999 | Steininger et al. |
| 5,902,749 | A | 5/1999 | Lichtwardt et al. |
| 5,952,491 | A | 9/1999 | Leiner et al. |
| 5,976,888 | A | 11/1999 | Lee et al. |
| 5,994,150 | A | 11/1999 | Challener et al. |
| 6,002,475 | A | 12/1999 | Boyd et al. |
| 6,051,437 | A | 4/2000 | Luo et al. |
| 6,124,135 | A | 9/2000 | Leiner et al. |
| 6,171,866 | B1 | 1/2001 | He et al. |
| 6,187,530 | B1 | 2/2001 | Scholin et al. |
| 6,211,359 | B1 | 4/2001 | He et al. |
| 6,342,349 | B1 * | 1/2002 | Virtanen ........................ 506/39 |
| 6,535,795 | B1 | 3/2003 | Schroeder et al. |
| 6,553,319 | B1 | 4/2003 | Hellfrich et al. |
| 6,599,748 | B1 | 7/2003 | Nakajima et al. |
| 6,653,152 | B2 | 11/2003 | Challener et al. |
| 6,657,546 | B2 | 12/2003 | Navarro et al. |
| 6,707,554 | B1 | 3/2004 | Miltner et al. |
| 6,794,191 | B2 | 9/2004 | Putnam et al. |
| 6,839,636 | B1 | 1/2005 | Sunshine et al. |
| 6,954,701 | B2 | 10/2005 | Wolfe |
| 7,014,612 | B2 | 3/2006 | Hubbard et al. |
| 7,040,157 | B2 | 5/2006 | Glasgow, Jr. et al. |
| 7,222,047 | B2 | 5/2007 | McMillan et al. |
| 7,242,001 | B1 | 7/2007 | Hedges et al. |
| 7,283,245 | B2 | 10/2007 | Xiao et al. |
| 7,360,402 | B2 | 4/2008 | Liao |
| 7,385,497 | B2 | 6/2008 | Golden |
| 7,390,399 | B2 | 6/2008 | Dennis, II et al. |
| 7,391,333 | B2 | 6/2008 | Madden et al. |
| 7,393,188 | B2 | 7/2008 | Lawyer et al. |
| 7,569,186 | B2 | 8/2009 | Bedingham et al. |
| 7,592,184 | B2 | 9/2009 | Khalil et al. |
| 7,720,615 | B2 | 5/2010 | Kim |
| 7,790,113 | B2 | 9/2010 | Putnam et al. |
| 7,858,383 | B2 | 12/2010 | He et al. |
| 7,905,245 | B2 | 3/2011 | McQuade et al. |
| 7,910,361 | B2 | 3/2011 | Barnes et al. |
| 7,960,181 | B2 | 6/2011 | He et al. |
| 8,038,937 | B2 | 10/2011 | Kelly et al. |
| 8,038,947 | B2 | 10/2011 | Thompson |
| 8,062,221 | B2 | 11/2011 | Debreczeny et al. |
| 8,065,023 | B2 | 11/2011 | Graves |
| 8,069,706 | B2 | 12/2011 | Battefeld et al. |
| 8,097,725 | B2 | 1/2012 | He et al. |
| 8,125,331 | B2 | 2/2012 | Allen et al. |
| 8,145,431 | B2 | 3/2012 | Kloepfer et al. |
| 8,158,259 | B2 | 4/2012 | Ramamurthy et al. |
| 8,173,438 | B1 | 5/2012 | Putnam et al. |
| 8,202,503 | B2 | 6/2012 | Putnam et al. |
| 8,237,920 | B2 | 8/2012 | Jones et al. |
| 8,455,844 | B2 | 6/2013 | Lear et al. |
| 8,510,064 | B2 | 8/2013 | Streppel et al. |
| 8,577,623 | B2 | 11/2013 | Wolfe |
| 8,586,911 | B2 | 11/2013 | Micinski et al. |
| 2001/0031503 | A1 | 10/2001 | Challener et al. |
| 2002/0054288 | A1 | 5/2002 | Kim et al. |
| 2002/0117430 | A1 | 8/2002 | Navarro et al. |
| 2004/0138840 | A1 | 7/2004 | Wolfe |
| 2004/0197922 | A1 * | 10/2004 | Cooper ........................... 436/52 |
| 2004/0224351 | A1 | 11/2004 | Shinohara |
| 2005/0180890 | A1 * | 8/2005 | Bedingham et al. ............ 422/99 |
| 2006/0222567 | A1 | 10/2006 | Kloepfer et al. |
| 2007/0074758 | A1 | 4/2007 | McQuade et al. |
| 2007/0078307 | A1 | 4/2007 | Debreczeny et al. |
| 2007/0233397 | A1 | 10/2007 | Kim |
| 2007/0251461 | A1 | 11/2007 | Reichard et al. |
| 2007/0259438 | A1 | 11/2007 | He et al. |
| 2008/0160502 | A1 * | 7/2008 | Barnes et al. ..................... 435/4 |
| 2008/0254544 | A1 | 10/2008 | Modzelewski et al. |
| 2009/0041621 | A1 | 2/2009 | Kelly et al. |
| 2009/0139456 | A1 | 6/2009 | Lin |
| 2009/0215183 | A1 | 8/2009 | Takehara et al. |
| 2010/0024526 | A1 | 2/2010 | Colvin, Jr. et al. |
| 2010/0052892 | A1 | 3/2010 | Allen et al. |
| 2010/0099193 | A1 | 4/2010 | Hsu et al. |
| 2010/0129852 | A1 | 5/2010 | Putnam et al. |
| 2010/0133175 | A1 | 6/2010 | Putnam et al. |
| 2010/0136608 | A1 | 6/2010 | Putnam et al. |
| 2010/0187185 | A1 | 7/2010 | Johnson et al. |
| 2010/0265509 | A1 | 10/2010 | Jones et al. |
| 2010/0330692 | A1 | 12/2010 | Khalil et al. |
| 2010/0332149 | A1 | 12/2010 | Scholpp |
| 2011/0168609 | A1 | 7/2011 | McQuade et al. |
| 2011/0218655 | A1 | 9/2011 | Graves |
| 2012/0183984 | A1 | 7/2012 | He et al. |
| 2013/0009781 | A1 | 1/2013 | Wolfe |
| 2013/0013259 | A1 | 1/2013 | Wolfe |
| 2013/0168327 | A1 | 7/2013 | Clark |
| 2014/0000507 | A1 | 1/2014 | Clark |
| 2014/0000651 | A1 | 1/2014 | Clark |
| 2014/0001126 | A1 | 1/2014 | Clark |
| 2014/0016122 | A1 | 1/2014 | Clark |
| 2014/0016344 | A1 | 1/2014 | Clark |
| 2014/0017143 | A1 | 1/2014 | Clark |
| 2014/0017796 | A1 | 1/2014 | Clark |
| 2014/0017801 | A1 | 1/2014 | Clark |
| 2014/0019060 | A1 | 1/2014 | Clark |
| 2014/0019069 | A1 | 1/2014 | Clark |

FOREIGN PATENT DOCUMENTS

| | | |
|---|---|---|
| EP | 1359409 A2 | 11/2003 |
| GB | 2480301 A | 11/2011 |
| GB | 2482155 A | 1/2012 |
| WO | 2007/115321 A2 | 10/2007 |
| WO | 2013/090407 A2 | 6/2013 |
| WO | PCT/US2012/069209 | 6/2013 |

OTHER PUBLICATIONS

Photonic BioSystems. Oxygen Sensing Features and Benefits. http://www.photonicsystems.com/O2features.html. Accessed on Jul. 12, 2012.

Photonic BioSystems. Oxygen Sensing Applications. http://www.photonicsystems.com/O2applications.html. Accessed on Jul. 12, 2012.

Sutron. DS5x Multiparameter Water Quality Sonde Datasheet. http://www.sutron.com/documents/ds5x-multiparameter-water-quality-sonde-datasheet.pdf. Accessed on Jul. 19, 2012.

(56) References Cited

OTHER PUBLICATIONS

Michael, Eric. EcoTech Marine Pump Patent Challenged: Request for Re-Examination Filed. GlassboxDesign.com. http://glassbox-design.com/2011/ecotech-marine-patent-reexam/. Sep. 4, 2011.

Pacific Sentry. Ammonia Detection Sensors/Monitors for Water Applications. http://www.pacificsentry.com/water.html. Accessed on Jul. 1, 2013.

Sutron. DS5x Multiparameter Water Quality Sonde Datasheet. Jun. 1, 2012.

Seneye. Retail Brochure for Aquatic Warning System. http://www.seneye.com. Accessed Jul. 11, 2012.

U.S. Appl. No. 13/713,818, Jan. 24, 2014, Office Action.

U.S. Appl. No. 13/713,629, Jan. 28, 2014, Office Action.

U.S. Appl. No. 13/713,537, Dec. 3, 2013, Office Action.

U.S. Appl. No. 13/713,495, filed Dec. 13, 2013.

U.S. Appl. No. 13/713,537, filed Dec. 13, 2013.

U.S. Appl. No. 13/713,568, filed Dec. 13, 2013.

U.S. Appl. No. 13/713,595, filed Dec. 13, 2013.

U.S. Appl. No. 13/713,629, filed Dec. 13, 2013.

U.S. Appl. No. 13/713,668, filed Dec. 13, 2013.

U.S. Appl. No. 13/713,714, filed Dec. 13, 2013.

U.S. Appl. No. 13/713,737, filed Dec. 13, 2013.

U.S. Appl. No. 13/713,773, filed Dec. 13, 2013.

U.S. Appl. No. 13/713,818, filed Dec. 13, 2013.

U.S. Appl. No. 13/713,864, filed Dec. 13, 2013.

* cited by examiner

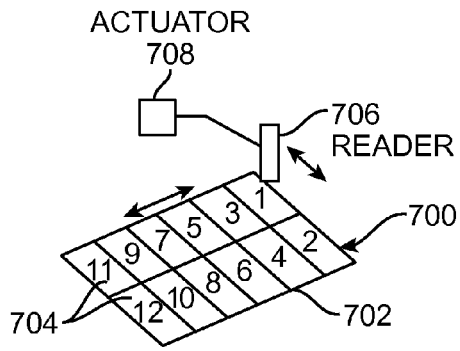
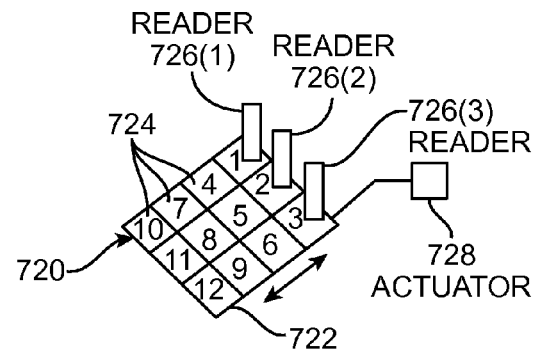
FIG. 7A
FIG. 7B
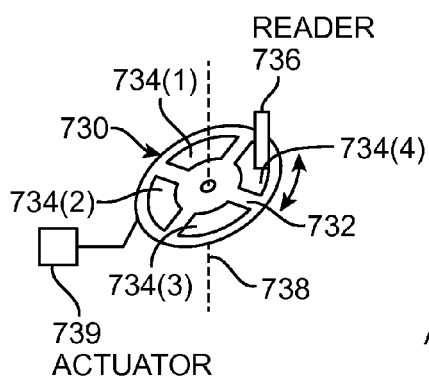
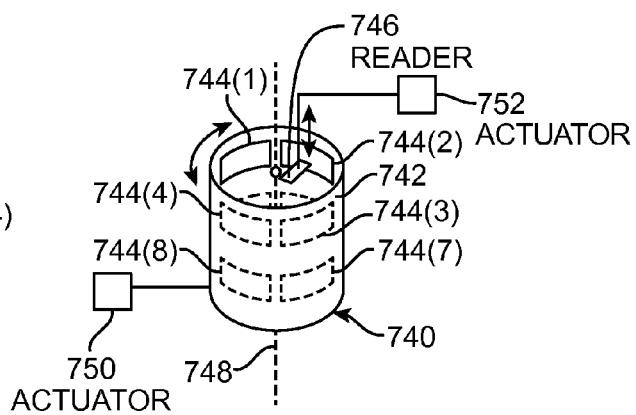
FIG. 7C
FIG. 7D
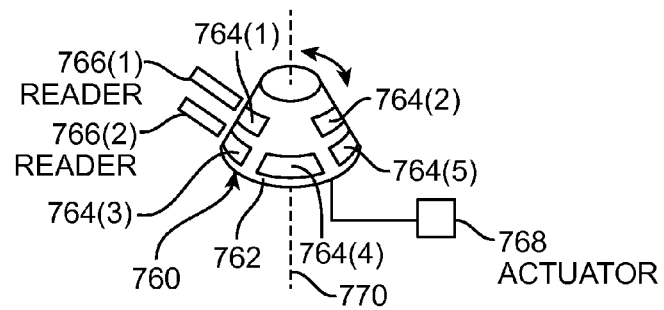
FIG. 7E

AQUATIC ENVIRONMENT WATER-QUALITY MONITOR HAVING A SUBMERSIBLE CHEMICAL INDICATOR WHEEL

RELATED APPLICATION DATA

This application is a continuation application of International Application No. PCT/US12/69209, filed Dec. 12, 2012, entitled "Aquatic Environment Monitoring and Dosing Systems and Apparatuses, and Methods and Software Relating Thereto," which application claims the benefit of priority of U.S. Provisional Patent Application Ser. No. 61/630,450, filed Dec. 12, 2011, entitled "Aquarium Monitor," both of which are incorporated by reference herein in their entirety.

This application is related to commonly-owned U.S. patent application Ser. No. 13/713,495, entitled "Submersible Chemical Indicator Apparatuses For Use In Aquatic-Environment Monitoring/Measuring System;" and U.S. patent application Ser. No. 13/713,568, entitled "Embedded Indicator Dye Monitoring System and Method for An Aquatic Environment;" and U.S. patent application Ser. No. 13/713,595, entitled "Combined Illuminator/Light Collectors For Optical Readers;" and U.S. patent application Ser. No. 13/713,629, entitled "Dosage Protection System and Method For An Aquatic Environment;" and U.S. patent application Ser. No. 13/713,668, entitled "Chemical Indicator Obstruction Detection System and Method For An Aquatic Environment;" and U.S. patent application Ser. No. 13/713,714, entitled "Rate of Change Protection System and Method for an Aquatic Environment;" and U.S. patent application Ser. No. 13/713,737, entitled "Monitoring of Photo-Aging of Light-Based Chemical Indicators Using Cumulative Exposure Tracking, and Systems, Methods, Apparatuses, and Software Relating Thereto;" and U.S. patent application Ser. No. 13/713,773, entitled "Monitoring of Photo-Aging of Light-Based Chemical Indicators Using Illumination-Brightness Differential Scheme, and Systems, Methods, Apparatuses, and Software Relating Thereto;" and U.S. patent application Ser. No. 13/713,818, entitled "Assisted Dosing of Aquatic Environments For Maintaining Water Quality Therein, and Systems, Methods, Apparatuses, and Software Relating Thereto;" and U.S. patent application Ser. No. 13/713,864, entitled "Optical Reader Optic Cleaning Systems Having Motion Deployed Cleaning Elements, and Methods of Cleaning An Optical Reader Optic," each of which is filed on the same day as this application: Dec. 13, 2012, each of which is incorporated by reference herein in its entirety.

FIELD OF THE INVENTION

The present invention generally relates to the field of water quality management, such as for fish and coral aquariums, swimming pools, and hot tubs, among other aquatic environments. In particular, the present invention is directed to aquatic environment monitoring and dosing systems and apparatuses, and methods and software relating thereto.

BACKGROUND

Measuring and maintaining the quality of water is important in a wide variety of circumstances. For example, for keeping fish and/or other aquatic life, the quality of the water must be kept within certain tolerances to keep the aquatic life healthy. As another example, the water in swimming and diving pools, hot tubs, and other sports, recreational, and therapeutic bodies of water need to be kept at certain levels of quality not only to maintain that water's clarity, but also to keep the users of these bodies of water safe from waterborne illnesses. As yet another example, the quality of potable water needs to be maintained within a range of tolerances as to a variety of chemical constituents for any one or more of a number of reasons, such as to make the water safe for ingesting, less harmful to distribution systems, and to promote healthfulness of the drinkers (e.g., in the case of adding fluorine and/or other nutrients). Those skilled in the art will readily appreciate that these are but a few examples of settings in which it is important to monitor and/or control the quality of water.

SUMMARY OF THE DISCLOSURE

In one implementation, the present disclosure is directed to a water-quality monitoring system for monitoring quality of water in an aquatic environment. The system includes a chemical indicator wheel designed and configured to be submerged in the water of the aquatic environment during use, the chemical indicator wheel including: a holder having a rotational axis; and a plurality of chemical indicators fixedly supported by the holder, wherein the plurality of chemical indicators are designed and configured to undergo optically detectable changes in response to changes in levels of corresponding respective differing constituents of the water; and a monitoring unit that includes: an optical reader designed and configured to acquire optical readings of each of the plurality of indicators; and a drive system designed and configured to drive the chemical indicator wheel to at least one reading position for each of the plurality of chemical indicators, wherein the optical reader can take a reading.

In another implementation, the present disclosure is directed to a water-quality monitoring unit for monitoring quality of water in an aquatic environment, wherein the monitoring is designed and configured to rotatably drive a chemical indicator wheel designed and configured to be submerged in the water of the aquatic environment during use, the chemical indicator wheel having a rotational axis and including a plurality of chemical indicators designed and configured to undergo optically detectable changes in response to changes in levels of corresponding respective differing constituents of the water. The monitoring unit includes an optical reader designed and configured to acquire optical readings of each of the plurality of indicators; and a drive system designed and configured to drive the chemical indicator wheel to at least one reading position for each of the plurality of chemical indicators, wherein the optical reader can take a reading.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 7A is high-level schematic diagram illustrating a first exemplary chemical indicator apparatus/reader arrangement;

FIG. 7B is high-level schematic diagram illustrating a second exemplary chemical indicator apparatus/reader arrangement;

FIG. 7C is high-level schematic diagram illustrating a third exemplary chemical indicator apparatus/reader arrangement;

FIG. 7D is high-level schematic diagram illustrating a fourth exemplary chemical indicator apparatus/reader arrangement;

FIG. 7E is high-level schematic diagram illustrating a fifth exemplary chemical indicator apparatus/reader arrangement;

DETAILED DESCRIPTION

Figure 1:
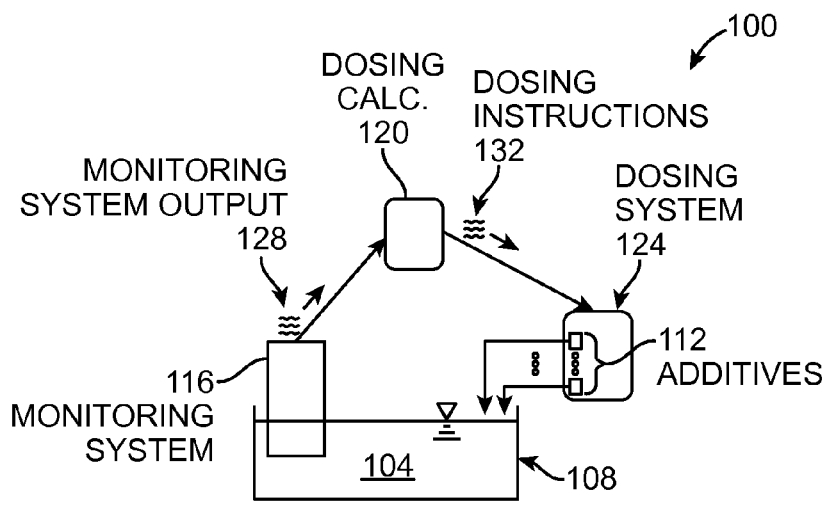
FIG. 1 is high-level block/schematic diagram illustrating an aquatic environment setup that includes a water quality monitoring and dosing system.

Some aspects of the present invention are directed to systems for measuring and/or monitoring the quality of water in various aquatic environments and for dosing, when the monitoring determines that the water quality is outside one or more predetermined tolerances, the water with one or more additives in corresponding respective amounts that bring the water quality into the predetermined tolerance(s). As those skilled in the art will readily understand from reading this entire disclosure, despite the fact that this introductory section addresses systems for monitoring and/or dosing, other aspects of the present invention lie within individual components, apparatuses, methods, and software of such a system, as well as within methods, apparatuses, systems, and software not directly involved in monitoring and/or dosing but related thereto, such as systems, methods, and software for social networking based on water quality monitoring and methods, systems and apparatuses that are especially adapted to be used with various monitoring and dosing systems and apparatuses disclosed herein.

Before describing several exemplary water quality monitoring and dosing systems, the term "aquatic environment" is defined, for example, to give the reader a sense of the wide applicability of the systems, apparatuses, methods, and software disclosed herein. As used herein and in the appended claims, "aquatic environment" shall mean any environment wherein water is present and for which it is desired to measure at least one parameter indicative of a quality of the water. In turn, "quality" is measured by the presence, absence, and/or amount of one or more chemicals, including minerals, in the water, and/or the presence, absence, and/or amount of one or more other materials, such as organic matter, inorganic particles, bacteria, etc., in the water, and any combination thereof. Examples of aquatic environments include, but are not limited to: aquariums, including aquarium sumps and aquarium plumbing; swimming/diving/wave pools, including swimming/diving/wave pool plumbing; hot tubs, including hot tub plumbing; fish ponds, including fish pond plumbing; potable water supplies, including plumbing therefor; sewage treatment infrastructure; water fountains; water displays; lakes and lagoons, and control structures and plumbing therefor (such as at amusement parks and other facilities having highly controlled environments); and food processing facilities that use water, for example, to wash food items, cook food items, transport food items, to name just a few. Those skilled in the art will certainly be able to think of other examples of aquatic environments for which teachings of the present disclosure will be pertinent. In this connection, while many of the examples herein are directed to aquarium set ups for keeping fish, coral, and/or other aquatic life, skilled artisans will readily be able to adapt the fundamental teachings herein to virtually any other aquatic environment wherein water quality measurement and/or monitoring and dosing is desired.

Referring now to the drawings, FIG. 1 illustrates a water quality monitoring and dosing system 100 being used to monitor one or more parameters of water 104 in an aquatic environment 108 and to provide proper dosing of one or more additives 112 to the water so that the quality of the water is maintained within its desired tolerance(s), depending on the number and type of parameters measured. It is noted that aquatic environment 108 can be any aquatic environment, such as one of the aquatic environments noted above, wherein water quality monitoring and dosing is desired. It is also noted that examples of measurable parameters are described below in detail. That said, those skilled in the art of water quality measuring will readily understand which one or more water parameters need to be measured for a given aquatic environment.

System 100 includes a monitoring system 116, a dosing calculator 120, and a dosing system 124. Before describing each of these parts of system 100, it is noted that the diagram in FIG. 1 does not necessarily represent distinct components of the system, rather, this diagram is intended to convey functionality of the system over physical form of the system. Thus, while system 100 can be composed of components that correspond in a one-to-one manner to the functionality blocks of FIG. 1, this need not be so. For example, dosing calculator 120 need not be a standalone device; it can be in any suitable form, such as a set of software instructions executed onboard a component of monitoring system 116, onboard a component of dosing system 124, or onboard another component or device, such as a computing device (not shown) (e.g., webserver, smartphone, home computer, laptop computer, tablet computer, desktop computer, etc.) located remotely from aquatic environment 108. Because those skilled in the art will be able to conjure a variety of ways of discretizing and componentizing the functionality blocks representing monitoring system 116, dosing calculator 120, and dosing system 124, it is not necessary to describe all combinations and permutations herein for those skilled artisans to appreciate the myriad ways that system 100 of FIG. 1 can be implemented across components local to aquatic environment 108 and/or across components located remotely relative to the aquatic environment.

Monitoring system 116 is designed and configured to monitor (i.e., measure repeatedly) at least one parameter indicative of the quality of water 104 in aquatic environment 108. Though the number of measured parameters can be as few as one, in many applications, such as aquarium monitoring applications, the number of measured parameters will typically be four or more, as will be seen below in the context of specific examples. Monitoring system 116 can monitor each of the parameters using one or more suitable technology(ies), such as one or more chemical indicators that each undergo a physical change that can be sensed (read), one or more electrodes, one or more chemical probes, among others, and any combination thereof. Monitoring system 116 generates one or more outputs 128 indicative of the measurement(s) taken by the monitoring system and outputs the resulting signal(s) to dosing calculator 120. In one example, monitoring system 116 takes the measurement(s) and outputs the corresponding output(s) 128 multiple times (e.g., periodically or at differing intervals) over a given time period in a manner that attempts to ensure that none of the measured parameters goes out of range or goes out of range long enough to risk damage to aquatic environment 108, its contents, and/or its users. Each output 128 can be in any suitable form, such as a raw analog signal, a raw digital signal, or a digitally converted value, among others. The type of output used in a particular implementation may depend, for example, on whether dosing calculator 120 is implemented within monitoring system 116 where raw signals can be readily utilized or outside of the monitoring system, such as in dosing system 124 or on a remote device, such as a computing device (not shown) (e.g., laptop computer, tablet computer, webserver, smartphone, desktop computer etc.), where it is easier to convey converted values via a suitable communications protocol, such as transmission control protocol/Internet protocol (TCP/IP), among others. Other examples of computing devices that can be used are disclosed below in connection with FIG. 50.

Dosing calculator 120 is designed and configured to determine whether or not any one or more of the measured parameters are out of acceptable range and, if so, how much of one or more additives 112 that dosing system 124 should add to water 104 with the goal of restoring the one or more out-of-range parameters to the corresponding respective acceptable ranges. Depending on the type of a particular additive 112, the dosing may be made all at once or it may be made over a period of time. For example, some additives cannot be added too quickly without detrimental effects, and so need to be dosed at a rate that avoids the detrimental effects. In order for dosing calculator 120 to make its out-of-range and dosing determinations, it must know certain information about aquatic environment 108 and/or water 104, such as the volume of the water, the nature of environment (e.g., it contains certain fauna and/or flora), and the acceptable range(s) of the measured parameter(s), among others. Dosing calculator 120 may communicate dosing instructions 132 to dosing system 124 in any manner suited to the implementation. For example, if dosing calculator 120 is located so that it must use a data communications protocol, such as TCP/IP, the dosing instructions may include the additive type(s) and an amount of each additive 112 that dosing system 124 should dispense. In another data communications protocol example, the dosing instructions can include instructions that tell dosing system 124 which additive(s) to dispense and how long to dispense each additive needed. This latter example requires that dosing calculator 120 knows how much additive is dispensed per unit of time. In other implementations in which dosing calculator 120 communicates directly with dosing system 124, the instructions can be in another form, such as a voltage signal or a digital signal. As will become apparent from reading this entire disclosure, monitoring system 116 can comprise or consist of any of the monitoring systems, or part(s) thereof, described herein or any other suitable monitoring system. Likewise, dosing calculator 120 can be implemented in any suitable manner, such as any one of the manners described in this disclosure. Similarly, dosing system 124 can comprise any of the dosing systems, or part(s) thereof, described herein or any other suitable dosing system. It is noted that although FIG. 1 has been described above as including monitoring system 116, dosing calculator 120, and dosing system 124, an aquatic environment setup of the present disclosure can include any one or combination of those components or other similar components, several examples of which are described in this disclosure. In addition, it is noted that while monitoring system 116, dosing calculator 120, and dosing system 124 are described above without much detail on specific features, it is noted that any one of these components can be provided with any one or more of the applicable features described herein relative to specific examples.

Figure 2:
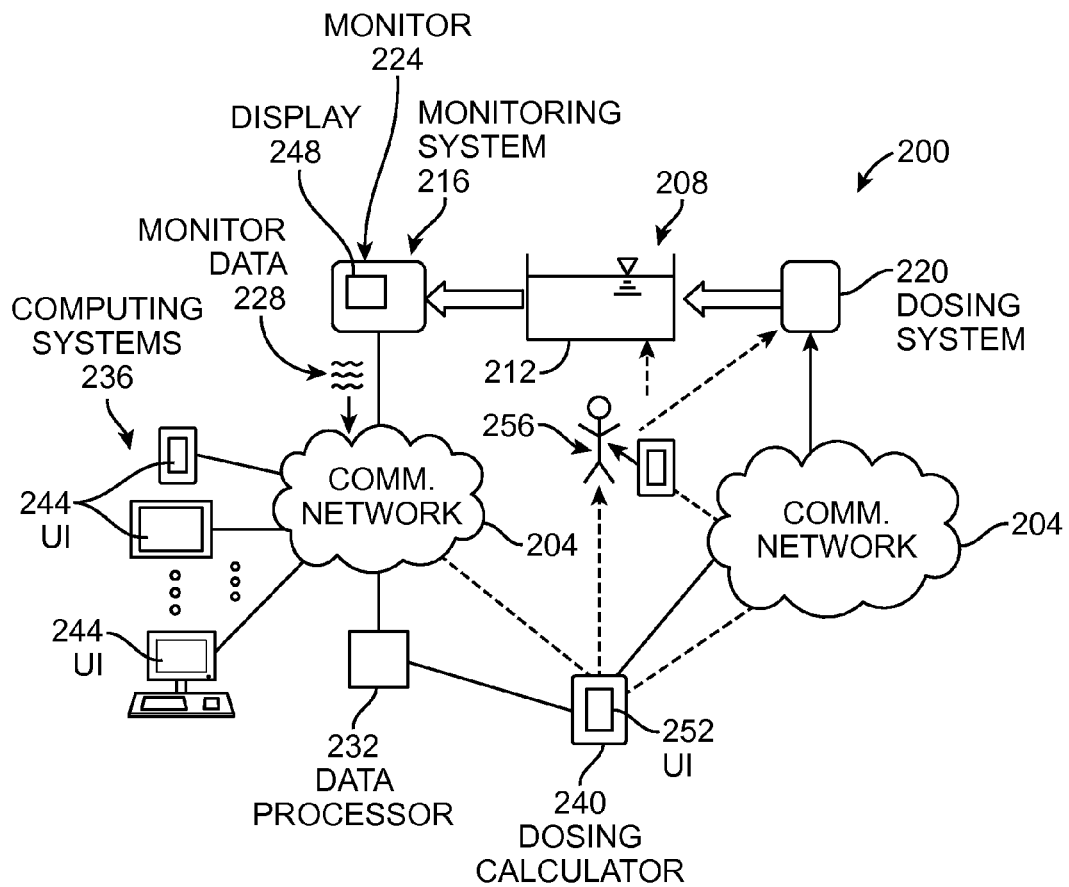
FIG. 2 is a high-level block/schematic diagram illustrating an exemplary implementation of a water quality monitoring and dosing system that utilizes a communications network for implementing various functionalities of and/or relating to the system.

FIG. 2 illustrates an exemplary embodiment of a water quality monitoring and dosing system 200 implemented over a communications network 204, which comprises wired communications links, wireless communications links, or both Examples of a communications network include, but are not limited to, a local area network, a wide area network, a cellular telecommunications network, and a global network (e.g., the Internet), other network type, and any combination thereof. System 200 includes an aquatic environment 208 containing water 212 that is monitored by a monitoring system 216 for one or more parameters relating to its quality and is dosed, as necessary, with one or more additives by a dosing system 220 in a manner that maintains the quality of the water within one or more tolerance bands. As with system 100 of FIG. 1 above, monitoring system 216 and dosing system 220 of FIG. 2 can be, for example, any of the monitoring systems and dosing systems, respectively, described herein or any other suitable monitoring or dosing system. Also as with system 100 of FIG. 1, the one or more parameters can be any parameter(s) relevant to the nature of the water quality at issue.

Monitoring system 216 includes a monitor 224 that monitors one or more of the parameters, for example, by reading one or more indicator devices (not shown), such as one or more chemical indicators, one or more electrodes, one or more probes, etc. In the exemplary system 200 of FIG. 2, monitoring system 216 generates monitor data 228 containing information regarding readings of the one or more parameters and sends the monitor data to a data processor 232 via communications network 204. Data processor 232, which can reside on one or more computing systems 236, for example, on one or more webservers, one or more client devices (e.g., tablets computers, laptop computers, smartphones, etc.) or other computing system in data communication with communications network 204, processes monitor data 228 as needed to allow the monitor data to be displayed to a user and/or to control dosing system 220. In this connection, data processor 232 can include a dosing calculator 240. Alternatively, dosing calculator 240 can be located elsewhere, such as within dosing system 220. In addition, if dosing calculator 240 is not part of data processor 232, monitor data 228 can be processed by data processor 232 prior to being sent to dosing calculator 240 or, alternatively, the monitor data can be sent directly to the dosing calculator.

Each computing system 236 may also include a user interface 244 that allows a user to access monitoring data 228 either in its unprocessed format or in a processed format, or both. As an example of unprocessed format, researchers, professional aquarists, enthusiasts, troubleshooters, etc., may find it desirable to have all of the "raw" data provided by monitor 224. On the other hand, consumers, casual users, hobbyists, etc., may only desire a version of monitor data 228 that has been processed, such as to present the data to the user in a simplified form, such as graphically, binary (e.g., in tolerance/out of tolerance), etc. Those skilled in the art will readily be able to understand the benefits and formats of processed and unprocessed formats of monitor data 228, such that further description is not necessary herein for them to appreciate the broad scope of the present invention. It is noted that the processing and displaying of monitor data 228 and data derived therefrom through processing can be distributed over two or more computing systems 236. For example, in a webserver/client context, the webserver may provide some initial processing of monitor data 228 while a client device, for example, via a smartphone "app" (i.e., a software application), receives the processed data from the webserver and uses that data to generate one or more suitable graphical displays on the client device representing the monitor data.

In another example, a client device may receive unprocessed monitor data 228, in which case a software application on the client device may use the unprocessed data directly to create suitable graphical displays and/or allow a user to use the unprocessed monitor data in another way. As yet another example, a computing system 236, such as a smartphone, laptop computer, tablet computer, desktop computer, etc., may receive monitor data 228 directly, for example, via a wired or wireless data connection, and that system may include a software application for processing monitor data 228, or not, and use either the processed data or unprocessed data, or both, in any suitable manner, such as for producing graphical displays or transferring the data to a spreadsheet or other program for detailed analysis, among many other possibilities. In still a further example, monitor 224 itself may provide a relatively high level of data processing, such that monitor data 228 is already processed for high level use, such as graphical display by one or more computing system 236. It is noted that if monitor 224 processes its reading data, it may contain one or more onboard displays 248, which can be, for example, visual (e.g., visual indicator(s), electronic display(s), etc.), aural (e.g., sound generator for generating one or more sounds, spoken words, etc.), or a combination of visual and aural displays.

Dosing calculator 240 can be embodied and realized in any of a number of ways. In addition to being located at various locations within system 200 as noted above, dosing calculator 240 can be configured to provide dosing instructions for manual dosing or automated dosing, or both. Manual dosing can be performed in any one or more of a variety of ways. For example, if dosing system 220 is manually controllable, i.e., requires a human operator to control the dosing, dosing calculator 240 can be augmented with a user interface 252 that displays an indication of the amount of each additive that the user needs to cause dosing system 220 to dispense. Depending on the type of additive and any limitations of dosing rate, such indication may be accompanied by further dosing instructions advising the user of the dosing rate parameters. In this connection, depending on how they are implemented, user interface 252 and/or dosing calculator 240 may need to be aware of information regarding dosing system 220, such as make and model, that allow the user interface and/or dosing calculator to provide instructions specific to the dosing system being used.

In another example, dosing system 220 may not be present at all, such that the dosing needs to be carried out virtually entirely by a human user 256, using, for example, chemicals and/or other additives that are provided in bulk form in individual containers and need to be manually dispensed or taken from such containers by the human user. In this example, if each/any of the additives is available in differing forms (e.g., powder, liquid, gel, etc.) and/or in differing concentrations, etc., then user interface 252 and/or dosing calculator 240 may need to be aware of information regarding the specific additive(s) being used, such as brand and formulation, that allow the user interface and/or dosing calculator to provide instructions specific to the particular additive(s) being used. Examples of dosing systems and additives for particular applications are described below. However, those skilled in the art will readily understand that these examples are illustrative and not limiting.

Figure 3:
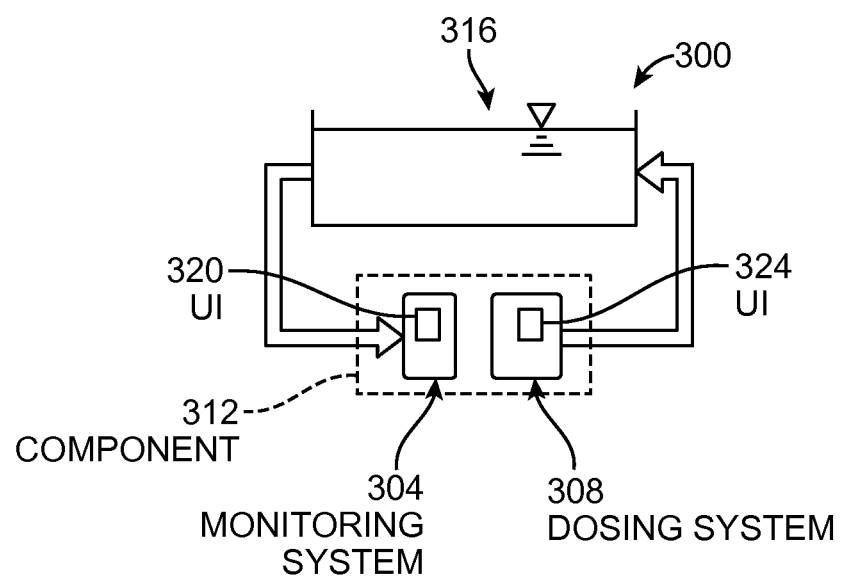
FIG. 3 is a high-level block/schematic diagram illustrating an exemplary implementation of a standalone water quality monitoring and dosing system.

Whereas FIG. 2 illustrates a water quality monitoring and dosing system 200 that can be monitored and/or controlled from virtually any location having access to communications network 204, which in the case of the Internet, for example, can be virtually any location on earth (e.g., using a satellite link for highly remote locations) or even off of Earth, FIG. 3 illustrates a setup 300 including a monitoring system 304 and a dosing system 308 that are in very close proximity to one another. Indeed, in some instantiations, they are combined into an integral unit with one another, and in some cases, into an integral unit with a component 312 of an aquatic environment 316, such as an aquarium, a sump, plumbing, a filter, a heater, an overflow, a skimmer, etc., and any suitable combination thereof. In other embodiments, wherein monitoring system 304 and dosing system 308 are not integrated into a common unit, they can nevertheless be located close together, such as in differing parts of aquatic environment 316 or differing parts of a component 312. Depending on the spacing of monitoring system 304 and dosing system 308 from one another, they can be in data communication via any suitable means, such as wired communication or wireless communication. Examples of suitable wireless communication includes short-range radio communication and infrared communication, among others.

In some instantiations, setup 300 can be self-contained, i.e., not require communication of monitor data to any devices outside of monitoring system 304, and dosing system 308 or communication of control data, for example, data needed to set operating parameters of the system, from any device outside of the monitoring and dosing systems. However, it is noted that system 300 can be outfitted with such external communications capability if so desired. In such cases, outside communications capability can be provided via any suitable wired or wireless technology available. In either case, monitoring system 304 and/or dosing system 308 can be provided with any suitable user interface(s), such as interfaces 320 and 324, that allow(s) a user to control operating parameters of system 300.

Figure 4:
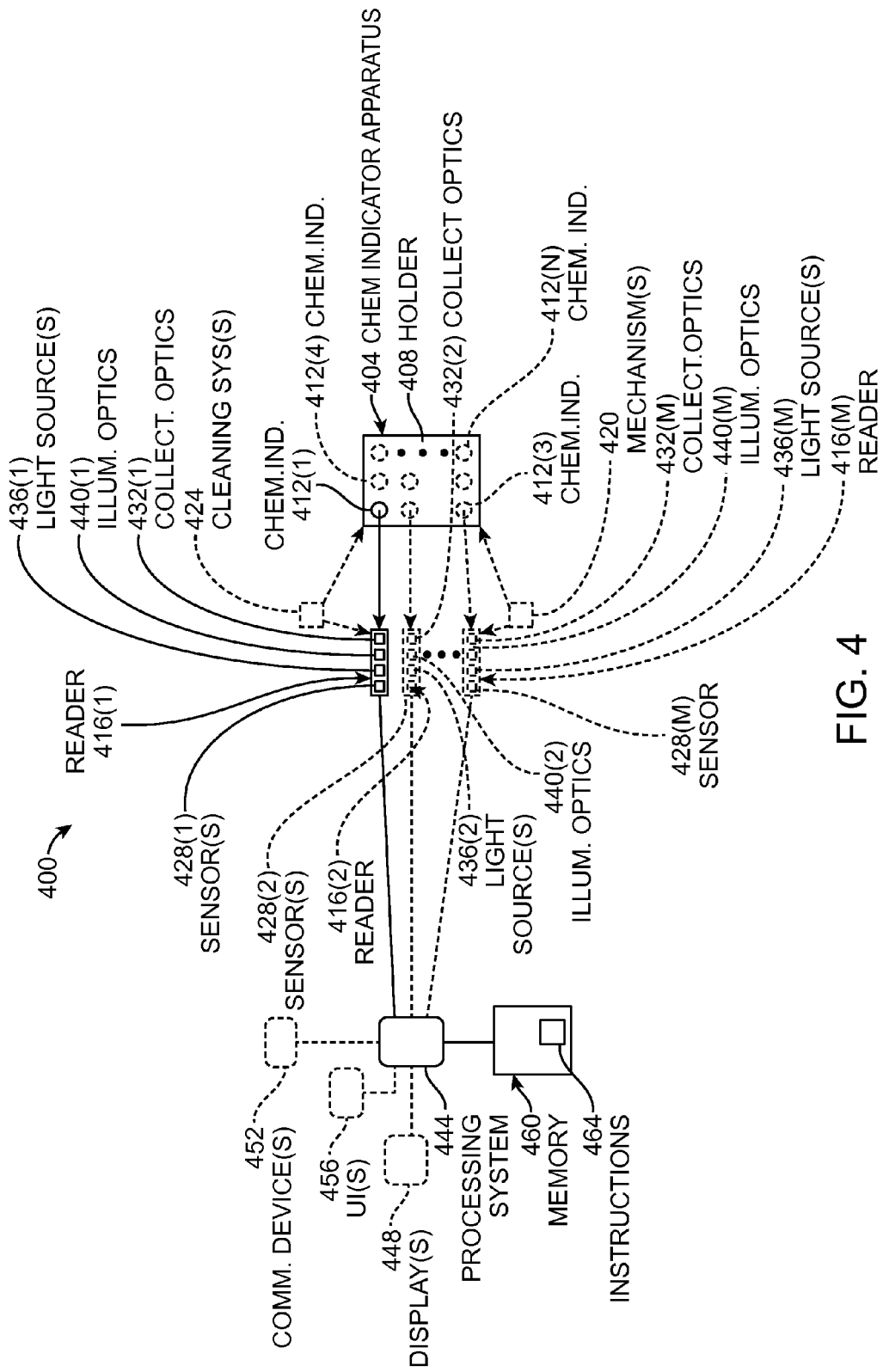
FIG. 4 is a high-level block/schematic diagram illustrating a chemical indicator reading system.

FIG. 4 illustrates a water parameter reading system 400 that can, for example, be adapted for use in any one of water quality monitoring and dosing systems 100, 200, and 300 of FIGS. 1, 2, and 3, respectively, or other water quality monitoring and dosing system, and/or that can be adapted for use as a water quality monitoring system and/or as a water testing system, among other things. For example, water parameter reading system 400 can be integrated into monitoring system 116 of FIG. 1 or any other monitoring system disclosed herein, In the example of FIG. 4, water parameter reading system 400 includes a chemical indicator apparatus 404 comprising a holder 408 that supports one or more chemical indicators 412(1) to 412(N) each of which is designed and configured to undergo a detectable physical change as the amount of one or more constituents/properties that make up the water (not shown) under consideration. Examples of detectable physical change include, but are not limited to, change in fluorescence, fluorescence decay (e.g., lifetime fluorescence), phase fluorescence, change in electromagnetic energy absorptance (change in reflectivity), and change in color, among others. In one embodiment, each chemical indicator 412(1) to 412(N) comprises one or more indicator dyes immobilized in a suitable medium, such as a gel, a polymer matrix (such as a cellulosic matrix), etc. In one example, immobilization includes covalent bonding of a dye to cellulose fibers which in turn are immobilized in a medium such as a hydrogel.

In one example, when one or more of chemical indicators 412(1) to 412(N) are submersible chemical indicators, it is noted that the chemical indicators are stable in water, i.e., the active dyes remain contained in the mediums and they do not mix with, and they do not change, the water in which they are submerged. Each chemical indicator 412(1) to 412(N) is preferably reversible. Examples of constituents/properties of water, the levels of which can be detected using suitable chemical indicators, include, but are not limited to, pH, hardness, calcium, magnesium, oxygen ($O_2$), carbon dioxide, ammonia, phosphate, nitrate. Depending on the type of aquatic environment (not shown, but see, e.g., aquatic environments 108, 208, and 316 of FIGS. 1, 2, and 3, respectively) for which monitoring or testing is being performed using system 400, it may be desirable to test certain combinations of individual parameters. A number of examples of such combinations are described below for various fresh water, saltwater, and brackish water embodiments. It will be understood that those examples are merely illustrative, and that those skilled in the art will understand what parameter(s) and/or combinations of parameters are desirable for a wide variety of applications, such as applications involving various stages of potable water treatment, sewage treatment, etc. Also described below are various examples of chemical indicators and the corresponding parameters they can be used to measure.

In another example, an aquatic environment monitoring apparatus may include a plurality of immobilized chemical indicators supported by a chemical indicator holder. Various holders are discussed further below. Such a chemical indicator holder having a plurality of immobilized chemical indicators can be illuminated by light (e.g., excitation light for fluorescence, reference illumination, etc.) from an optical reader. Various optical readers are also discussed herein. In one example of a chemical holder that can be used with an aquatic environment monitoring system (such as those disclosed herein), a chemical holder (e.g., a discoidal holder) includes a chemical indicator dye sensitive for detecting calcium in the aquatic environment, a chemical indicator dye sensitive for detecting magnesium in the aquatic environment, and a chemical indicator dye sensitive for detecting carbon dioxide in the aquatic environment. In this example each of the chemical indicator dyes are immobilized in an immobilizing medium, such as a cellulosic hydrogel medium. Examples of a chemical indicator dye sensitive for calcium include, but are not limited to, a calcium detecting aminonaphthalimide, a calcium detecting perylenediamide, and any combination thereof. Examples of a chemical indicator dye sensitive for magnesium include, but are not limited to, a magnesium detecting dye based on a aminonaphthalimide, a magnesium detecting dye based on a photon induced electron transfer process (PET), a magnesium detecting dye based on a intramolecular charge transfer process (ICT), a magnesium detecting perylenediamide and any combinations thereof. Examples of a chemical indicator dye sensitive for carbon dioxide include, but are not limited to, a carbon dioxide sensitive dye based on a aminonaphthalimide, a carbon dioxide sensitive dye based on a photon induced electron transfer process (PET), a carbon dioxide sensitive dye based on a intramolecular charge transfer process (ICT), a carbon dioxide sensitive perylenediamide and any combinations thereof.

Figure 5:
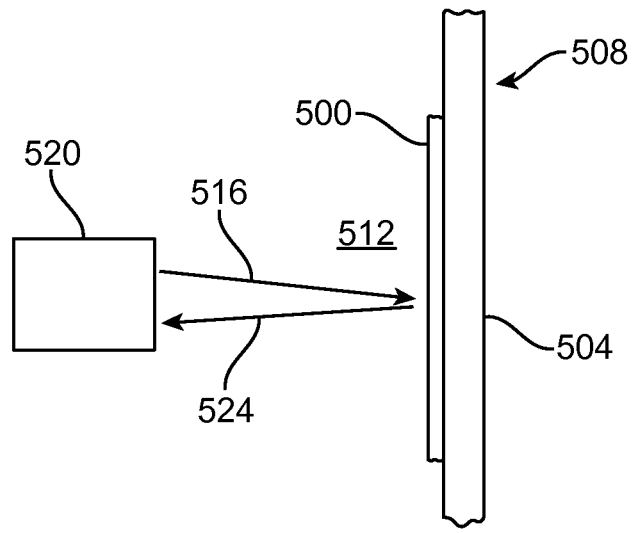
FIG. 5 is a cross-sectional view illustrating an exemplary arrangement for a chemical indicator on a chemical indicator apparatus.
Figure 6:
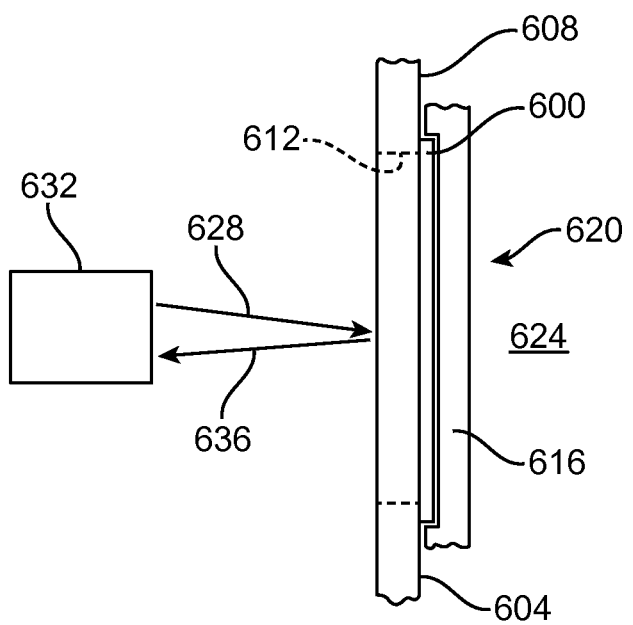
FIG. 6 is a cross-sectional view illustrating an alternative exemplary arrangement for a chemical indicator on a chemical indicator apparatus.

FIG. 5 illustrates an exemplary arrangement of a chemical indicator 500 on a holder 504 of a chemical indicator apparatus 508. In this example, chemical indicator 500 is secured to holder 504. With this configuration, chemical indicator 500 is directly exposed to water 512 for which the chemical indicator is designed for use. During use, chemical indicator 500 is illuminated by light 516 from a suitable optical reader 520 and return light 524 is collected therefrom by the optical reader. Chemical indicator 500 can be any one of chemical indicators 412(1) to 412(N) of FIG. 4. FIG. 6 illustrates another exemplary arrangement of a chemical indicator 600 on a holder 604 of a chemical indicator apparatus 608. In this example, chemical indicator 600 is secured to holder 604, which in this example is transparent at least to the wavelength(s) of light necessary for the chemical indicator to be used as an optical indicator. Alternatively, if holder 604 is generally opaque to the relevant wavelength(s), it can be provided with a suitable window 612 that is transparent to the necessary wavelength(s). A light blocking backing 616 that blocks light from the backside 620 of holder 604 is positioned adjacent chemical indicator 600 between the chemical indicator and water 624. Light blocking backing 616 can be porous so as to allow water 624 to reach chemical indicator 600, since the opposite side of the chemical indicator is not in contact with the water because of holder 604 and/or window 612. In one example, light blocking backing 616 can be a light blocking hydrogel, such as a carbon-containing hydrogel. During use, chemical indicator 600 is illuminated by light 628 from a suitable optical reader 632 and return light 636 is collected therefrom by the optical reader. Chemical indicator 600 can be any one of chemical indicators 412(1) to 412(N) of FIG. 4. Referring again to FIG. 4, holder 408 can have any of a wide variety of shapes and can be made of any one or more of a wide variety of materials suitable for a particular application. For example, for a saltwater application, the material(s) should not corrode or otherwise be attacked by the saltwater. Regarding shape, exemplary shapes for holder 408 include, but are not limited to, planar, discoidal, cylindrical, frusto-conical, spherical, ellipsoidal, parallelepiped, etc. Further regarding shape, holder 408 can be made in any suitable form, such as solid (i.e., without openings), fenestrated, trussed, stretched membrane, etc., and can be made as a unitary monolithic part or assembled from two or more discretely manufactured parts. Regarding material(s) of construction, virtually any material(s) can be used. Fundamentally, there is no particular limitation on how holder 408 can be constructed and made.

Water parameter reading system 400 further includes one or more readers 416(1) to 416(M) designed and configured to read the physical change(s) of one or more of chemical indicators 412(1) to 412(N). Some embodiments have a one-to-one correspondence between the number of readers. That is, each chemical indicator 412(1) to 412(N) has a corresponding respective reader 416(1) to 416(M), i.e., M=N. In other embodiments, there are fewer readers 416(1) to 416(M) than chemical indicators 412(1) to 412(N), i.e., M<N, and in still other embodiments there are multiple readers per chemical indicator, i.e., M>N. Any of these embodiments can optionally include one or more mechanisms 420 for moving one or more readers 416(1) to 416(M) relative to chemical indicator apparatus 404, or for moving the chemical indicator apparatus relative to the reader(s), or both. Depending on the configuration of reading system 400 and chemical indicator apparatus 404, the movement that the one or more mechanisms 420 can impart to the driven part (e.g., one of or group of readers 416(1) to 416(M) or chemical indicator apparatus 404) can be in any one or more of the six degrees of freedom (three linear+three rotational) available for motion.

FIGS. 7A to 7E illustrate five exemplary movement scenarios for readers and chemical indicator apparatuses. Each of these and many other scenarios can be implemented in water parameter reading system of the present disclosure, such as system 400 of FIG. 4. In FIG. 7A, a chemical indicator apparatus 700 includes a rectangular, planar holder 702 supporting twelve chemical indicators 704(1) to 704(12) arranged in a 2×6 array. In this example, a single reader 706 is movable in two linear directions relative to chemical indicator apparatus 700 by a suitable actuator 708 so that the reader can be positioned proximate to each one of chemical indicators 704(1) to 704(12) for reading that chemical indicator. For reasons described in more detail below relative to error minimization, actuator 708 can be designed, configured, and suitably controlled to position reader 706 at multiple positions proximate to each chemical indicator 704(1) to 704(12).

FIG. 7B shows a chemical indicator apparatus 720 that includes a rectangular, planar holder 722 that supports twelve chemical indicators 724(1) to 724(12) arranged in a 3×4 array. In this example, three readers 726(1) to 726(3), corresponding respectively to the three rows of chemical indicators 724(1) to 724(12), are stationary, and chemical indicator apparatus 720 is movable in a single linear dimension relative to the readers by a suitable actuator 728. For reasons described in more detail below relative to error minimization, actuator 728 can be designed, configured, and suitably controlled to position the ones of chemical indicators 724(1) to 724(12) at multiple positions relative to the corresponding respective readers 726(1) to 726(3).

In FIG. 7C, a chemical indicator apparatus 730 includes a discoidal holder 732 that supports four chemical indicators 734(1) to 734(4) arranged annularly about the holder. In this example, a single reader 736 is stationary, and chemical indicator apparatus 730 is rotationally movable about a rotational axis 738 by a suitable actuator 739. For reasons described in more detail below relative to error minimization, actuator 739 can be designed, configured, and suitably controlled to position each chemical indicator 734(1) to 734(4) relative to reader 736.

FIG. 7D illustrates a chemical indicator apparatus 740 that includes a cylindrical holder 742 that supports eight chemical indicators 744(1) to 744(8) arranged on the interior of the holder in two bands of four indicators each. A single reader 746 is provided. To enable single reader 746 to read all eight chemical indicators 744(1) to 744(8), chemical indicator apparatus 740 is rotatable about its central longitudinal axis 748 via a suitable actuator 750, and the reader is movable linearly in a direction parallel to central longitudinal axis 748 via a suitable actuator 752. It is noted that one, the other, or both of actuators 750 and 752 can be actuated to allow reader 746 to be positioned at multiple locations at each of one, some, or all of chemical indicators 744(1) to 744(8).

Referring to FIG. 7E, this figure shows a chemical indicator apparatus 760 that includes a frusto-conical holder 762 that supports twelve chemical indicators 764 (only five of which, i.e., indicators 764(1) to 764(5), are visible) arranged in two bands, one with four indicators and the other with eight indicators. A pair of fixed readers 766(1) and 766(2) are provided, one for reading the upper band and the other for reading the lower band. In this example, a single actuator 768 is provided to rotate chemical indicator apparatus 760 about its central longitudinal axis 770. As with other examples, if desired actuator 768 can be controlled to provide one position for each reader 766(1) and 766(2) relative to the corresponding pair of chemical indicators 764 or multiple positions, for example, for error checking and minimization purposes.

Returning to FIG. 4, regardless of how chemical indicator apparatus 404 is configured, it can be made to be a consumable product that needs to be replaced from time to time, for example, to avoid undesirable effects of deterioration of the one or more chemical indicators 412(1) to 412(N) from interfering with proper readings by any one or more of readers 416(1) to 416(M). It is also noted that the set of chemical indicators 412(1) to 412(N) provided on chemical indicator apparatus 404 can vary from instantiation to instantiation. A reason for doing this is to allow the same reader(s) 416(1) to 416(M) to be used for differing applications wherein one or more differing parameters and/or one or more ranges within one or more parameters are desired/needed to be determined. Examples of varying chemical indicator sets among instantiations of chemical indicator apparatus 404 are provided below in the context of aquatic-life-supporting aquatic environments, such as aquariums and fish ponds, wherein differing chemical indicator sets are provided for freshwater fish species, saltwater fish species, brackish water species, saltwater coral species, and aquarium cycling/setup due to the differing parameters that are desired and/or necessary to be determined.

Chemical indicator apparatus 404 can be designed and configured to be fully or partially submerged (collectively referred to herein and in the appended claims as "submerged") in the water (not shown) of the aquatic environment in which water parameter reading system 400 is deployed. It is noted further that the term "submerged" covers not only the cases of full and partial submersion, for example, in an aquarium, aquarium sump, pond, pool, etc., but also the case of exposure of chemical indicator apparatus 404 to the aquatic environment water within inline plumbing. An example of an inline plumbing instantiation of a water parameter reading system is described below.

Depending on the environment in which chemical indicator apparatus 404 is operating, one or more of readers 416(1) to 416(M) and/or one or more of chemical indicators 412(1) to 412(N) may experience fouling, for example, from algae or other matter building up over time. To combat this fouling, water parameter reading system 400 may include a cleaning system 424 that continuously, intermittently, or periodically cleans critical components of any one or more of readers 416(1) to 416(M) and/or chemical indicator apparatus 404. Examples of cleaning systems that can be used for cleaning system 424 include ultrasound-based cleaning systems, vibration-based cleaning systems, light-based (e.g., UV light to kill organisms) cleaning systems, contact-type (e.g., brush, squeegee, etc.) cleaning systems, and filtered water-jet-based cleaning systems, among others, and any combination thereof. Those skilled in the art will be able to implement, after reading this entire disclosure, any one of these systems given the overall configuration of water parameter reading system and the configuration of interaction of its components in a particular instantiation.

Each of readers 416(1) to 416(M) can be any suitable type of reader for the particular one(s) of chemical indicator(s) 412(1) to 412(N) that the reader at issue is designed and configured to read. For optically read chemical indicators, for example, chemical indicators in which chemical changes are observable by detecting: the amount of light absorbed, fluoresced upon excitation, and/or reflected and/or the color of light absorbed, fluoresced, and/or reflected, etc., and any combination thereof, one or more of reader(s) 416(1) to 416(M) can be an optical reader capable of detecting such amount(s) and/or color(s). Correspondingly, each reader can include one or more detectors (sensors) 428(1) to 428(M) capable of detecting (sensing) the one or more characteristics of the relevant light. As used herein, the term "light" covers electromagnetic radiation in traditional light spectrum, which includes not only visible light, but also infrared (near and far)

light, and ultraviolet light. Examples of such optical sensors include, but are not limited to photo-detectors, line cameras, array cameras, charge-coupled device-based sensors, and CMOS-based sensors, among many others. Fundamentally, there are no limitations of the type and configuration of suitable light detectors/sensors as long as they perform the requisite function(s).

Depending on the type(s) and location(s) of detector(s)/sensor(s) 428(1) to 428(M) in each reader 416(1) to 416(M), light from the relevant chemical indicator(s) 412(1) to 412(N) may need to be collected and/or transmitted from each chemical indicator to the detector(s)/sensor(s). Such collection and/or transmission can be accomplished using any suitable optics 432(1) to 432(M). In addition to conventional optics, for example, optical fibers, lenses, light pipes, etc., any of the unique light conductors disclosed herein can be used for optics 432(1) to 432(M). In embodiments wherein any one of readers 416(1) to 416(M) needs to emit light of certain spectral content to illuminate any one or more of chemical indicators 412(1) to 412(N), each of the readers may include one or more suitable light sources 436(1) to 436(M) and/or suitable optics 440(1) to 440(M) for projecting and/or directing the light from the light source(s) to the appropriate chemical indicator(s). Examples of light sources that can be used for any one or more of light sources 436(1) to 436(M) include, but are not limited to, LEDs, lasers, incandescent bulbs or other sources, and any combination thereof. As those skilled in the art will appreciate, each light source 436(1) to 436(M) can include one or more light filters (not shown) as needed to create the desired/necessary spectral content. In addition to conventional optics, for example, optical fibers, lenses, light pipes, etc., any of the unique illuminating optics disclosed herein can be used for optics 440(1) to 440(M). In some embodiments wherein both collection and illumination optics 432(1) to 432(M) and 440(1) to 440(M) are used in a reader, they can be combined as taught below, for example, in the context of combined illuminators/light collectors 1604 and 1800 of FIGS. 16 and 18, respectively.

Water parameter reading system 400 may include a processing system 444 that includes one or more processors for controlling the overall operations of the system and implementing whichever of the above-described and other functionalities that a designer chooses to embody in the system. For example, processing system 444 can control each of readers 416(1) to 416(M), mechanism(s) 420 for moving the reader(s) and/or chemical indicator apparatus 404, one or more displays 448, cleaning system 424, one or more communications devices 452, and/or one or more user interfaces 456, among other things, as may be present. Exemplary processors that can be used for each of the one or more processors in processing system 444 include, but are not limited to, an application specific integrated circuit, a microprocessor, a system on chip, etc. Processing system 444 is in communications with one or more memories (collectively represented by memory 460), which can comprise any one or more types of memories, including, but not limited to, cache memory, random-access memory (RAM) (such as dynamic RAM and/or static RAM), read-only memory, removable hardware storage media (such as magnetic storage devices, optical storage device, flash-memory devices, etc.). Memory 460 can contain suitable machine-executable instructions 464 executable by processing system 444 to perform any one or more of the functionalities imparted into water parameter reading system 400.

Each display 448 can be any type of display desired to present one or more outputs to a user and, in some cases, such as with video displays, receive one or more inputs from a user. Examples of displays that can be implemented include, but are not limited to, video displays (such as flat panel video displays (LCD, LED, etc.) and CRT video displays, touchscreen or not), indicator light displays, audio displays, gauges, and non-video flat panel displays (e.g., LCD and LED panels, touchscreen or not), among many others. Fundamentally, there is no limitation on the type(s) of display(s) 448 that can be used in water parameter reading system 400. Similarly, each user interface 456 can be any suitable type of user interface, such as hard and soft user interfaces implemented via software and hardware. Fundamentally, there is no limitation on the type(s) of user interface(s) 456 that can be used in water parameter reading system 400. Each communications device 2252 can be any communications device that is desired to be used to provide water parameter reading system 400, and can be a wired device, such as wired communications port (e.g., universal serial bus port, FIREWIRE® port, HDMI port, RCA jack port, etc.) or can be a wireless transmitter, receiver, or transceiver based on radio-frequency communications (e.g., an IEEE 802.11 standard device and a cellular telecommunications device), on microwave communications, on ultrasonic communications, on optical communications (e.g., an infrared device), or on magnetic communications (e.g., an inductively coupled device), among others. Fundamentally, there is no limitation on the type(s) of communications device(s) 452 that can be used in water parameter reading system 400. Examples of various ones of the components of water parameter reading system 400 are provided below in connection with presentations of several exemplary embodiments of aquatic environment monitoring/measuring systems.

Exemplary Aquarium Monitoring System

Figure 8:
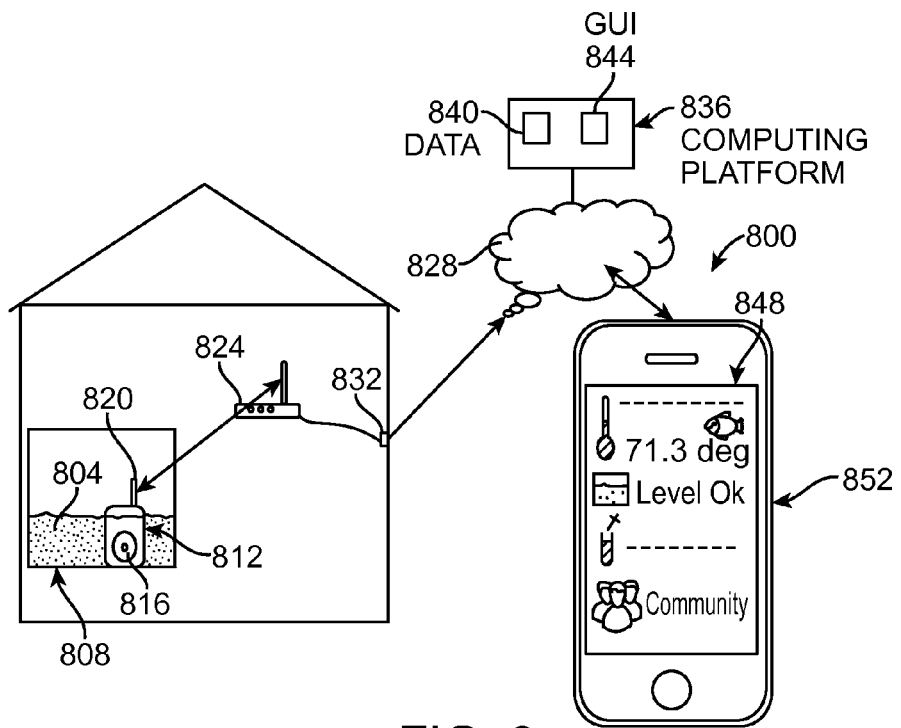
FIG. 8 is a schematic diagram illustrating an exemplary aquarium monitoring system that includes a discoidal chemical monitoring apparatus.

FIG. 8 illustrates an exemplary aquarium monitoring system 800 designed and configured to continually monitor a number of parameters of water 804 within an aquatic environment having a component 808, such as an aquarium or aquarium sump, that contains at least a portion of the water being monitored. In this example, system 800 includes a monitoring unit 812 at least partially submerged in water 804, and monitors, according to user designated control parameters, the ecological conditions of the aquatic environment by continually reading a plurality of water parameters of interest. Monitoring unit 812 removably receives a chemical indicator apparatus, hereafter referred to as "chemical indicator disc 816," that, as described below, includes a plurality of chemical indicators (not shown) that, as described above, each undergo detectable physical changes with changes in the level of certain constituents of water 804. It is noted that while the term "disc" is appropriate for chemical indicator apparatus 816 due to its discoidal shape, for the purpose of the present disclosure and the appended claims, the term "wheel," when referring to a chemical indicator apparatus, shall mean any chemical indicator apparatus that is rotated by a monitoring/measurement unit, water parameter reading system, or other measurement and/or monitor device disclosed herein about a rotational axis and that resembles a wheel. For example, chemical indicator disc 816 is a wheel, as are chemical indicator apparatuses 7E30 of FIG. 7E, 1916 of FIG. 19, 2508 of FIG. 25, 4100 of FIGS. 41, and 4412 of FIG. 44. Chemical indicator disc 816 is described below in detail.

Exemplary monitoring unit 812 communicates the ecological conditions, here wirelessly via an onboard antenna 820 (in this example an above-water antenna, but a submersible antenna could be used), to a wireless communications device, such as a WIFI™ router 824, via any suitable communications protocol, here an IEEE 802.11 protocol. Router 824 is connected to a communications network 828, for example, a global communications network such as the Internet, via a suitable connection 832. Connection 832 to communication network F28 enables access to a cloud computing platform 836, which can, among other things, store data 840 from monitoring unit 812, run analyses on such data, provide a web-based GUI 844 for the display of raw, processed, and/or analyzed forms of the data, provide a web-based GUI 848 for allowing a user to control the monitoring unit, provide raw, processed, and/or analyzed forms of the data to a remote device 852, such as a computing device, (e.g., smartphone, tablet computer, laptop computer, desktop computer, etc.), and control one or more applications.

Figure 9:
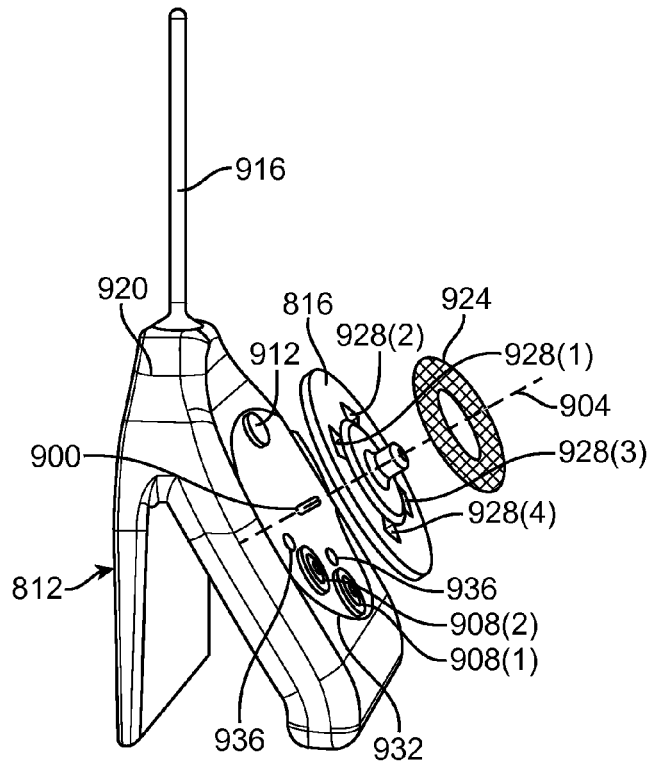
FIG. 9 is a partially exploded perspective view of the water quality monitoring system of FIG. 8.

FIG. 9 depicts monitoring unit 812 and chemical indicator disc 816 in more detail. During use, monitoring unit 812 receives replaceable chemical indicator disc 816 on a shaft-type receiver 900 so that the disc is able to rotate about its central rotational axis 904. As described below, during operation, monitoring unit 812 can, as desired or not, rotate chemical indicator disc 816 about rotational axis 904 for a number of reasons, including for taking readings of the chemical indicators (not shown), for causing water in the space between the disc and the monitoring unit to exchange for water outside that space to expose the chemical indicators to "fresh" water, and for self-cleaning purposes. Chemical indicator disc 816 is positioned overtop one or more reader ports, in this example, optical reader ports 908(1) and 908(2) and an ultraviolet (UV) light port 912. As described in detail below, optical reader ports 908(1) and 908(2) allow optical readers (not shown) onboard monitoring unit 812 to optically read the chemical indicators onboard chemical indicator disc 816, and UV light port 912 is provided for sterilizing any biological material that might attach to the disc. As mentioned, monitoring unit 812 has one or more antennas 820, each of which is preferably, though not necessarily, mounted internally and/or externally, and/or mounted at the top of the unit and to keep the antenna(s) out of water for best reception and transmission. In one example, monitoring unit 812 is designed so that the top portion of the unit above water line 920 is above water and the lower portion of the unit below water line 920 is submerged during use.

In one embodiment, monitoring unit 812 and corresponding chemical indicator disc 816 are designed and manufactured to have a weight that is close to the weight of the water displaced by the unit and disc when they are installed in the water wherein they will be used. In an embodiment that is engaged with a wall of an aquarium or other container via magnetic coupling with a magnetic device on the exterior of the aquarium or other container (such as described below), it is beneficial to have the combined weight of monitoring unit 812 and disc 816 and the displaced water be close to one another so that the unit (with disc attached) do not tend to slide up or down along the engaged wall. In addition, smaller holding magnets can be used. In addition, if the combined weight of monitoring unit 812 and disc 816 is slightly less than the weight of the displaced water, then if the unit does disengage from the wall, then it will not sink so that it can be easily reached by a user. Monitoring unit 812 can include a 3-axis accelerometer (such as accelerometer 2276 of monitoring unit 2202 of FIG. 22), and this accelerometer can be used to detect abnormal movement (tilting, vertical slipping, and/or rotation, etc.) of the unit that indicates disengagement with the wall or other undesirable movement. In one example, the combined weight of monitoring unit 812 and disc 816 is about 220 g, whereas the weight of the water displaced by them in their normal operating location is about 240 g.

Chemical indicator disc 816 includes an optional filter 924 that covers flow passages in the disc, here four flow passages 928(1) to 928(4) that allows water to flow from one side of the disc to the other. While four flow passages 928(1) to 928(4) are shown, more or fewer passages can be provided to suit a particular design. Each flow passage 928(1) to 928(4) can be enhanced with one or more features that assist the flow of water therethrough when disc 816 is being rotated by monitoring unit 812. For example, when monitoring unit 812 is rotating disc 816 in a counterclockwise direction when looking toward the monitoring unit along rotational axis 904, the flow assisting feature(s) of each flow passage 928(1) to 928(4) can pull water into the space between the disc and monitoring unit. In this example, filter 924 is used to filter the water being pulled into that space. This can be beneficial to reducing the amount of light-scattering particulate and/or other matter in the water present in that space during measurement readings, which in turn can increase the accuracy of the readings. In one scenario, monitoring unit 812 can be programmed to perform a flush cycle in which it spins disc 816 for a predetermined amount of time and a predetermined speed (and direction) sufficient to pull water into the space between the disc and the monitoring unit just prior to taking one or more measurement readings. Since the water being pulled in is being filtered by filter 924, during the immediately subsequent reading(s) the water in that space is as clean as practicable. It is noted that flushing can also be beneficial in embodiments not including any filters (such as filter 924) and that one or more filters are useful outside the context of flushing.

Figure 10:
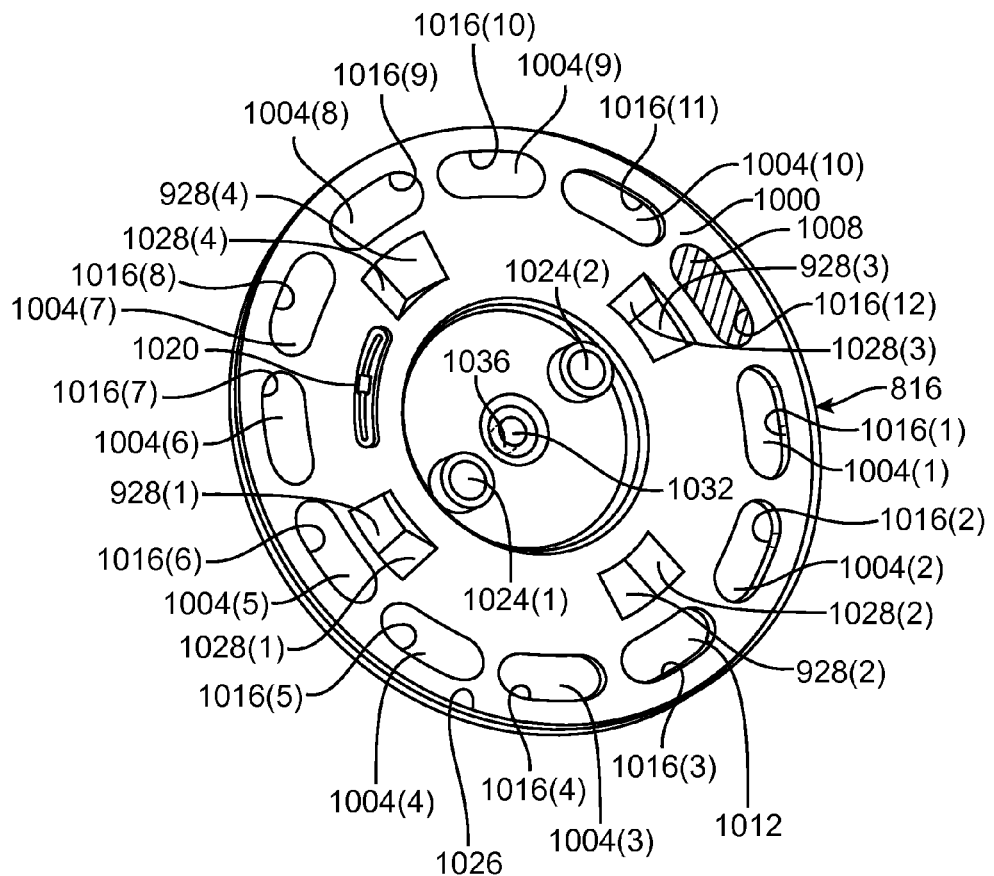
FIG. 10 is an isometric view of a chemical indicator disc that can be used, for example, with the monitoring system of FIG. 9.

FIG. 10 illustrates exemplary chemical indicator disc 816 in more detail than depicted in FIGS. 8 and 9. As seen in FIG. 10, disc 816 comprises a generally discoidal holder 1000, which, in this example, holds ten chemical indicators, here in the form of indicator patches 1004(1) to 1004(10) that are arranged in an annular manner about disc 816 and contain various dyes. It is noted that although ten chemical indicators 1004(1) to 1004(10) are shown, in other embodiments disc 816 or similar disc can have more or fewer indicators as needed and/or desired to suit a particular application. In this example, each indicator patch 1004(1) to 1004(10) is gel-based and contains a dye that either changes in its light absorbance or its fluorescence, or both, as a function of the amount of one or more particular constituents of the water to which the patches are exposed, such as water 804 of FIG. 8. Also in this example, the dyes contained in indicator patches 1004(1) to 1004(10) are selected for testing saltwater and are as follows: patch 1004(1) contains a magnesium indicator dye; patch 1004(2) contains a calcium indicator dye; patch 1004(3) contains a phosphate indicator dye; patch 1004(4) contains a nitrate indicator dye; patch 1004(5) contains a nitrite indicator dye; patch 1004(6) contains a pH indicator dye (Type 1); patch 1004(7) contains a pH indicator dye (Type 2); patch 1004(8) contains an ammonia indicator dye; patch 1004(9) contains a dissolved oxygen indicator dye; and patch 1004(10) contains a sensor age dye. Disc 816 also includes a black reflectance patch 1008 and a white calibration reference patch 1012 for calibrating the readers (not shown) onboard monitoring unit 812 (see, e.g., FIG. 9). It is important to note that the sensing indicators of disc 816 have reversible reactions to the constituents of the water whereby if the concentration of a constituent goes back down to a base level, the sensor dye returns to its original state.

Figure 19:
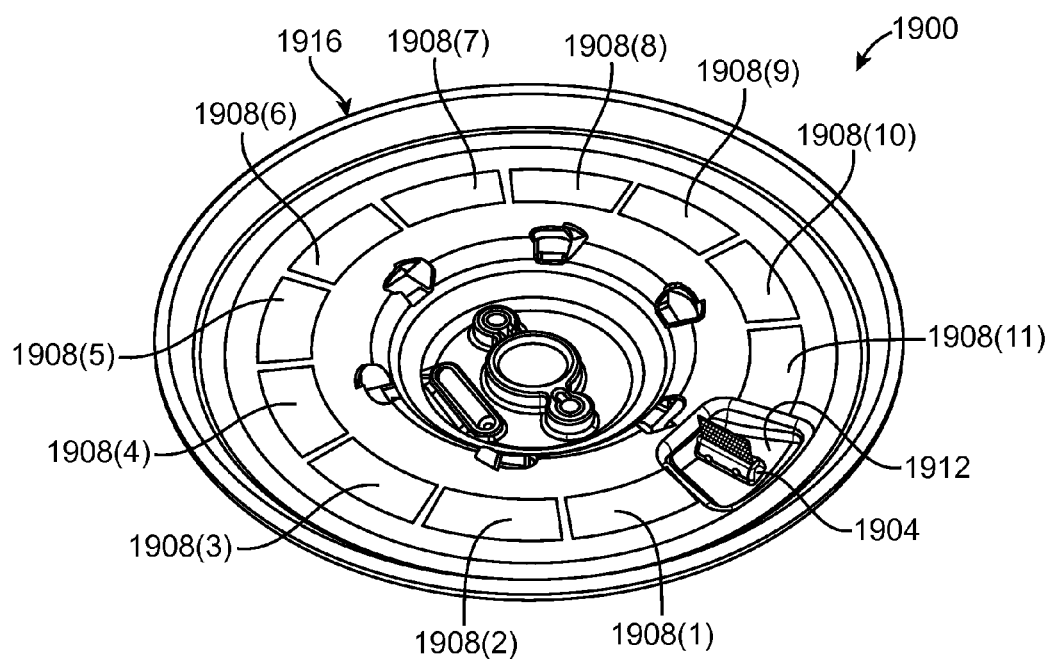
FIG. 19 is an isometric view of a chemical indicator disc having a cleaning element for cleaning one or more components of a water quality monitoring unit.

In the particular embodiment shown, each of patches 1004(1) to 1004(10), 1008, and 1012 is located in a corresponding recess 1016(1) to 1016(12). However, in other embodiments, this need not be the case. For example, depending on the thickness of a particular dye patch it may not reside in a recess, but rather be applied to a non-recessed surface of disc 816. Indeed, in some embodiments, disc 816 may have a completely flat surface in the patch region and all of patches 1004(1) to 1004(10), 1008, and 1012 may be secured to that surface. In addition, it is noted that while patches 1004(1) to 1004(10), 1008, and 1012 are shown as discrete bodies relative to one another, in other embodiments this need not be so. For example, all of patches 1004(1) to 1004(10), 1008, and 1012 can be provided as a unitary structure, such as on an annular substrate to which the various patches are provided. Then, during manufacture, such preformed annular structure can simply be adhered or otherwise secured to holder 1000. In addition, patches 1004(1) to 1004(10), 1008, and 1012 need not necessarily be spaced from one another. On the contrary, for example, adjacent ones of patches 1004(1) to 1004(10), 1008, and 1012 can directly abut one another. It should be noted that while FIG. 8 shows patches with rounded ends, it is preferred but not required to use more rectangular shapes such as shown in FIG. 19 for more efficient use of the space and more optically readable surface area.

Still referring to FIG. 10, the illustrated example of chemical indicator disc 816 includes an information storage device, here a radio-frequency identification (RFID) based integrated circuit (IC) storage device 1020 that can be used to store a variety of information, such as calibration and manufacturing data sets for various ones of indicator patches 1004(1) to 1004(10), disc identification data, disc usage data, and an authentification key to thwart counterfeiting of the disc. As seen below, monitoring unit 812 (see, e.g., FIG. 9) may include a corresponding RFID device (not shown) for reading and/or writing information from or to RFID storage device 1020. While an RFID tag based storage device is shown, other forms of storage devices can be used to store various information, such as some or all of the information noted above. Other forms of storage devices include bar code devices, QR code devices, and magnetic storage, among others. It is noted that in some embodiments, information and data indicated above as being storable on disc 816 can be stored in another location, such as on a monitoring unit or one or more network storage devices, such as one or more webservers, among other locations.

Figure 13:
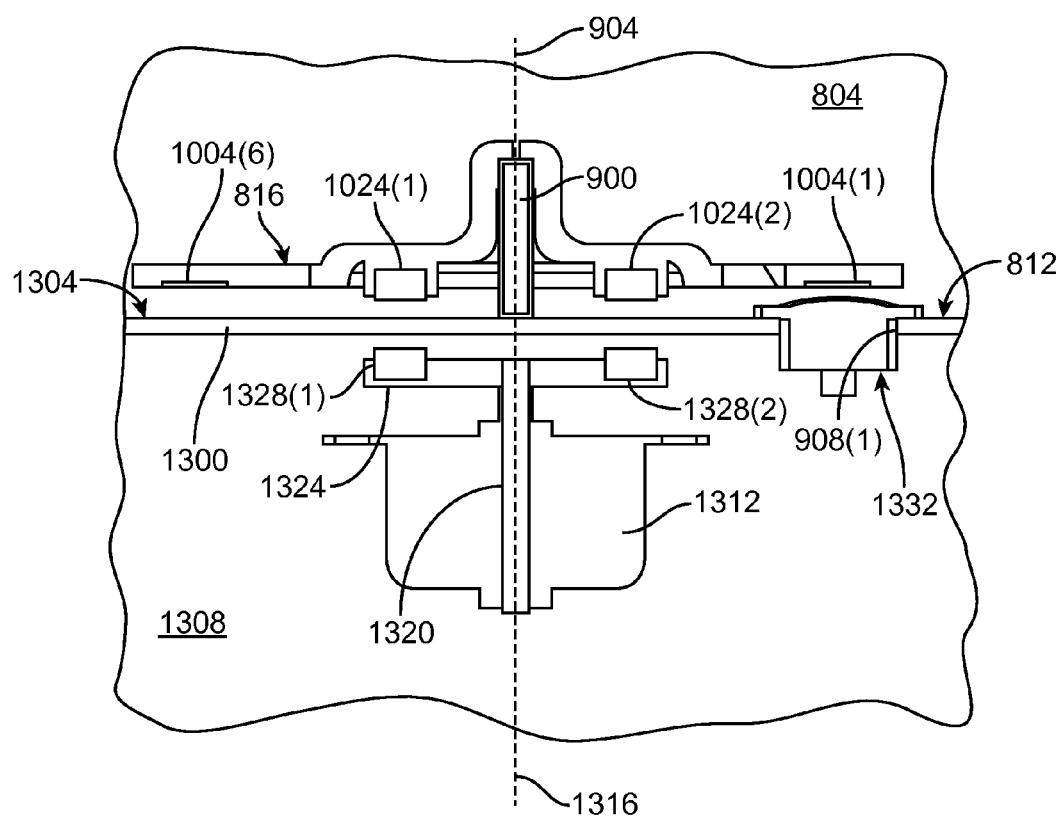
FIG. 13 is a cross-sectional view illustrating several components of the monitoring system of FIG. 8.

In the embodiment shown in FIG. 10, chemical indicator disc 816 is held in engagement with monitoring unit 812 (see, e.g., FIG. 9) using magnetic coupling between, in this example, a pair of permanent magnets 1024(1) and 1024(2) on the disc and a corresponding pair of magnets (KK28(1) and 1328(2) in FIG. 13) inside the monitoring unit. As described below in more detail, this magnetic coupling not only holds disc 816 in engagement with monitoring unit 812, the monitoring unit also uses this magnetic coupling to align the disc and rotate it about rotational axis 904 during use. In some embodiments of aquarium monitoring system 800 (FIG. 8), inhibiting extraneous light from reaching patches 1004(1) to 1004(10), 1008, and 1012 (FIG. 10) to promote the accuracy of the readings is very important. Consequently, disc 816 is provided with a light-blocking feature, here, an apron 1026, that works in conjunction with a cooperating light blocking feature on monitoring unit 812, which as seen in FIG. 9 is a flange 932 shaped similarly to apron 1026 on the disc, as seen in FIG. 10.

Referring again to FIG. 10, as mentioned above chemical indicator disc 816 includes a plurality of flow passages 928(1) to 928(4) having chamfered surfaces 1028(1) to H28(4) that promote the flow of water into the space between the disc and monitoring unit 812 (see, e.g., FIG. 9) during operation to enable the water to transport from one side of the disc to the other side of the disc by way of pressure differentials created by the chamfered edges. Disc 816 also includes an engagement structure, here, a frusto-conically shaped receptacle 1032 designed and configured to be conformally engaged with receiver 900 (FIG. 9) on monitoring unit 816 (also FIG. 9). In some embodiments, receiver 900 (FIG. 9) and receptacle 1032 (FIG. 10) must be designed with some care because it can be very important to have a tight fit to minimize wobble of disc 816 relative to monitoring unit 812 (see, e.g., FIG. 9) but to also allow for relatively friction-free rotation of the disc during operation. Receptacle 1032 may be provided with one or more grooves or other pressure-relieve structure (e.g., aperture) that allows water to flow out of the receptacle as disc 816 is engaged onto receiver 900 (FIG. 9). In addition, receiver 900 and the walls of receptacle 1032 may be at least partially composed of, for example, by impregnation, a relatively low friction material, such as polytetrafluoroethylene, that reduces the friction between the contacting parts to inhibit wear. In some embodiments (see below) receiver 900 (FIG. 9) may be made at least partially of an electrically conductive material and the walls of receptacle 1032 (FIG. 10) may correspondingly have a conductive contact 1036 for conducting electrical charge, for example, to one or more electrodes (one electrode 1100 shown for convenience) onboard disc 816, as shown in FIG. 11.

Figure 11:
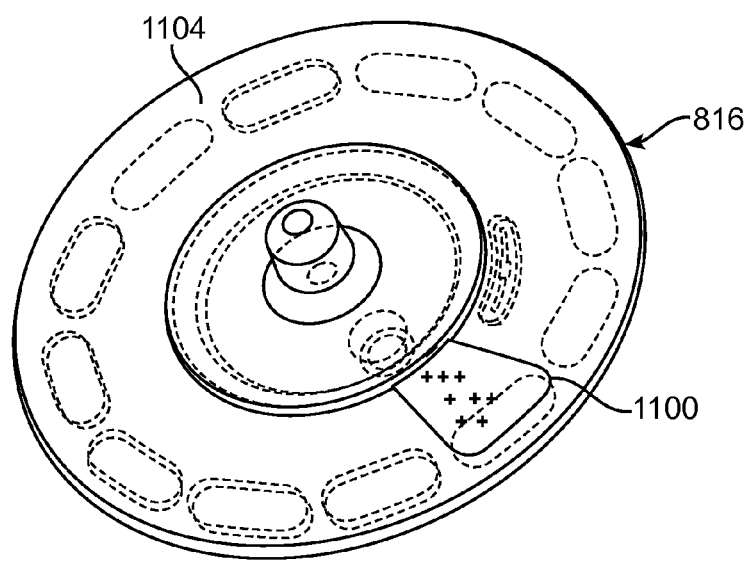
FIG. 11 is an isometric view of another chemical indicator disc that can be used, for example, with the monitoring system of FIG. 9, wherein the disc includes a reading-range-enhancing electrode for enhancing the reading range of a chemical indicator onboard the disc.
Figure 12:
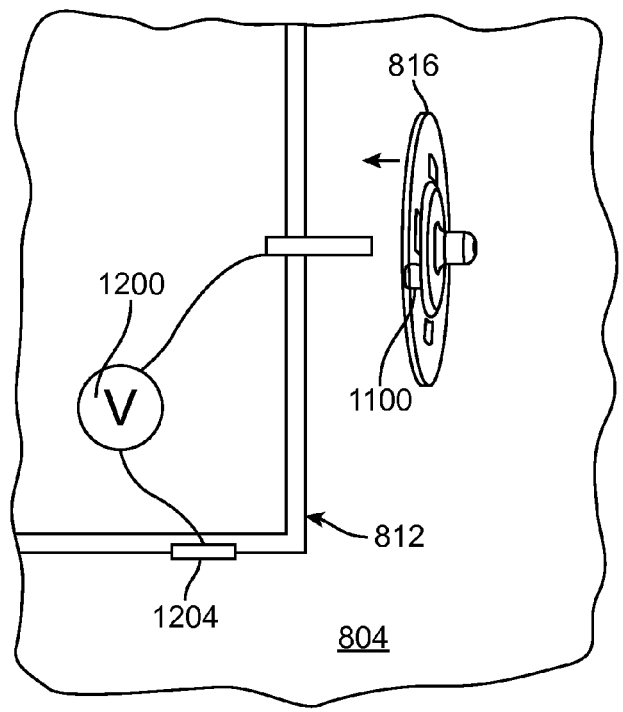
FIG. 12 is a schematic diagram illustrating how the reading range of a chemical indicator can be enhanced using electrical charge.

In FIG. 11, the illustrated embodiment of chemical indicator disc 816 is augmented with electrode 1100 mounted on the "back" side 1104 of the disc, i.e., the side of the disc opposite the side that confronts monitoring unit 812 (see, e.g., FIG. 9) during operation. Electrode 1100 is provided to modify (e.g., extend) the dynamic range of one of chemical indicator patches 1004(1) to 1004(10) (FIG. 10) located on the obverse side of disc 816 opposite the electrode. Referring now to FIG. 11, and also to FIG. 12, when a voltage source 1200 (FIG. 12) within monitoring unit 812 generates a voltage, electrode 1100 (FIGS. 11 and 12), in conjunction with a second electrode 1204 in contact with water 804, creates a current flow within the water being tested. When a positive potential is applied, for example, to electrode 1100 relative to electrode 1204, the chemical cations (not shown) are repelled away from the one of chemical indicator patches 1004(1) to 1004 (10) (FIG. 10) beneath electrode 1100. This reduction of the chemical ions near the affected chemical patch 1004(1) to 1004(10) lowers the response of the dye in that patch. As those skilled in the art will readily understand, using proper calibration of voltage and/or currents, this lowering of the response can be used to effectively extend the range of the affected patch 1004(1) to 1004(10). It should also be noted that the reverse polarity can also be used to attract ions and therefore increase the sensitivity. Pulses of electric charge on 1100 can be used to modulate the optical response of a sensor patch over a very short period of time so that no long term voltage or current is required.

As noted above, a magnetic coupling is used to hold chemical indicator disc 816 (see, e.g., FIG. 9) into engagement with monitoring unit 812 and to allow the monitoring unit to rotate the disc during operation. FIG. 13 illustrates this magnetic coupling, as well as a number of other features. Referring to FIG. 13, monitoring unit 812 includes a wall 1300 that is part of a waterproof enclosure 1304 that keeps the interior 1308 of the monitoring unit and its contents dry. Receiver 900 is fixedly secured to wall 1300 and in FIG. 13 is shown fully engaged by disc 816. A rotary motor 1312, such as a finely controllable electrical stepper motor, is fixedly mounted within interior 1308 of monitoring unit 812 so that its rotational axis 1316 is coincident with rotational axis 904 of the disc. In this example, motor 1312 has a central rotating shaft 1320 that rotates about rotational axis 1316 and has a support bar 1324 fixedly secured at the end thereof. Magnets 1328(1)

and 1328(2) are fixedly secured to support bar 1324 and are movable therewith when motor 1312 rotates shaft 1320. It is noted that while a direct-drive arrangement is shown, those skilled in the art will understand that a transmission, such as a reducing transmission, can be used, especially if it is desired to control the rotation of disc more finely than motor 1312 is directly capable of.

As can be readily appreciated, when opposing pairs of magnets 1328(1), 1328(2), 1024(1), and 1024(2) are of opposing polarities, those pairs attract one another. Thus, chemical indicator disc 816 is magnetically pulled into fully seated engagement with receiver 900. In addition, when motor 1312 rotates support bar 1324, thereby moving the magnets, the magnetic attraction of magnets 1024(1) and 1024(2) to the moving magnets 1328(1) and 1328(2), respectively, causes disc 816 to rotate in virtual unison with the rotating support bar. It is noted that while two pairs of magnets 1328(1), 1328(2), 1024(1), and 1024(2) are illustrated, more or fewer magnets can be used. Regarding the number of magnets provided, it is noted that in some embodiments the number and strength of the magnets need to be carefully selected, as too powerful and/or too many magnets can cause too much friction between disc 816 and monitoring unit 812. If permanent magnets are used, the magnetic force used to hold disc 816 onto receiver 900 should be low enough such that a user can freely remove the disc when it's no longer providing a proper operation. If, for example, electromagnets or other switchable magnets are used, the magnetic coupling may be turned off for disc removal. The magnetic force should also be sufficient to ensure water flow and turbulence against disc 816 will not dislodge it from receiver 900.

Figure 14:
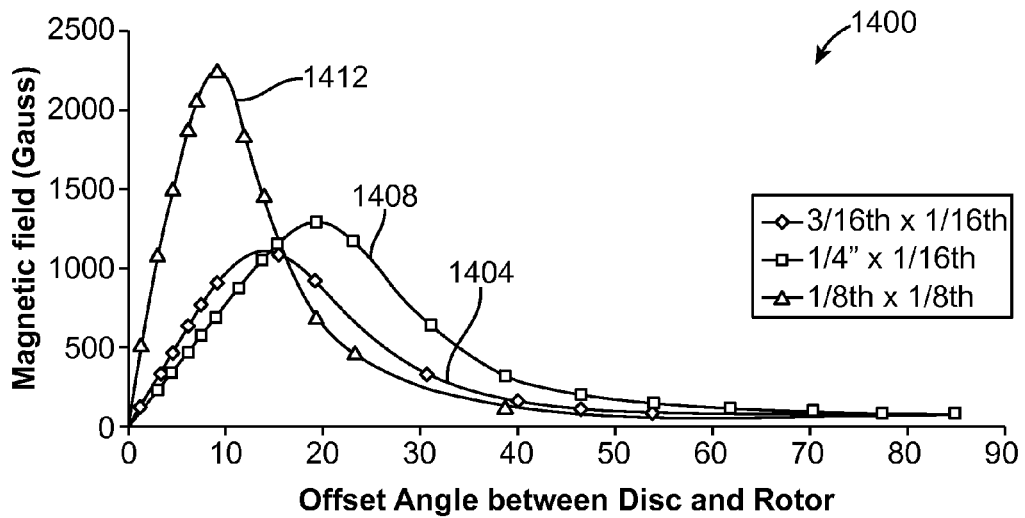
FIG. 14 is a graph of x-axis magnetic field strength versus offset angle for several exemplary magnet sizes in a magnetic drive coupling that can be used in a monitoring/measuring system of the present disclosure.

The present inventor has determined that the shapes of magnets 1328(1), 1328(2), 1024(1), and 1024(2) can have an impact on the performance of the magnetic coupling, especially in the imparting of motion to disc 816. For example, if magnets 1328(1), 1328(2), 1024(1), and 1024(2) are flat discoidal magnets, i.e., have relative large diameters relative to their thicknesses, or are wide magnets of another shape having expansive faces and they are placed so that their expansive faces face one another, the magnetic interaction between the magnets is relatively sloppy, i.e., there is a relatively large amount of play in the alignment. On the other hand, if opposing ones of magnets 1328(1), 1328(2), 1024(1), and 1024(2) are too narrow, when the narrow ends are made to face one another, the magnets can too easily lose their magnetic coupling. FIG. 14 is a graph 1400 illustrating the amount of rotational pull necessary to pull a magnetically coupled rotating body (such as disc 816 of FIGS. 8 and 9) in either direction of rotation based on the size of the magnets used (e.g., magnets 1328(1), 1328(2), 1024(1), and 1024(2)) and offset angle between the magnets on the opposite sides of the magnetic coupling. The pull is illustrated for three sizes of magnets, 3/16"×1/16" (curve 1404), 1/4"×1/16" (curve 1408), and 1/8"×1/8" (curve 1412). At zero offset, the magnets are in near perfect alignment and there is no net pull in either direction (clockwise and counterclockwise). Once rotation of the driving set of magnets is started, they will start to pull via the fields of the driven magnets illustrated in FIG. 14. For the 1/8"×1/8" magnets of curve 1412, the maximum force is obtained at an offset of about 10°. However, in the example of disk 816 and monitoring unit 812 of FIGS. 8 and 9, the friction is low enough that the lag will rarely ever exceed 1° to 2°. In a specific example of magnets 1328(1), 1328(2), 1024(1), and 1024(2), with disc 816 having a diameter of 38 mm, a mass of about 20 g, and a gap of about 2.3 mm between opposing magnets, a Neodymium cylindrical magnet having about a 3.1 mm diameter and a 3.1 mm length has been found to be satisfactory when the circular ends of the opposing magnets are oriented to face one another. Within a certain range, if the gap is large, the diameter can remain constant and the length increased to provide additional magnetic strength. Oppositely, if the gap is smaller, the diameter can remain constant, but the length decreased to provide lesser magnetic strength.

FIG. 13 also illustrates a portion of one of the optical readers mentioned above, that detects one or more optical characteristics and changes in the characteristic(s) in the dye(s) of one or more of chemical indicator patches, only two of which, i.e., patches 1004(1) and 1004(6), are depicted in FIG. 13. The portion of the optical reader illustrated is a combined illuminator/light collector (I/LC) 1332 that is used to illuminate each one of chemical indicator patches 1004(1) to 1004(10) (FIG. 10) that the reader is designed and configured to read, such as patch 1004(1) shown in FIG. 13, and to collect light that reflects and/or emanates (e.g., fluoresces) from that patch as a result of the illumination. Because of the nature of the dyes in the one(s) of chemical indicator patches 1004(1) to 1004(10) (FIG. 10), the amount of light collected by combined I/LC 1332 from each patch is indicative of the level of constituent(s) of water 804 that that patch is designed to measure. Several examples of combined I/LCs suitable for use as combined I/LC 1332 are described below in detail. However, before proceeding to those descriptions, it is noted that in this example, combined I/LC 1332 extends through port 908(1) in wall 1300 and forms a liquid seal therewith to keep water 804 out of interior 1308 of monitoring unit 816. It is noted that the other port in this example, i.e., port 908(2), is occupied by a second combined I/LC (not shown) that is identical to combined I/LC 1332.

Figure 16:
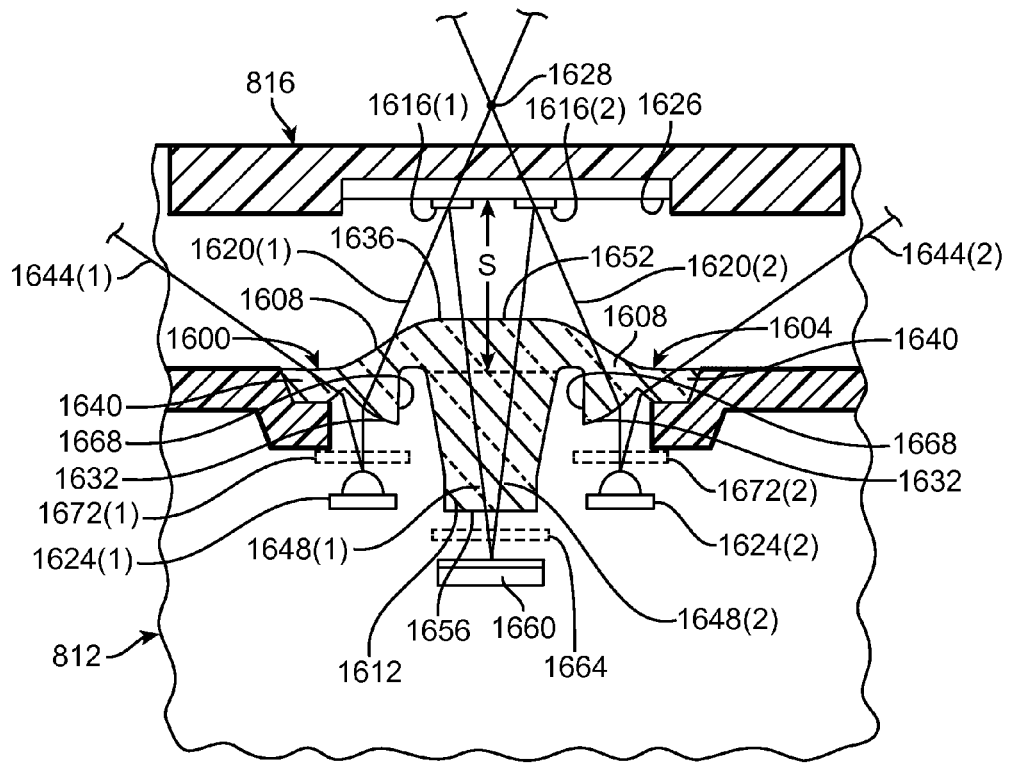
FIG. 16 is an enlarged view of an optical reader that includes a unitary monolithic combined illuminator/light collector (I/LC) that can be used in a water quality monitoring system.

FIG. 16 illustrates combined I/LC 1600 that can be used for combined I/LC 1332 of monitoring unit 812 shown in FIG. 13 or, for example, in any other suitable embodiment of a monitoring unit made in accordance with the present disclosure. As seen in FIG. 16, combined I/LC 1600 comprises a unitary monolithic body 1604 formed from one or more translucent materials, such as acrylic plastic, polycarbonate plastic, glass, sapphire, etc. In one example, when made of a moldable material, monolithic body 1604 can be molded, with little to no subsequent machining or other processing. Combined I/LC 1600 includes spot lensing 1608 and a light pipe 1612. Spot lensing 1608 is designed and configured to project individual spots of light, here, two spots 1616(1) and 1616(2) of light 1620(1) and 1620(2), onto chemical indicator disc 816 (i.e., the target), wherein each spot projected is based on light emitted from a corresponding light source, here, light sources 1624(1) and 1624(2), respectively. In a particular embodiment described below in connection with FIGS. 25 and 26, spot lensing similar to lensing 1608 is used to project four spots of light onto the corresponding chemical indicator apparatus, two spots for reflectivity measurements and two spots for fluorescence or absorbance measurements.

Figure 17:
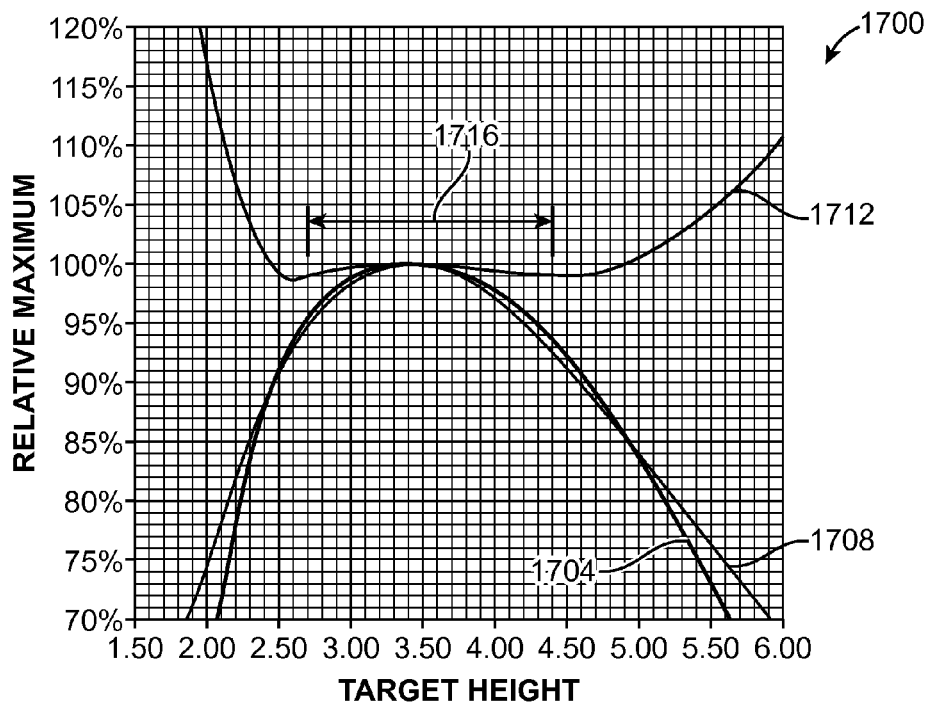
FIG. 17 is an exemplary graph of relative maximum reading intensity versus target height for the combined I/LC of FIG. 16.

In one implementation spot lensing 1608 is carefully designed and configured in conjunction with the spacing, S, between combined I/LC 1600 and the surface 1626 of disc 816 to provide highly precisely sized and located spots 1616(1) and 1616(2). As seen in FIG. 16, spot lensing 1608 is designed and configured so that light 1620(1) and 1620(2) passing by a principal point at spot lensing converges at a focal point 1628 that is located at a distance beyond the target (chemical indicator disc 816) so that the light forms the two individual spots 1616(1) and 1616(2) on the target. In one example, wherein spacing S is about 3.5 mm, the focal distance F to focal point 1628 is about 7.8 mm. In addition, it is noted that spot lensing 1608 is further designed to provide very little to no variance in measurements acquired over a relatively wide range of spacing S. In other words, the amount of light collected by combined I/LC 1600 remains largely unchanged despite spacing S varying due to wobble and/or other factors. This is illustrated, for example, in the graph 1700 of FIG. 17, which shows that there is no more than about 1% variance in measurements over a range of almost 2.0 mm. In graph 1700 of FIG. 17, curve 1704 represents the detected intensity, as a percentage of the maximum intensity, of an illumination spot formed by a combined I/LC similar to combined I/LC 1600 of FIG. 16 using a red LED input. Curve 1708 is a similar curve, but for fluorescent light detected from a spot illuminated using a light of an appropriate excitation wavelength for the particular chemical indicator used. Curve 1712 represents the ratio of (R/Rm)/(F/Fm) where R is reflectivity reading and Rm is maximum Reflectivity reading, F is fluorescence reading and Fm is maximum fluorescence reading. As can be seen from graph 1700, curve 1712 reveals that no more than about 1% variation in intensity occurs over a range 1716 of almost 2.0 mm when using this ratiometric correction step. It should be noted that any number of different wavelengths of light could be used to create this reflectance signal used for correction.

Referring again to FIG. 16, the relative wide range distance S having low intensity variation can be important to the quality of results provided by monitoring unit 812 when there is variance in distance S from reading to reading, for example, due to things like wobble of disc 816 due to movement of water 804, such as from a wave generator, fish swimming by, etc. In addition, it is noted that the relatively wide range of allowable error for spacing S allows a designer to carefully choose the size of illumination spots 1616(1) and 1616(2) to control the amount of photo-aging of the particular chemical indicator at issue. Photo-aging of chemical indicators is addressed below in more detail, but generally, the lower the brightness of the illumination, the slower the photo-aging. Thus, by making illumination spots 1616(1) and 1616(2) relatively large, the intensity of the brightness at any location within that spot is lower than if the same light 1620(1) and 1620(2) were used to form a smaller spot, which would be of greater brightness intensity. That would be the case if the target (disc 816) were moved closer to focal point 1628, thereby increasing spacing S. That said, over a certain optimal range, despite differences in spacing S, largely the same amount of light is collected from a more-intense smaller spot as is collected from a less-intense larger spot. When spacing S is selected to be in this optimal range, substantial immunity to negative effects of disc wobble and other inaccuracies in spacing S and minimizing photo-aging can be readily accounted for.

Figure 15:
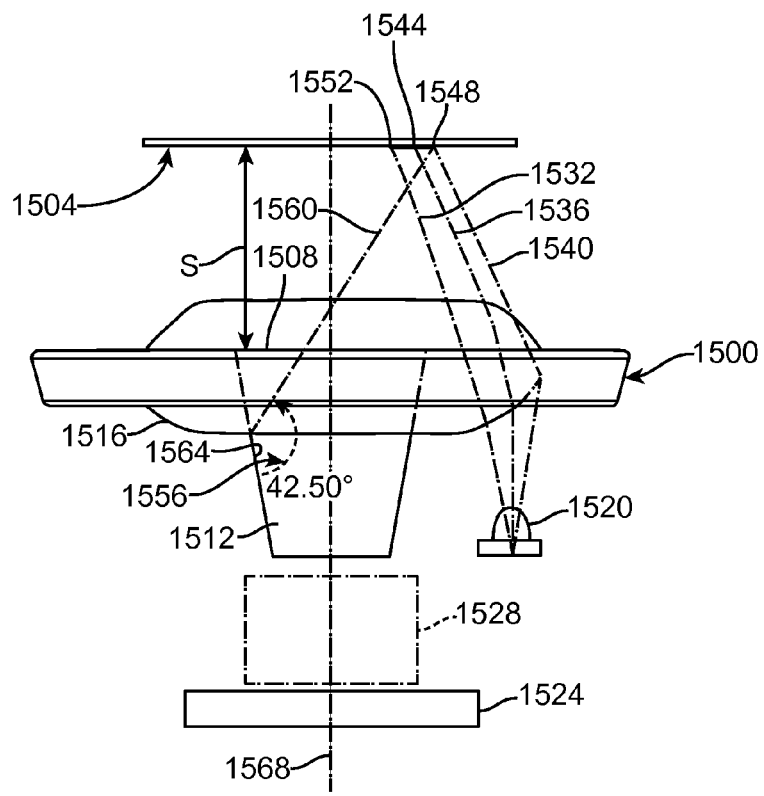
FIG. 15 is a diagram illustrating design considerations that can be used to design a combined I/LC of the present disclosure.

FIG. 15 is a diagram illustrating considerations that can be used to design a combined I/LC of the present disclosure. As seen in FIG. 15, which illustrates an I/LC 1500 and a target 1504 spaced from the I/LC by distance (spacing) S to an upper portion 1508 of a light collector 1512 that collects light from the target in the manner described above relative to I/LC 1604 of FIG. 16. FIG. 15 also illustrates spot lensing 1516 of I/LC 1500, a light source 1520, a light detector 1524, and an optional light filter 1528. It is noted that each of light source 1520, light detector 1524, and filter 1528 can be the same as or similar to any of the like items described herein. As seen in FIG. 15, the light emitted by light source 1520 is represented by three rays 1532, 1536, and 1540, which represent, respectively, the inside half-brightness flux line, the full brightness flux line, and the outside half-brightness flux line. The light from light source 1520 that is directed onto target 1504 by spot lensing 1516 forms a spot 1544 of light having points 1548 and 1552 that are the outside and inside half-brightness points, respectively. An angle 1556 is the critical angle for the interface of the material of light collector 1512 and air (which here laterally surrounds the light collector). In the present example wherein light collector 1512 is made of acrylic, critical angle 1556 is 42.5°. The ray 1560 leading to critical angle 1556 indicates the angle that is the minimum for the light to be reflected onto detector 1524. Any ray that is less than critical angle 1556 will pass through the side wall 1564 of light collector 1512 and will not reach the detector.

As distance S is increased, the quantity of rays emanating from between outside half-angle point 1548 and inside half-angle point 1552 of spot 1544 that will exceed critical angle 1556 such that they will be directed onto detector 1524 goes up. When the distance S increases, the distance from target 1504 to the aperture formed by the internal TIR center column also increases and therefore results in a reduction of intensity as a function of $1/S^2$. So by balancing the rate in which the rays become less intense due to distance with the rate at which the rays start passing through the sides of light collector 1512 at less than critical angle 1556, a peak detection point can be formed at a desired height with spots 1544 at useful distances from the centerline 1568 of I/LC 1500. By adjusting the angle of sidewalls 1564 of light collector 1512 relative to centerline 1568, distance S at which the peak light collection occurs can be tuned. The rate at which the light falls off as a functions of distance S change can also be tuned by way of changing whether rays inside and outside half-brightness rays 1532 and 1540 are divergent or convergent as they leave spot lensing 1516 of I/LC 1500. This effectively defines a band of useful operation.

Referring again to FIG. 16, spot lensing 1608 includes a light-entrance surface 1632 that has a high curvature due to the interface of the material of body 1604 with air between light sources 1624(1) and 1624(2) and the need to impart a significant amount of refraction into light 1620(1) and 1620(2) as it proceeds through the spot lensing. In this example, this need is relatively great because the output surface 1636 of spot lensing 1608 interfaces with water, which will typically have an index of refraction that is relatively close to the index of refraction of the material of body 1604 such that little refraction is achievable at surface 1636 without exceedingly drastic curvatures that interfere with other functionality of combined I/LC 1600. It is noted that spot lensing 1608 can be continuous around central light pipe 1612, or not. As an example of the latter, spot lensing 1608 can be notched so that lensing is present only at each light source 1624(1) and 1624(2) and not present therebetween. It is also noted that spot lensing can be provided with one or more contour features at and/or adjacent output surface 1636 that inhibits internal reflection, both partial and total, back into light pipe 1612. Indeed, in the example shown, the curvature at output surface 1636 is configured to direct light coming from light source 1624(2) to pass overtop of light pipe 1612 into spot lensing 1608 on the other side of the light pipe so that it outputs through light-entrance surface 1632 for the opposite light source 1624(1), thereby keeping the stray light from reaching the light pipe and, ultimately, sensor 1660.

In this embodiment, combined I/LC 1600 includes optional laterally dispersive lensing 1640 that acts to direct portions 1644(1) and 1644(2) of the light 1620(1) and 1620(2), respectively, emitted from light sources 1624(1) and 1624(2) away from spots 1616(1) and 1616(2). Directing portions 1644(1) and 1644(2) away from spots 1616(1) and 1616(2), and more generally from the region where light is to be collected by combined I/LC 1600, those portion do not interfere with the readings taken by a reader system, such as reader system 400 of FIG. 4. Those skilled in the art will readily understand how to design laterally dispersive lensing 1640.

Each light source 1624(1) and 1624(2) can be any suitable source, including filtered and unfiltered monochromatic and multiband light-emitting diodes (LEDs), filtered and unfiltered monochromatic and multiband lasers, filtered and unfiltered incandescent sources, filtered and unfiltered optic fiber(s) in optical communication with a light emitter, etc. Those skilled in the art will understand how to select the proper light source(s) and any optical filter(s) necessary to achieve the desired results. Some examples of specific light sources are described below.

As for the light collection aspect, combined I/LC 1600 includes central light pipe 1612 that collects light 1648(1) and 1648(2) from the regions of spots 1616(1) and 1616(2), respectively. As should be apparent from the foregoing discussion, light 1648(1) and 1648(2) can be reflected light from spots 1616(1) and 1616(2) or fluorescent light resulting from the stimulation of any fluorescent dye, for example, from any one of chemical indicator patches 1004(1) to 1004(10) (FIG. 10) that includes such dye, from spots 1616(1) and 1616(2), or a combination of both. Central light pipe 1612 include an input end 1652 proximate to chemical indicator disc 816 (when present) and an output end 1656 that directs light 1648(1) and 1648(2) toward one or more suitable sensors 1660, which may or may not be located downstream of one or more optional light filters 1664, depending on the sensitivity(ies) of the sensor(s) provided. For example, for a fluorescing dye, it is typically desirable to measure (sense) only the fluorescent light, i.e., without any reflected stimulating light. If the sensor 1660 at issue is a broadband sensor, then it would be desirable to provide one or more filters 1664 that filter out the original stimulating light. Alternatively, if the sensor 1660 at issue is sensitive only to the fluorescent light, then a filter is not needed. It is noted that light pipe 1612 can have any length desired. In such cases, any losses can be accounted for. In this connection, in some embodiments light pipe 1612 can be segmentized, as long as the segments are properly optically coupled. It should also be noted that filters such as evaporated coating dielectric layer filters and other types can be coated onto output end 1656 and become an integral part of the I/LC.

Light pipe 1612 and combined I/LC 1600 more generally include several features to ensure that the light 1648(1) and 1648(2) collected by the light pipe and directed toward sensor(s) 1660 is substantially only light from the target, i.e., chemical indicator disc 816. These features include: the separation of light pipe 1612 from spot lensing 1608 along a portion of the light pipe; the design (curvatures) of entrance and output surfaces 1632 and 1636, respectively, that inhibits internal reflection from spot lensing into light pipe within body 1604; the provision of laterally dispersive lensing 1640; and the design of lateral surface 1668 of the spot lensing that also help inhibit internal reflections from reaching the light pipe. Sensor 1660 can be a surface mounted detector on the bottom side of a printed circuit board (PCB) with a sensing area that collects light through a hole in the PCB. Light sources 1624(1) and 1624(2) can also be surfaces mounted but on the opposite side of the PCB from sensor 1660. This arrangement permits the use of the PCB material to act as a light block for making sure light that is internally scattered from light sources 1624(1) and 1624(2) can't make direct optical path to sensor 1660.

In the example shown, each light source 1624(1) and 1624(2) comprises a lensed LED package and is located in close proximity to light-entrance surface 1632 of spot lensing 1608. In one example, each light source 1624(1) and 1624(2) output light having a beam angle β of about 10° to about 30°. As used herein and in the appended claims, the term "beam angle" shall mean the angle between the two directions opposed to each other over the beam axis for which the luminous intensity is half that of the maximum luminous intensity of the output of the light source at issue. Depending on the configuration of the reader of which combined I/LC 1600 is part, light sources 1624(1) and 1624(2) can have the same output wavelength(s), or, alternatively, the respective output wavelength(s) can differ from one another. This will become apparent with an exemplary embodiment described below that has four light sources per reader, two light sources for measurement purposes (e.g., either fluorescence or absorbance) and two light sources for determining whether or not there are any contaminants on the target (disc 816) where measurement readings are being taken that might interfere with the resulting measurements. In addition, it is noted that depending on the spectral output of each light source 1624(1) and 1624(2), one, the other, or both can be provided with one or more light filters 1672(1) and 1672(2), respectively, as needed to suit the needs of use.

Figure 18:
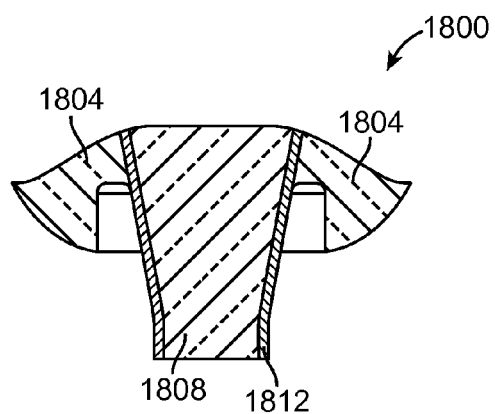
FIG. 18 is an alternative combined I/LC that is an assembly of separately manufactured parts.

Whereas FIG. 16 illustrates a an example in which combined I/LC 1600 is made in a unitary monolithic manner, FIG. 18 illustrates an alternative combined I/LC 1800 that is an assembly of multiple separately manufactured parts. Like combined I/LC 1600 of FIG. 16, combined I/LC 1800 of FIG. 18 includes spot lensing 1804 and a central light pipe 1808, each having the same functionality described above for like portions of combined I/LC 1600 of FIG. 16. However, in FIG. 18, light pipe 1808 is formed as a separate component relative to spot lensing 1804. The two components, i.e., light pipe 1808 and spot lensing 1804 are held together, for example, by press fit, with an intermediate sleeve 1812 that separates the light pipe and spot lensing. Intermediate sleeve 1812 is made of any suitable material, such as an opaque material, highly reflective (e.g., mirror-like) material, or a material having an index of refraction suitably different from the materials of light pipe 1808 and spot lensing 1804 such that light internal to each of the light pipe and spot lensing is inhibited from reaching the other component. It is noted that in this example, laterally dispersive lensing (e.g., like laterally dispersive lensing 1640 of combined I/LC 1600 of FIG. 16) is not present. However, in alternative embodiments it can be provided, for example, in a unitary monolithic manner with spot lensing 1804.

FIG. 19 illustrates an alternative chemical indicator disc 1900 that can be used, for example, with monitoring unit 812 (see, e.g., FIG. 9). Disc 1900 is similar to disc 816 (FIG. 9) except that it includes a cleaning element 1904 designed, located, and configured to clean optical reader ports 908(1) and 908(2) (FIG. 9) of monitoring unit 812. As will be appreciated, optical reader ports 908(1) and 908(2) are susceptible to fouling, for example, from bubbles and/or buildup of matter from water 804 (FIG. 8), such as small particles, and/or algae, etc. When disc 1900 is mounted to monitoring unit 812 (FIG. 9), as the monitoring unit turns the disc during operations, cleaning element 1904 intermittently sweeps over optical port 908(1) and 908(2) and thereby cleans the corresponding surfaces, for example, output surface 1636 of spot lensing 1608 and input end 1652 of light pipe 1612 of combined I/LC00 of FIG. 16.

Figure 20:
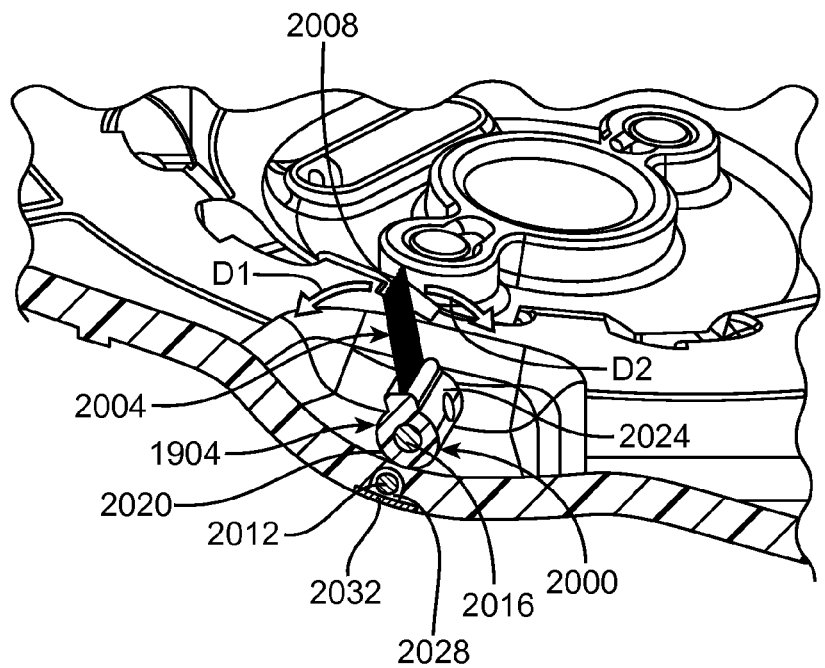
FIG. 20 is an enlarged partial cross-sectional view of the cleaning element of FIG. 19.

Referring again to FIG. 19, although cleaning element 1904 can be provided at any suitable location, in this example it is provided in place of one of the chemical indicator locations, of which there are eleven such locations 1908(1) to 1908(11) on this particular disc. Cleaning element 1904 resides in a recess 1912 formed within holder 1916 of disc 1900. As better seen in FIG. 20, in the embodiment shown cleaning element 1904 comprises a base 2000 and a plurality of bristles 2004 fixedly secured to the base. Cleaning element 1904 is biased into a position in which bristles 2004 are substantially perpendicular to the general plane of chemical indicator disc 1900. However, the biasing has a spring-like action that allows cleaning element 1904 to pivot in either direction D1 or D2 when the outstanding tips 2008 of bristles 2004 contact a structure, such as combined I/LC 1600 of FIG. 16 when positioned in one of optical reader ports 908(1) and 908(2), while disc 1900 is being rotated.

In the embodiment shown, this biasing action is provided by magnetic attraction, in this example a pair of magnets 2012 and 2016, one located in base 2000 of cleaning element 1904 and the other located on holder 1916. It is noted that while a pair of magnets 2012 and 2016 is illustrated, the magnetic attraction can be implemented in another way, such as between a single magnet and a ferromagnetic material or between more than one magnet in/on base 2000 and in/on holder 1916. As those skilled in the art will understand, the mutual attraction of magnets 2012 and 2016 to one another along with the specially curved rocking surface 2020 of base 2000, allows cleaning element 1904 to effectively rock on rocking surface 2020 in response to forces encountered at bristle tips 2008. The strengths of magnets 2012 and 2016 and the curvature of rocking surface 2020 can be varied to vary the pivoting (rocking) response and cleaning effectiveness of cleaning element 1904. Magnets 2012 and 2016 can ideally be diamagnetic types which are attracted on the sides vs. the ends of their rod shape. This diamagnetic attraction and magnetic pole alignment also provides for some of the return spring-like effect when deflected in either direction D1 or D2. In one example, base 2000 can be made of a plastic portion 2024 that is molded around magnet 2016. Magnet 2012 can be inserted into a suitable recess 2028 formed in the "back" side of holder 1916. Such insertion can involve, for example, an adhesive, a press fit or an interference fit, and/or the insertion can be followed by application of a closure 2032 to keep magnet 2012 in its place when magnet 2016 (i.e., cleaning element 1904) is not present.

While cleaning element 1904 is shown as a brush-based element, it can be of another type. For example, bristles 2004 can be replaced by another type of cleaning means, such as a sponge, squeegee, cloth, rubber-fingered, etc., cleaning mean. In addition, it is noted that while the biasing means is provided by magnetic attraction, it can be provided in another manner. For example, cleaning element 1904 can be modified so that magnet 2012 is a central shaft that is rotatable mounted to holder 1916, and the biasing can be provided using a suitable spring means, such as one or more torsional springs, one or more spiral springs, one or more coil springs, one or more resilient bumpers, among others, and any combination thereof. In yet another embodiment, base 2000 can be fixed to holder 1916 and bristles 2004 can be made sufficiently flexible and resilient so that they flex a predetermined amount when they swipe over any protruding optical element, such as combined I/LC 1332 (FIG. 13), at either of optical reader ports 908(1) and 908(2) (FIG. 9).

Figure 21:
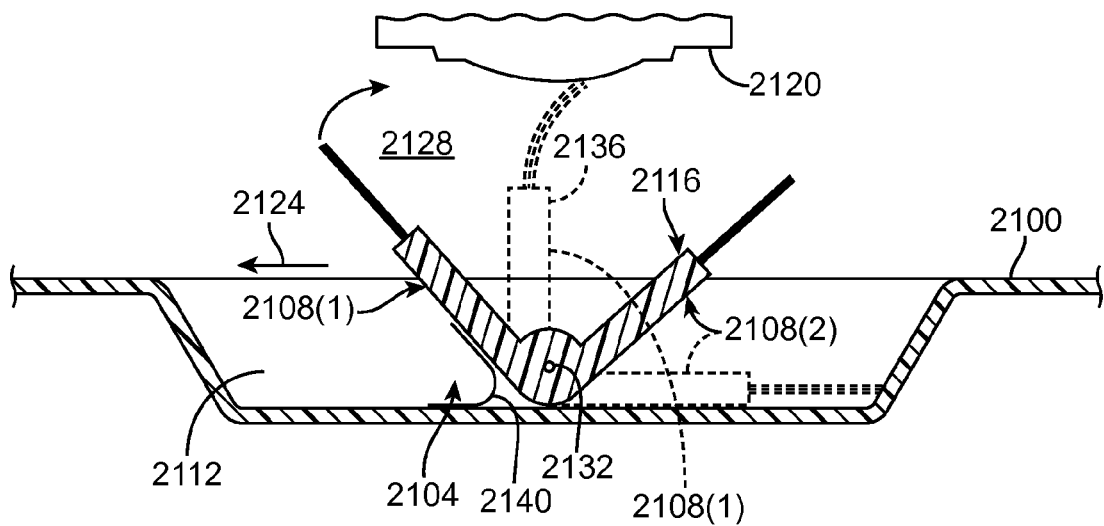
FIG. 21 is a partial cross-sectional view of another cleaning element that can be used with a chemical indicator apparatus for cleaning one or more components of a water quality monitoring/measuring unit.

Depending on the configuration of monitoring unit 812 (FIG. 8), it can drive the chemical indicator disc that is engaged with it, such as disc 816, continuously at relatively fast speeds. As mentioned above, this can be desirable for causing the water between the disc and monitoring unit 812 to be exchanged relatively rapidly. This relatively fast rotation can be leveraged for cleaning one or more optical reader ports, such as either of ports 908(1) and 908(2) of FIG. 9. In the embodiment shown in FIG. 21, a chemical indicator disc 2100 can be fitted with a cleaning element 2104 that is activated by spinning disc 2100 relatively rapidly. While FIG. 21 illustrates cleaning element 2104 as having a pair of brushes 2108(1) and 2108(2), it is noted that it can have more or fewer brushes. In one alternative, the cleaning element can have a single brush. In such case, the single brush can be deployed to a cleaning position only by move disc 2100 in one direction, but not the other. It is also noted that each brush 2108(1) and 21(2) can be replaced with a different type of cleaning device, such as a sponge, squeegee, etc. Cleaning element 2104 is pivotably mounted within a recess 2112 formed in disc 2100 and has a neutral position 2116 during normal monitoring operations when the disc is moved relatively slowly and/or in relatively small increments. The pivotability of cleaning element 2104 can be provided in any of a number of manners, such as using a magnetic attachment (such as the magnetic attachment illustrated above in FIGS. 19 and 20 in connection with cleaning element 1904), an axle arrangement, and an end-pin/rotational bearing arrangement, among others. As can be seen, when cleaning element 2104 is in its neutral position 2116, brushes 2108(1) and 2108(2) do not contact reader optic 2120. However, during rapid rotation of disc 2100 to the left as illustrated at arrow 2124, the resistance of the water in the space 2128 between disc 2100 and reader optic 2120 on brush 2108(1) causes brush 2108(1) to deploy, by pivoting about axis 2132, into an outstanding cleaning position 2136 in which it contacts the optical port, thereby cleaning the port. Cleaning element 2104 shown is a bi-directionally operative cleaning element, meaning that when disc 2100 is rotated in the direction opposite direction 2124, then the cleaning element would pivot in the opposite direction, meaning that brush 2108(2) would be outstanding instead of brush 2108(1) in its cleaning position 2136. In the example shown, cleaning element 2104 is biased into its neutral position 2116 using any suitable biasing means, such as a spring element 2140, which is configured to allow the cleaning element to pivot in both directions relative to its neutral position, one of which, i.e., cleaning position 2136, is illustrated in FIG. 21. Alternatively diamagnetic magnet pairs such as in FIG. 20 can also return cleaning element 2104 back to neutral position.

Figure 22:
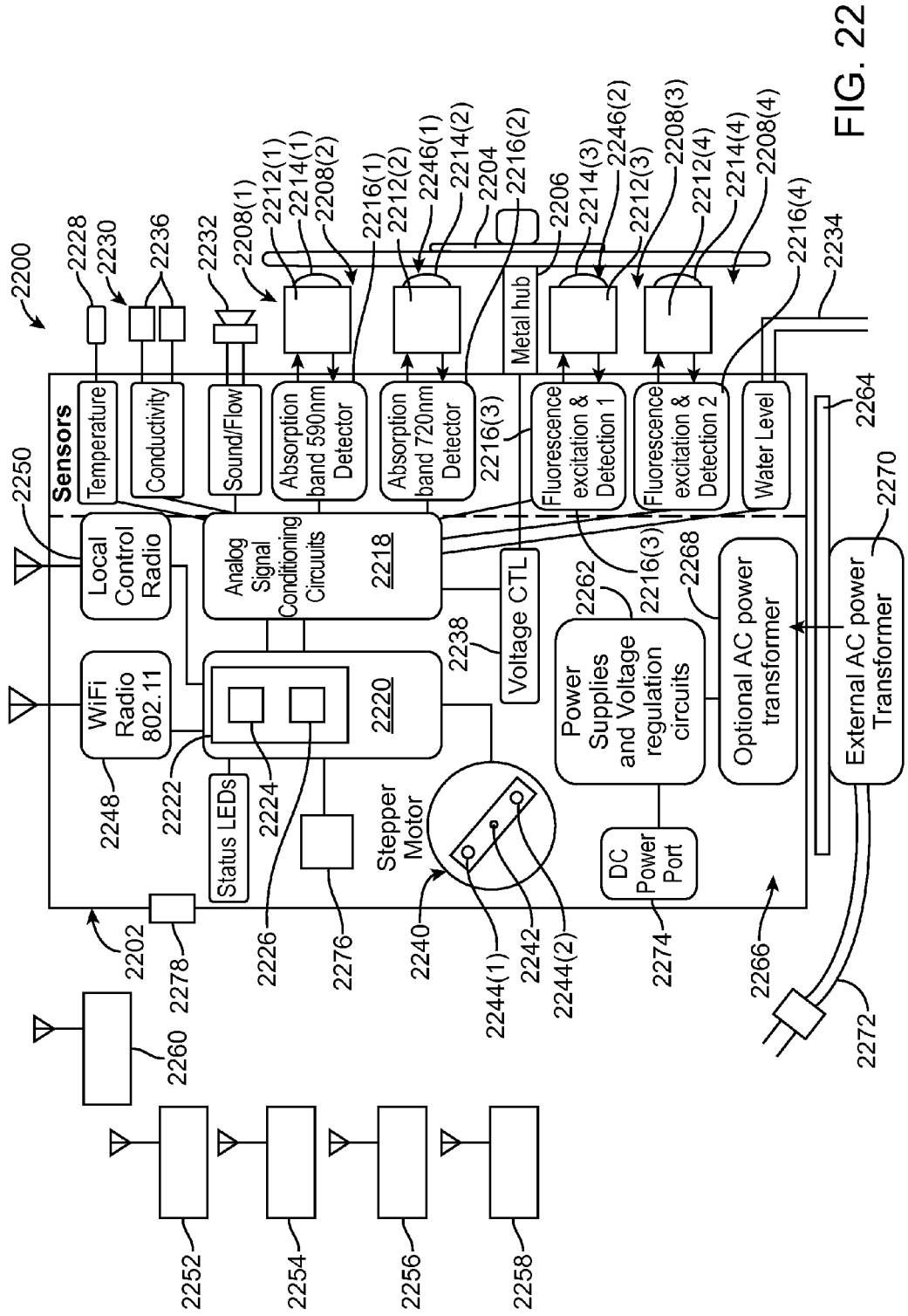
FIG. 22 is a schematic/block diagram illustrating various components of the monitoring system of FIG. 8.

FIG. 22 illustrates a water quality monitoring unit/chemical indicator disc system 2200 that includes a monitoring unit 2202 and a chemical indicator disc 2204 engaged with the monitoring unit. Monitoring unit 2202 and disc 2204 can be embodied, respectively, as monitoring unit 812 and chemical indicator disc 816 and, therefore, have any of the functionality of those components that is described above. For brevity, those functionalities will not be re-described relative to system 2200 and only some are mentioned in this description of FIG. 22. However, the reader should understand that any unmentioned functionalities and/or any un-described details are indeed present in system 2200 and reference can be made to the foregoing description should further information be needed or desired. Disc 2204 is rotatably engaged with monitoring unit 2202 via an electrically conductive receiver 2206 so that electrical charge can be conveyed to the disc for the reasons noted above.

Monitoring unit 2202 includes four optical readers 2208(1) to 2208(4) for reading the chemical indicators (not shown) present on chemical indicator disc 2204. In this example: optical reader 2208(1) is designed and configured for illuminating and detecting absorbance at 590 nm wavelength; optical reader 2208(2) is designed and configured for illuminating and detecting absorbance at 720 nm wavelength; optical reader 2208(3) is designed and configured for exciting and detecting fluorescence; and optical reader 2208(4) is also designed and configured for exciting and detecting fluorescence. Each of optical readers 2208(1) to 2208(4) includes an optical assembly 2212(1) to 2212(4) that includes one or more suitable light sources (not shown), one or more suitable light sensors (not shown), and a combined I/LC 2214(1) to 2214(4). Optical reader 2208(1) has illumination and detection circuitry 2216(1) designed and configured to send driving signals to, and receive detected signals from, optical assembly 2212(1); optical reader 2208(2) has illumination and detection circuitry 2216(2) designed and configured to send driving signals to, and receive detected signals from, optical assembly 2212(2); optical reader 2208(3) has excitation and detection circuitry 2216(3) designed and configured to send driving signals to, and receive detected signals from, optical assembly 2212(3); and optical reader 2208(4) has excitation and detection circuitry 2216(4) designed and configured to send driving signals to, and receive detected signals from, optical assembly 2212(4). In this embodiment, each of illumination/excitation and detection circuitries 2216(1) to 2216(4) is analog circuitry that is in operative communication with analog signal conditioning circuitry 2218, which in turn is controlled by a processing system 2220 that controls virtually all operations of system 2200, including data processing.

Processing system 2220 may include one or more microprocessors, microcontrollers, central processing units, etc., or any logical combination thereof. There are fundamentally no limitations on how processing system 2220 can be embodied, including centralized processing architectures and distributed processing arrangements. Processing system 2220 includes one or more memories, collectively represented by memory 2222, used to store (transitorily and/or non-transitorily, depending on type) machine-executable instructions 2224, data 2226, and other digital information that allows processing system to control the operation of system 2200. Examples of memories that can be aboard monitoring unit 2202 include, but are not limited to, hardware storage memory (removable or non-removable), random-access memory, and cache memory, among others. In addition, memory can be of any suitable type, including transistor based, magnetic, optical, etc. Fundamentally, there is no limit on the nature and type of memory that can be used in processing system R20.

In addition to optical readers 2208(1) to 2208(4), monitoring unit 2202 includes other sensors/detectors. These include: 1) a temperature sensor 2228; 2) a conductivity sensor 2230; 3) a sound detector 2232; and 4) a water level detector 2234, each of which in this embodiment is in operative communication with analog signal conditioning circuitry 2218. It is noted that in other embodiments, some or all of analog signal conditioning circuitry 2218 may not be needed if the outputs (and/or inputs) of the various sensors, detectors, and readers are digital. Temperature sensor 2228 is provided for measuring the temperature of the water (such as water 804 in FIG. 8) in which monitoring unit 2104 is fully or partially submerged so that monitoring unit 2202 can estimate the temperature of the chemical indicators on the chemical indicator apparatus that is engaged with the monitoring unit. Temperature compensation can be a very important aspect for ensuring monitoring unit 2202 is outputting meaningful information based on readings taken by optical readers 2208(1) to 2208(4). For example, some chemical indicators are relatively sensitive to temperature, whereas others are not. In addition to monitoring unit 2202 being programmed (see, e.g., software (machine-executable instructions 2224)) to adjust reading data based on the temperature of the chemical indicators, the monitoring unit can also be programmed to make adjustments to compensate for the varying performance of light sources due to temperature changes and/or to compensate for detector performance variation due to temperature changes. In this connection, though not shown, the circuit board(s) on which the light sources and/or detectors are mounted can include one or more temperature sensors for measuring the temperature of the light sources and detectors. Relative to chemical indicator temperature, it is noted that a chemical indicator apparatus of the present disclosure, such as chemical indicator disc 816 of FIGS. 8 and 9, could be provided with a color changing temperature indicator that changes color depending on its temperature. Correspondingly, for example, one of optical readers 2208(1) to 2208(4) could be configured to determine the color of the temperature indicator. Monitoring unit 2202 could then use the determined color to determine the temperature of disc 816 and use that temperature to make the corrections noted above. A benefit to using a color changing temperature indicator on the chemical indicator apparatus is that the temperature is read from the disc itself. In addition, the accuracy of water contacting temperature probes can be affected by the flow of the water.

Referring again to FIG. 22, conductivity sensor 2230 may consist of a pair of spaced electrodes 2236 that contact the water in which disc 2204 is submerged to allow the monitoring unit to measure the conductivity of that water. As those skilled in the art will understand, a conductivity measurement made using conductivity sensor 2230 can be used to infer the presence of various constituents within the water. Sound detector 2232 can be provided to detect the operating state (on, off, speed, etc.) of any water pumps, wave generators, and/or other device(s) that produce one or more detectable sounds/vibrations when operating. Knowing the operating state(s) of such one or more devices allows, for example, monitoring unit 2202 to use that information to control its own operation, such as the operation of any one or more of optical reader(s) 2208(1) to 2208(4), to allow a user to remotely listen to the operation of her/his aquarium equipment, and/or to issue an alert that one or more of the monitored devices is not functioning correctly, among other things. Water level detector 2234 can be provided for measuring the level of the water in container (not shown) in which monitoring unit 2202 is deployed, such as an aquarium container or sump. As those skilled in the art will appreciate, water level data can be used for controlling monitoring unit 2202 and/or any remote devices, such as a make-up water valve, and/or for determining whether or not to issue any alerts as to too high or too low of a water level.

Monitoring unit 2202 includes a voltage controller 2238 in electrical communication with analog signal conditioning circuitry 2218 for providing a voltage to conductive receiver 2206, which in turn provides the voltage to disc 2204 to provide one or more of the chemical indicators (not shown) onboard the disc with an enhanced range. Monitoring unit 2202 also includes a stepper motor 2240 that drives disc 2204 via magnetic coupling as described above in response to control input from processing system 2220. In this example, a magnet holder 2242, which supports magnets 2244(1) and 2244(2), is driven by motor 2240, and the magnetic interaction of magnets 2244(1) and 2244(2) with corresponding respective oppositely polarized magnets 2246(1) and 2246(2) on disc 2204 drives the corresponding rotation of the disc.

Monitoring unit 2202 includes first and second radios 2248 and 2250, respectively, controlled by processing system 2220. In the embodiment shown, first radio 2248 is provided for communicating with one or more local area network devices, for example, wireless TCP/IP router, radio-enabled smartphone, tablet computer, laptop computer, desktop computer, etc. First radio 2248 may be the primary communications device, for example, for receiving operating parameters from an off-monitor software application and for communicating measurement data, monitor status information, and other information, such as audio from sound detector 2232, to the external device(s), and/or to an off-monitor software application for receiving such information. In one embodiment, first radio 2248 is designed and configured to operate under any one or more of the IEEE 802.11 standards, but the radio can be designed and configured to work under any other suitable standard(s).

In this example, second radio 2250 is included to provide a small area network or piconet to allow monitoring unit 2202 to communicate with proximate external devices that are part of the overall aquatic-environment environmental control scheme. Examples of such external devices include, but are not limited to, one or more: lighting devices 2252 for providing light to the aquatic environment; chemical dosers 2254 for dispensing one or more chemicals to the aquatic environment; feeding devices 2256 for dispensing food to the aquatic environment; water pumps 2258 for circulating water within the aquatic environment; wave generators 2260 for generating waves within the aquatic environment; and power strips into which these and other devices are plugged. In one example, second radio 2250 is designed and configured to utilize BLUETOOTH® standards. However, second radio 2250 can be designed and configured to work under any other suitable standard(s). It should be noted that while two radios are shown, that a single radio which supports multiple modes and standards can also be used to provide both the proximate local communications and the network connectivity.

Monitoring unit 2202 includes power supply 2262 that provides conditioned power to other components and circuits onboard the monitoring unit. Power supply 2262 can include voltage regulation circuitry that provides a high-precision electrical reference, which can be very important for taking readings and/or driving the light sources. Other components of monitoring unit 2202 may include a suitable timing source, such as a crystal oscillator, for ensuring that timing throughout the system is precise, such as for controlling integration times of light detectors. In one embodiment, wherein monitoring unit 2202 is designed and configured to be located within a water container (represented by wall 2264 in FIG. 22), for example, aquarium sump, aquarium tank, filter tank, skimmer box, etc., that is part of the aquatic environment in which monitoring unit 2202 is deployed, power supply 2262 receives power through the wall of the container via an inductively coupled transformer system 2266. In this example, inductively coupled transformer system 2266 includes a first transformer component 2268 in electrical communication with power supply 2262 and a second transformer component 2270 in electrical communication with an external power source, such as a domestic power outlet (not shown) via a suitable power cord 2272. During use, one or more induction coils (not shown) within second transformer component 2270 induce electrical current to flow within one or more induction coils with first transformer component 2268 via magnetic coupling between the induction coils in the two components. In turn, first transformer component 2268 provides the resulting electrical energy to power supply 2262 to power monitoring unit 2202. Advantages of this magnetic coupling include the ability to avoid running a power cord into the water container and needing to create a liquid seal at any opening in monitoring unit 2202 needed to run such power cord into the unit. As those skilled in the art will understand, wall 2264 of the water container can be made of any non-magnetic material, such a plastic, glass, wood, non-magnetic composite, etc., and any combination thereof. Alternatively, or in addition, monitoring unit 2202 can include a power port, such as a low voltage DC power port 2274, that alternatively provides power to power supply 2262.

Monitoring unit 2202 may also include an accelerometer 2276, such as a 3-axis accelerometer. As discussed above relative to monitoring unit 812 of FIGS. 8 and 9, accelerometer 2276 can be used in a scenario in which monitoring unit 2202 can become disengaged from any structure it is engaged with to determine when that disengagement has occurred. If an abnormal acceleration is detected using accelerometer 2276, processing system 2220 can be programmed to issue a suitable alert to notify a user of the (possible) disengagement.

In some cases, when a monitoring unit made in accordance with the present disclosure is sealed for watertightness, pressure changes during shipping, such as shipping by air, can affect the precision alignments and/or positional tolerance of various critical components of the unit, such as components of the optical readers, such as light sources, optics, light detectors, etc. Large pressure differentials experienced during shipping can cause permanent deflections in various components, such as housing components that can affect reading accuracy of the unit. To combat this, a watertight monitoring unit, such as monitoring unit 2202 of FIG. 22, can be provided with a pressure equalization system that allows the pressure inside the unit to adjust to the pressure on the outside of the unit. In one example, a pressure equalization system includes a water-impermeable/air-permeable membrane 2278 that allows air to pass through for air-pressure equalization during shipping and can be left in place without any end-user interaction to keep monitoring unit 2202 watertight for use.

Figure 23:
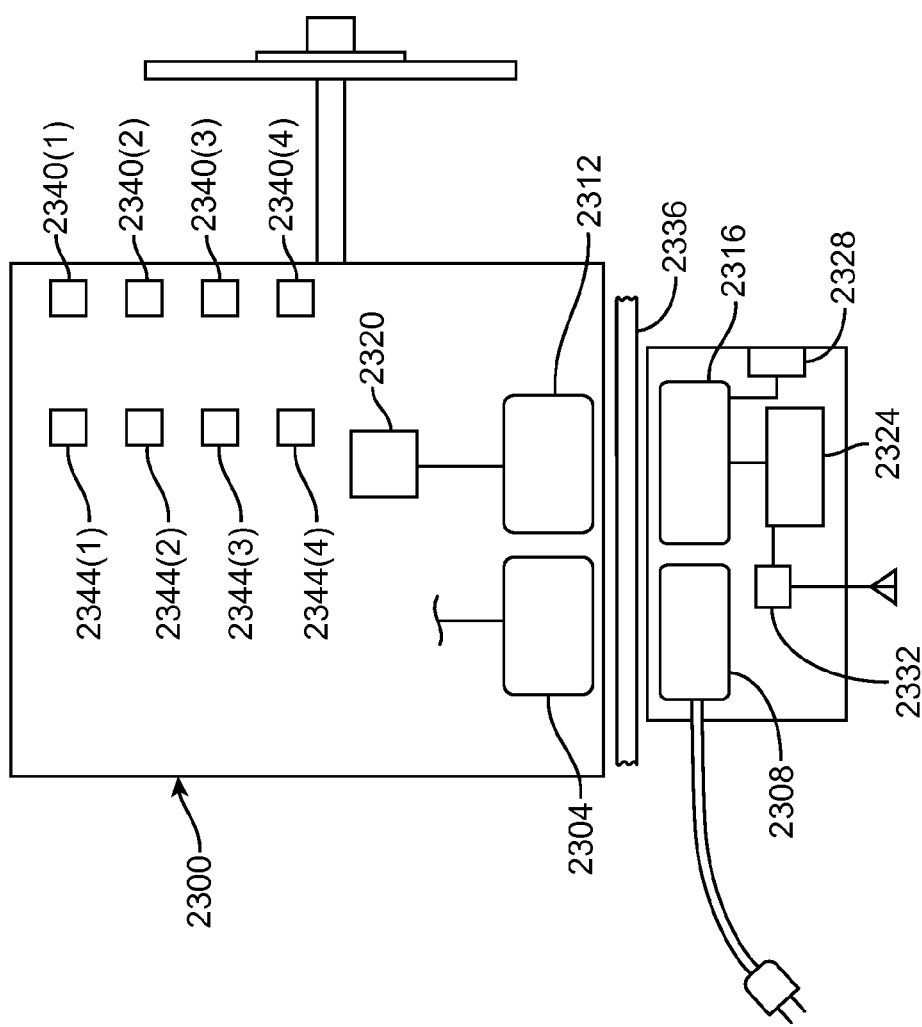
FIG. 23 is a schematic/block diagram illustrating a monitoring system having non-wired communication of power and data.

FIG. 23 illustrates a monitoring unit 2300 that is similar to monitoring unit 2202 of FIG. 22 in that it is designed to be at least partially submerged in the water that it is designed to monitor. However, in monitoring unit 2300 not only is power provided to the monitoring unit via inductive coupling of first and second transformer components 2304 and 2308, respectively, but data and other information is transmitted from and to monitoring unit via inductive coupling of first and second inductive digital couplers 2312 and 2316, respectively. First inductive digital coupler 2312 is operatively coupled to a suitable processing system 2320 that can perform largely the same functions as processing system 2220 of FIG. 22. Second inductive digital coupler 2316 can likewise communicate with a processing system 2324 that, in turn, can communicate with one or more communications devices 2328 and 2332, each of which can be, for example, a wired digital data port (such as a universal serial bus port, a FIREWIRE® port, etc.) or a radio (such as a BLUETOOTH® radio, a WIFI™ radio, etc.), among other things.

In alternative embodiments, processing system 2324 can be eliminated, with data and information from and to second inductive coupler 2316 being provided directly to the one or more communications devices 2328 and 2332 or an intermediary device(s) (not shown) other than processing system 2324. In various alternative embodiments, first and second inductive digital couplers 2312 and 2316 can be integrated into inductive transformer components 2304 and 2308 by suitably superimposing data signals on the power signals and using suitable encoders and decoders for the embedded signals as known in the art. In addition, in various other alternative embodiments, first and second inductive digital couplers 2312 and 2316 can be replaced by other suitable wireless data communications devices that can communicate data across wall 2336, such as very-near-range radio devices and optical devices, such as infrared transmitters, receivers, and/or transceivers, among other wireless data communications devices.

Depending on the intended deployment of monitoring unit 2300, locating communications device(s), here devices 2328 and 2332, outside of the water container (represented in FIG. 23 by wall 2336), can avoid transmission interferences, allow monitoring unit 2300 to be fully submerged at any depth, and allow the data communications to be wired without the need to run any wires into the container, among other advantages. It is noted that while processing system 2320 is shown as being inside the water container, it could alternatively be on the outside, effectively taking the place of processing system 2324. In those embodiments, the portion of monitoring "unit" on the inside of the water container would be largely only the optical reader 2340(1) to 2340(4) and various sensors/detectors 2344(1) to 2344(4) and their corresponding respective driving circuitries. Most or all processing and external communications would be performed outside the water container.

Figure 24:
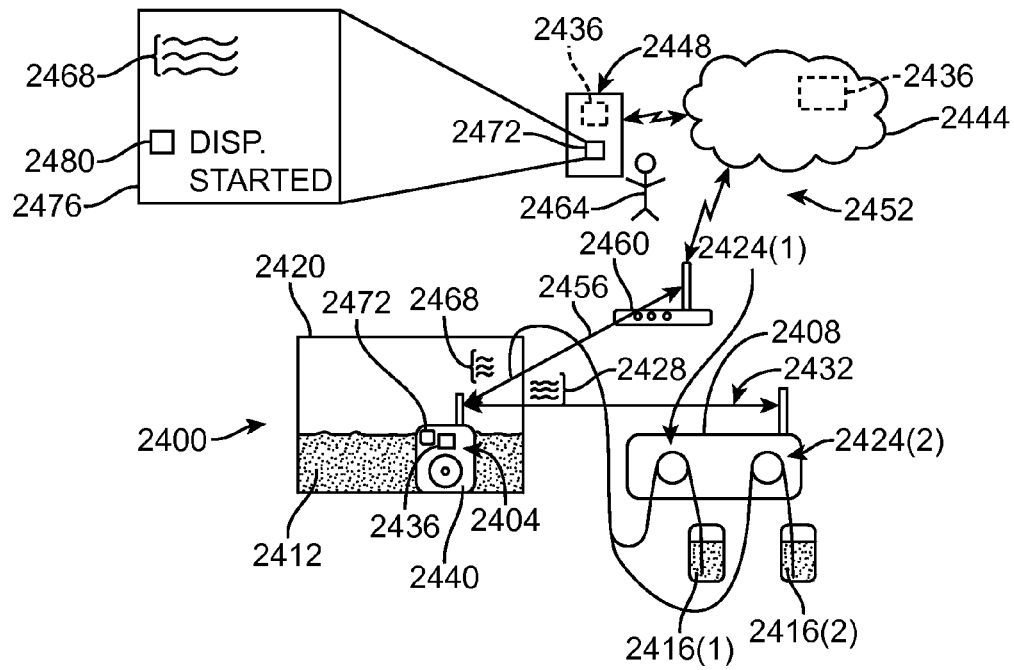
FIG. 24 is a schematic diagram of an aquarium setup having automated dosing functionality.

FIG. 24 illustrates an exemplary aquarium setup 2400 that includes an aquarium monitoring system 2404 and a doser 2408 for continually monitoring the quality of water 2412 and dispensing one or more appropriate additives to the water to keep the water quality within certain desired tolerances. Monitoring system 2404 can be, for example, a chemical-indicator-disc-based monitoring system that is the same as or similar to monitoring system 800 of FIG. 8. Doser 2408 can be any suitable doser that can be remotely or locally controlled to provide the dispensing of one or more chemicals and/or other additives, here two additives 2416(1) and 2416(2), needed to keep the water 2412 within the aquatic environment, here an aquarium 2420, within certain desired quality tolerances. In this example, doser 2408 includes a dispensing mechanism 2424(1) and 2424(2) for each of the two additives 2416(1) and 2416(2) to controllably dispense the corresponding additive. In this example, each dispensing mechanism 2424(1) and 2424(2) is a peristaltic pump that can be controlled to dispense highly precise amounts of liquid. In other embodiments, the doser can dispense more or fewer than two additives and can include any suitable type of dispensing mechanism(s) in addition to, or in lieu of, the peristaltic pumps illustrated.

In aquarium setup 2400, monitoring system 2404 can communicate automated dispensing instructions 2428 to doser 2408 via a piconet radio system 2432 in which the monitoring system and doser are provided with piconet radios (not shown) wherein there is at least one-way communication from the monitoring system to the doser. Alternatively, wired or other wireless communications may be used. To provide this functionality, monitoring system 2404 can be provided with a dosing calculator 2436 in which automated dispensing instructions 2428 are determined based on water quality measurements made by the monitoring system, for example, using any of the measuring and monitoring techniques described above. Dosing calculator 2436 can, for example, be located onboard a monitoring unit 2440 of monitoring system 2404, located off-board the monitoring unit, such as in a cloud-computing platform 2444 and/or on a computing device 2448 (such as a smartphone, tablet computer, laptop computer, desktop computer, etc.), or any combination of distributed functionality.

When monitoring system 2404 is configured to communicate with a local, wide, or global area network (such as, e.g., the Internet), it can be provided with a suitable communications system 2452 that allows it to communicate with the appropriate network or networks. In the present example, communications network 2452 includes a wireless connection 2456 between monitoring unit 2440 and a wireless router 2460, which itself is operatively connected to cloud-computing platform 2444. If some or all of dosing calculator 2436 is located remotely, such as on cloud-computing platform 2444 and/or a computing device 2448, automated dispensing instructions 2428 can be communicated to monitoring unit 2440 via communications network 2452, and the monitoring unit can relay the instructions to doser 2408. Alternatively, for example, if doser 2408 is outfitted so that it can communicate with wireless router 2460, the automated dosing instructions 2428 can be provided directly to the doser to avoid such relaying.

Alternatively, or in addition, to automated dosing, monitoring system 2400 can be configured to provide assisted dosing, i.e., configured to provide a person who maintains an aquarium (hereinafter "user" 2464) with assisted dosing instructions 2468. Dosing calculator 2436 can be configured to generate assisted dosing instructions 2468 along with, or in lieu of automated dosing instructions 2428. Monitoring system 2404 can provide assisted dosing instructions 2468 to any suitable computing device 2448 available to user 2464 and/or to a display 2472 on monitoring unit 2440 and/or a display on doser 2408. As those skilled in the art will readily appreciate, assisted dosing instructions 2468 can be in any suitable format, such as a tabular form that simply lists the additive and the amount to be added, a demand form, such as "Add 10 ml of pH increaser to sump while pump is running", or both, or any other type of instructions for the user to add the proper amount.

With either of assisted dosing and automated dosing, monitoring system 2404 can be configured to monitor water 2412 more frequently during dosing, such as to ensure that dosing is proceeding correctly. For example, with automated dosing, monitoring unit 2440 can switch to an "enhanced monitoring" mode in which the monitoring unit monitors continually for a predetermined period at short intervals once it has sent automated dosing instructions 2428 to doser 2408. The period that monitoring unit 2440 performs enhanced monitoring can be determined as a function of the type of additive(s) being added and/or the amount of the additive(s) being added. The enhanced monitoring period can extend for a predetermined amount of time beyond dispensing as may be required for the water quality parameters of water 2412 to rebalance, settle, etc. following dosing. In addition, the particular chemical indicator(s) and/or other sensing (e.g., temperature sensing, conductivity sensing, etc.) that is performed during enhanced monitoring can be tailored to the particular additive(s) being added. For example, if only a particular additive is being added for a particular dosing, only one or more chemical indicators and/or other specific sensing needed to be done during the enhanced monitoring.

Enhanced monitoring during dosing can be performed completely in lieu of normal routine monitoring, i.e., routine monitoring is not performed, or the enhanced monitoring can be performed in addition to normal routine monitoring. If enhanced monitoring detects an abnormality, such as the wrong additive being dispensed, too much additive being dispensed, the additive being dispensed too quickly, or the additive not causing any change (perhaps indicating that the corresponding additive reservoir is empty or a hose is plugged, etc.), among others, monitoring system 2404 can, for example, take any necessary corrective measure (including dispensing an "antidote" additive, stopping dispensing, running diagnostics, etc.) and/or issue one or more suitable alerts to the user, among other things. In the case of assisted dosing, the user can signal monitoring system 2404 that it has begun dispensing using one or more suitable controls. For example, if assisted dosing instructions 2468 are being displayed on a smartphone (e.g., computing device 2448) and the instruction are, for example, being displayed using a software application, or "app," 2472 for interfacing with monitoring system 2404, then the app may display on a GUI 2476 on the smartphone a soft button 2480 or other control labeled "Dispensing Started", or the like. By user 2464 activating button 2480, monitoring system 2404 is notified to start operating in the enhanced monitoring mode. Depending on the type of additive being used and its effect(s) on water 2412, additional user interaction can be provided to GUI 2476. For example, GUI 2476 can be provided with a soft button 2480 or other control that user 2464 is instructed to actuate each time she/he has dispensed a certain amount of the additive into water 2412.

In order for dosing calculator 2436 to properly determine dosing instructions, for example, either automated dosing instructions 2428 or assisted dosing instructions 2468, or both, it may need to know one or more pieces of information about aquarium setup 2400 and about the additives being added. Examples of information that dosing calculator 2436 may need to know about aquarium setup 2400 includes the volume of water 2412 in the setup, the type of the water (e.g., fresh, brackish, salt, etc.), and the one or more species of aquatic life (e.g., fish, coral, plants, etc.) that aquarium 2420 is supporting, the number of each species, the approximate mass of any coral, other environmental information, and any combination thereof. Examples of information that dosing calculator 2436 may need to know about each additive include, but are not limited to, the form (e.g., powder, liquid, gel, etc.), a concentration of the additive, the chemistry of the additive, other additive data, and any combination thereof. In lieu of, or in supplement or complement to, providing information of this type, user 2464 may input into monitoring system 2404 brand and product identification information in any one or more of a number of ways, such as by keying in the information, making a selection from a list of choices, and scanning a product code (e.g., bar code, QR code etc.), among others. If a mechanical doser, such as doser 2408, is used either manually or especially automatically, dosing calculator 2436 may also need to know information about the doser, such as its dosing instruction set and other dosing parameters. Depending on the implementation of aquarium setup 2400, doser information can be provided to dosing calculator 2436 in any of a number of ways, including keyed entry, product code scanning, make and model selection from lists, data transfer via a network, etc. Those skilled in the art will understand the information that dosing calculator 2436 needs to provide proper dosing instructions, such as automated dosing instructions 2428 and assisted dosing instructions 2468.

Robustness Features

With the foregoing examples and operating principles in mind, following are a number of features that can be provided as desired to a water quality monitoring/measuring system/units, including any of the systems and units described in this disclosure and that would be evident in view of such description. These features can be broadly termed "robustness features" in that they enhance the robustness of the systems/monitors to which they are added. These robustness features include features for reducing the effect of bad measurements due to: 1) contamination of a chemical indicator; 2) aging of a chemical indicator; and 3) when a magnetically coupled chemical indicator apparatus is used, friction between the chemical indicator apparatus and the receiver on which the indicator is mounted. The robustness features also include protecting against overdosing and protecting against dosing too quickly (e.g., to protect certain species of life supported by a particular aquatic environment being monitored, to prevent precipitation or other chemical reaction, etc.). Each of these robustness features is described in this section. It is noted that each of these features need not necessarily be implemented in conjunction with any particular system or component of the present disclosure, but rather can be implemented separately so as to include only the necessary supporting features and elements.

Multi-Reading Fault Detection/Handling

Detection and/or handling of faults caused, for example, by one or more bad regions on a chemical indicator (such as a region where an indicator dye is lacking, damaged, or occluded by contamination) can be handled by acquiring multiple readings from a single chemical indicator. An example of a multi-reading fault detection/handling scheme is described in this section in connection with FIGS. 25 and 26.

Figure 25:
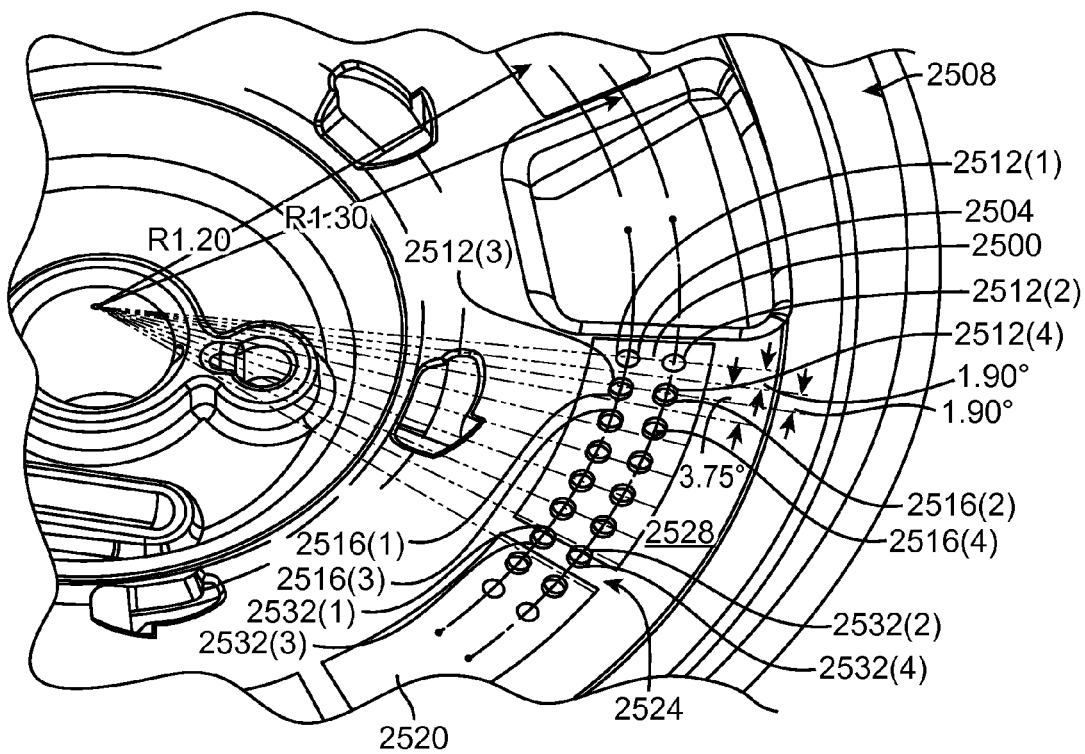
FIG. 25 is a partial perspective view of a chemical indicator disc, illustrating chemical indicators aboard the disc being read in a multi-reading mode.

FIG. 25 illustrates a chemical indicator 2500 from which multiple optical readings are taken. Each location that is illuminated and from which an optical reading is taken is indicated by a corresponding circle 2504. It is noted that chemical indicator 2500 can be any one of chemical indicators/chemical indicator patches described in examples above. In this connection, it is noted that while chemical indicator 2500 is depicted in FIG. 25 as residing on a discoidal chemical indicator apparatus 2508 such that the chemical indicator is arcuate, it is noted that the same or similar multi-reading scheme can be implemented on a chemical indicator of virtually any suitably sized and shaped area. As more fully described below, each circle 2504 approximates a spot of illumination light that is used to illuminate the corresponding region of chemical indicator 2500. Each illumination can be, for example, for fluorescence readings, absorbance readings, reflectance readings, and/or for reference purposes, for example, as described below in connection with reference illumination. It is noted that the number and locations of the spots of illumination in this example are merely illustrative and should not be considered limiting. Indeed, those skilled in the art will readily appreciate that there are many ways in which multi-reading fault detection can be implemented with differing patterns of illumination and/or differing locations of illumination, among other variables that can be changed from the illustrative example of FIG. 25.

As used in the following example, illumination for measurements (e.g., fluorescence readings and absorbance readings) are each referred to as "measurement illumination" as these illuminations are for taking measurements based on the chemical activity of the chemical dye(s) within chemical indicator 2500 in response to one or more constituent(s) of the water that the chemical indicator is designed for. On the other hand, illumination for determining the presence of contamination and/or other optical interferents (e.g., particulates in water) and conditions (e.g., improper distance between a reader and a chemical indicator being read) that affect indicator measurements (e.g., using reflectance readings) is referred to as "reference illumination," as this illumination is used as a reference to detect the presence of, for example, 1) any one or more contaminants on and/or in chemical indicator 2500 that may interfere with the fluorescence and/or absorbance of the chemical indicator, 2) an matter in the water located between a measurement reader and the chemical indicator that may affect the measurements being taken by the reader, and 3) any deviation of distance between a reader and the chemical indicator that may affect the measurements being taken by the reader, and any combination thereof. Examples of contaminants include, but are not limited to, surface contaminants such as algae and particulates, as well as physical defects/damage to chemical indicator 2500 itself, such as scratches and gouges. It has been found that many types of these and other contaminants tend to interfere with the reflectivity of a chemical indicator. Consequently, reflectivity readings and data taken from across a chemical indicator, such as chemical indicator 2500 can reveal where contamination may be present. Knowing this, and the fact that fluorescence and/or absorbance measurements taken at locations where contaminants are present, can allow a monitoring system/unit to determine whether or not a particular measurement reading is a trusted reading (i.e., one taken where contamination is likely not present as determined from the reference illumination and reading) or not a trusted reading (i.e., one taken where contamination is likely present). The monitoring system/unit can then be programmed to, for example, discard or treat with a lower weighting each non-trusted reading. In addition, taking multiple ones of each type of measurement reading on a single chemical indicator provides the ability to use statistics, such as averaging, to gain confidence in the measurements. Particular sets of these readings having particular usefulness are described below.

In addition to using averaging and/or trusted reading techniques on the measurement illumination spots, similar techniques can be used for the reference illumination spots. For example, an algorithm can be used to sort readings from each chemical indicator and pick the most common values. When the reading being taken from a reference illumination spot is based on reflectivity, contamination on the chemical indicator could cause more or less reflection. For example, calcium carbonate might start to leave a white film on a chemical indicator, which would cause the reflected light to be more intense. Regardless of whether the contamination causes a brighter or dimmer reflection, in one example only the most closely matched N readings are used for averaging and determining the measurement, and the remaining readings are discarded as being unreliable.

Figure 26:
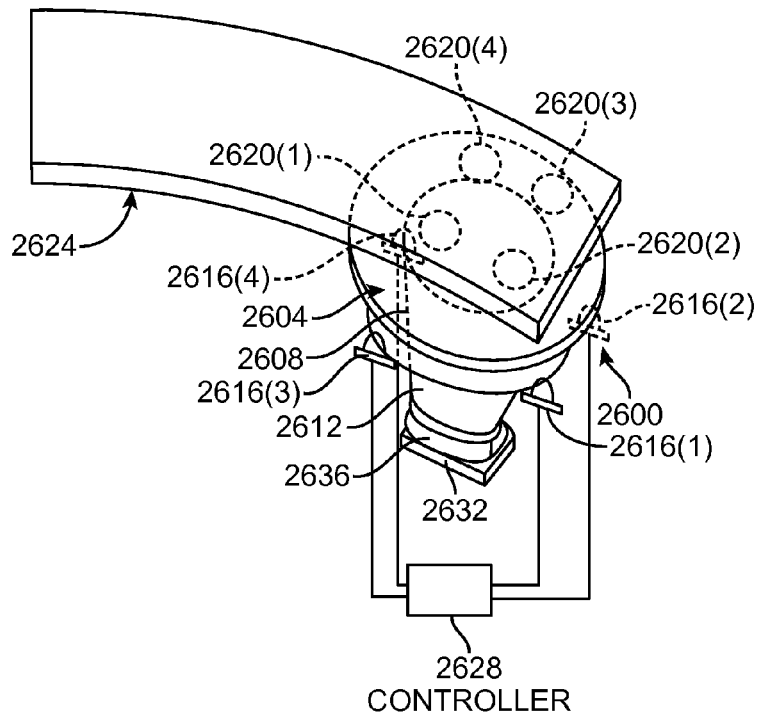
FIG. 26 is an isometric view of an optical reader system that illuminates a target with multiple spots of illumination.

In one example of a multi-reading scheme, four light sources (not shown) are used to illuminate four corresponding spots 2512(1) to 2512(4), with spots 2512(1) and 2512(2) consisting of one or more wavelengths that are not involved with fluorescence excitation and absorbance relative to chemical indicator 2500. Illumination spots 2512(1) and 2512(2) are for reference illumination. Spots 2512(3) and 2512(4), on the other hand, are for measurement illumination. Both spots 2512(3) and 2512(4) can be of the same or differing wavelengths (or wavelength bands) depending on the makeup of the relevant dye(s) within chemical indicator 2500. In one example, both spots 2512(3) and 2512(4) are for exciting the same fluorescence and contain the same excitation wavelength(s). This effectively allows the number of measurement readings on chemical indicator 2500 to be doubled. In another example, one of spots 2512(3) and 2512(4) is for an absorbance measurement and the other spot is for a fluorescence measurement. In a further example, one of spots 2512(3) and 2512(4) is for a first fluorescence measurement at one excitation wavelength and the other spot is for a second fluorescence measurement at a second excitation wavelength. In a still further example, one of spots 2512(3) and 2512(4) is for an absorbance measurement at a first absorbance wavelength and the other spot is for an absorbance measurement at a second absorbance wavelength. Those skilled in the art will readily appreciate the wide variety of scenarios that are possible depending on the makeup of a particular chemical indicator and the optical phenomenon(a) being measured. Of course, more or fewer spots of illumination can be used as desired to suit a particular use. In an example, spots 2512(1) to 2512(4) are typically illuminated at differing times so that the light from one does not interfere with readings for another. FIG. 26 below illustrates one example of reader optics 2600 that can be used to implement the four spot illumination scenario illustrated in FIG. 25.

In one exemplary implementation and with continuing reference to FIG. 25, once spots 2512(1) to 2512(4) have been illuminated and corresponding readings have been acquired, the same pattern of spots are essentially replicated at corresponding respective spots 2516(1) to 2516(4), such that reference illumination spots 2516(1) and 2516(2) substantially or entirely overlap, respectively, the regions of chemical indicator 2500 previously illuminated by measurement illumination spots 2512(3) and 2512(4). With this overlap, reference illumination spots 2516(1) and 2516(2) are used to determine whether any contamination is, or is likely to be, present where measurements were previously taken using measurement illumination spots 2512(3) and 2512(4), respectively. If, for example, the results of the readings from reference illumination spots 2516(1) and 2516(2) indicate that one, the other, or both of the corresponding regions on chemical indicator 2500 are contaminated, then the corresponding monitoring system/unit can take a corrective action such as, for example, discard or assign a lesser weight to the reading(s) at the contaminated spot(s). Illumination spots 2516(3) and 2516(4) are new measurement illumination spots for taking measurement readings of chemical indicator 2500. As will be readily understood, as the pattern of the four illumination spots is stepped across chemical indicator 2500 (in this example seven times) to create substantial overlap or virtually exact coincidence of each reference illumination spot with a corresponding measurement illumination spot, each measurement spot can be tested for contamination. In the embodiment shown in FIG. 25, if discoidal chemical indicator apparatus 2508 is mounted to monitoring unit having a stepper motor, such as monitoring unit 2202 of FIG. 22, the stepping of the four-spot pattern can be performed by controlling the stepper motor to drive the chemical indicator apparatus by one or more steps to achieve the desired alignment of the measurement and reference illumination spots of the pattern. In other embodiments, for example embodiments wherein the chemical indicator apparatus is linearly movable with respect to an optical system that creates the multi-spot pattern, the corresponding monitoring unit can move the chemical indicator in a linear stepwise fashion to create the desired alignment of the measurement and reference illumination spots of the pattern. In still other embodiments in which the chemical indicator apparatus is fixed and the optical system(s) that generate(s) the illumination pattern is/are movable, then such optical system(s) can be moved in a stepwise fashion accordingly.

It is noted that in some embodiments it is desirable to keep the illumination spots in the pattern of spots at issue, such as measurement and reference illumination spots 2512(1) to 2512(4) in the four-spot pattern illustrated, from overlapping one another. This not only allows the measurement locations on a given chemical indicator to be discrete and independent, but it also assists in reducing photo-aging of the chemical indicator, especially if it is one that is highly susceptible to photo aging. As those skilled in the art will understand, many fluorescent and absorptive dyes that can be used in a chemical indicator of the present disclosure undergo photo-aging, i.e., they become less responsive with increasing amounts of light exposure. Keeping the individual spots in a given pattern, such as the four-spot pattern of FIG. 25, from overlapping, may reduce the overall exposure of each region of the indicator that is illuminated by the corresponding illumination spots to only the light that is necessary for measurement and contamination readings of that region.

As can be readily appreciated, a monitoring system/unit can utilize the multi-reading, iterative stepping process illustrated with respect to FIG. 25, or other similar process, to ensure that the measurement and contamination readings are being taken from the correct chemical indicator. As seen in FIG. 25, chemical indicator 2500 is located adjacent a second chemical indicator 2520 but is separated therefrom by a space 2524, which can be, for example, a bare part of the holder 2528 of chemical indicator apparatus 2508. Since space 2524 will typically have (much) different optical responses than chemical indicators 2500 and 2520 to the measurement and reference illumination light, here spots 2532(1) to 2532(4), than both of the chemical indicators, the measurement and contamination readings taken from space 2524 will typically be discernible from measurement and contamination readings made on the chemical indicators. Analysis of the reading data by a monitoring system/unit can reveal where those typically vastly different readings lie in the data, and these readings can be used to separate readings taken from adjacent chemical indicators.

FIG. 26 illustrates an exemplary reader optics system 2600 that can be used to generate the four-spot illumination pattern illustrated in FIG. 25 and also to obtain readings based on those spots. Referring to FIG. 26, optics system 2600 includes a combined I/LC 2604 that can be the same as or similar to combined I/LC 1600 of FIG. 16 or combined I/LC 1800 of FIG. 18 and therefore can include spot lensing 2608 and a central light collector 2612. Optics system 2600 also includes four light sources, here four lensed LEDs 2616(1) to 2616(4), that provide light to spot lensing 2608, which in turn uses the light to form four corresponding respective illumination spots 2620(1) to 2620(4) on a target 2624, which can be, for example, a chemical indicator, a holder, or other part of a chemical indicator apparatus. Relating illumination spots 2620(1) to 2620(4) to FIG. 25, these spots can correspond, respectively, to illumination spots 2512(1) to 2512(4) and to illumination spots 2516(1) to 256(4), among other sets of illumination spots not particularly labeled in FIG. 25.

Referring back to FIG. 26, and continuing with the four-spot pattern of FIG. 25, LEDs 2616(1) and 2616(2) can be selected to provide reference illumination, i.e., provide light at one or more wavelengths that is not involved with taking either fluorescence measurements, absorbance measurements, or both. In one embodiment, each of LEDs 2616(1) and 2616(2) emit light at about 720 nm wavelength. Correspondingly, LEDs 2616(3) and 2616(4) can be selected to provide measurement illumination, i.e., illumination that is either fluorescence exciting or absorbed, or both, depending on the particular optical characteristic(s)/response of one or more chemical indicators being measured. As can be readily seen in FIG. 26, illumination spots 2620(1) to 2620(4) substantially do not overlap one another for at least the reasons noted above. In one example, LEDs 2616(1) to 2616(4) are controlled by a suitable controller 2628 that causes them to illuminate in a manner such that only a single one of the LEDs is turned on at a time. This minimizes the amount of stray light that interferes with any given reading. Optics system 2600 further includes a light detector 2632 that detects the light collected by light collector 2612. In this example, a light filter 2636 is provided to filter unwanted wavelengths from the collected light. Those skilled in the art will readily understand that optics system 2600 is but one example of an optics system that can be used to perform a multi-reading, multi-stepping process, such as the process described above with respect to FIG. 25.

Fluorescence Reading Contamination Compensation

In one exemplary aspect, with fluorescence, it is believed that most naturally occurring contamination/interference on the surface of a chemical indicator will reduce fluorescence, not increase it. Using corresponding reference illumination and measurement illumination spots, such as contamination and measurement spots 2516(1) and 2512(1) of FIG. 25, fluorescence emission measurements can be adjusted using the readings from both illumination spots at any reading location. For example, this adjustment can be made using a ratio of a reading of the reference illumination spot to a known calibration set point. To illustrate, if the reading from the reference illumination spot is supposed to always be 10,000 analog-to-digital (A/D) converter counts but a current reading is 9,800, then the ratio of the reading to the calibration set point is 9,800/10,000, or 0.98. The corresponding reading of the fluorescence emission from the same region of the chemical indicator at issue can then be divided by 0.98 to calculate a corrected reading. This method can also/alternatively be used to compensate for errors due to spacing variations between the reader and a chemical indicator, turbidity, and other factors. In the example utilizing four LEDs 2616(1) to 2616(4) (FIG. 26), since the same detector 2632 is used for all four light sources, this arrangement inherently compensates for the temperature of the detector.

Ambient Light Compensation

Light from sources other than reader can interfere with the reading process. For example, ambient light from outside a monitoring system, such as light from aquarium lighting, room lighting, the sun, etc., can reach the detector, such as detector 2632 of FIG. 26. To compensate for ambient light, the monitoring system/unit can be programmed to take an ambient light reading just before a reading light source is turned on and a reading integration cycle is started. An ambient light reading can be just an integration of light on the detector for a period of time without any of the reader light sources turned on. Once the ambient light is known, it can be converted into A/D counts per µs, which is a correction factor that can be used to subtract the ambient light value from any given detector integration measurement. For example, if an ambient reading is 500 A/D counts for a 10,000 µs integration time, the correction factor is 500/10,000 µs=0.05 counts/µs. Then, if a 2,000 µs long reading is taken with any of LEDs 2616(1) to 2616(4) and the reading is, say, 8,050 A/D counts, then the reading can be corrected by subtracting from that measurement reading 0.05 counts/µs×2000 µs=100 counts, such that the final reading adjusted for ambient light is 8,050 counts−100 counts=7,950 counts. This adjusted reading can then be used in any desired manner to produce measurement information.

Chemical Indicator Spacing Compensation

As described above, a combined I/LC of the present disclosure can be designed and configured to enable the corresponding light detector(s) to detect nearly the same amount of light from a target over a relatively wide range of variation in the position of the target relative to the light source(s) and detector. However, in some cases, such as to further enhance the accuracy of readings of such as combined I/LC or wherein such a forgiving arrangement of light source(s) and detector(s) is not available, it is useful to collect target position information and use this information to adjust detector readings accordingly. In one example, in monitoring unit, such as monitoring unit 2202 of FIG. 22 that includes a pair of electrodes (see, e.g., electrodes 2236 of FIG. 22) for measuring the conductivity of the water, those electrodes can be used to determine the spacing of the chemical indicator apparatus (see, e.g., chemical indicator disc 2204 of FIG. 22) is from the electrodes plane of the electrodes. In other embodiments, spacing information may be determined by other procedures. Using this spacing information and other information known about the chemical indicator apparatus and the monitoring unit, the distance between reader optics (see, e.g., optical assemblies 2212(1) to 2212(4)) can be determined. When the electrodes are close to a corresponding reader optical assembly (such as shown in FIG. 9 with electrodes 936 proximate to reader optical port 908(2)), a conductivity measurement can be taken at each chemical indicator from which a reading will be taken using that reader optical assembly for determining the distance between that chemical indicator and the reader optical assembly. With the distance to the target (here, the chemical indicator) being known, the monitoring unit can use that distance to correct the reading of the corresponding light sensor to account for any difference in brightness of the measurement light reaching the target due the actual distance being different from the design difference. Again, such differences can be due, for example, to tolerances in the fit of the chemical indicator apparatus with a monitoring unit, wobble of the chemical indicator apparatus due to movement of the water in which the apparatus is submerged, etc. Differences between the design distance to the target and the actual distance to the target can cause differences in the amount of light collected by a light detector of a measurement reader. Consequently, deviations in distance can be accounted for using procedures similar to the procedures describe above in the section titled "Fluorescence Reading Contamination Compensation."

Figure 27:
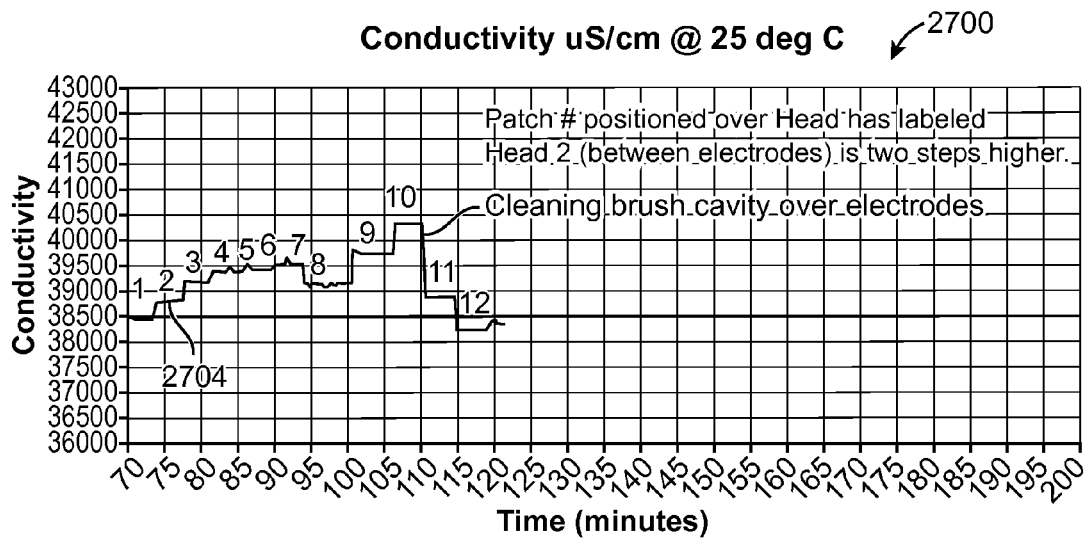
FIG. 27 is an exemplary graph of conductivity versus time illustrating the use of water-conductivity electrodes being used to determine the distance of a chemical indicator apparatus from the electrodes.

The reason that conductivity measurement electrodes, such as electrodes 2236 of FIG. 22, can be used in determining the distance between reader optics and a target for the optics (such as a chemical indicator) is that when the electrodes are located so that they measure the conductivity of the water between a chemical indicator apparatus and a monitoring unit (or other structure to which the chemical indicator apparatus is engaged (such as an aquarium wall 4628 as in FIG. 46), the conductivity measured relates to the amount of water in that space. Since that volume changes with the distance between the chemical indicator apparatus and the electrodes, the conductivity likewise changes with the distance between the chemical indicator and the electrodes. FIG. 27 illustrates a graph 2700 of conductivity versus time for conductivity readings taken by a monitoring unit of the present disclosure, such as monitoring unit 812 (see, e.g., FIG. 9), as the monitoring unit moved chemical indicator disc 1900 of FIG. 19 past electrodes 936. In this example, disc 1900 contains twelve discrete recesses, eleven containing chemical indicators and one (corresponding to region labeled "10" in graph 2700 of FIG. 27) being a cavity for a cleaning element, such as cleaning element 1904 of FIG. 19. In graph 2700, conductivity profile 2704 provides an indication of error in the distance of disc 1900 (FIG. 19) to the surface of monitor unit 812. In the example of graph 2700, the total variation is about 5.1%. As can be readily appreciated, a conductivity measurement could be taken in conjunction with each fluorescence, absorbance, and/or reflectivity measurement by an optical reader (not shown) in communication with optical reader port 908(2) of FIG. 9. A baseline can be determined, for example, by having the monitoring system/unit measure the average conductivity for all chemical indicator positions. The conductivity for each chemical indicator position can then be expressed as a percentage relative to the average of all positions. An advantage of using conductivity measurements for determining target distance relative to optical approaches is that conductivity is less affected by optical contaminants in the water.

Chemical Indicator Age Compensation

As mentioned in the previous section, aging of a chemical indicator can be a design issue that needs to be considered, for example, for reliability of measurements taken over time as the chemical indicator ages from continual illumination for measurements and/or contamination determination and, in some cases, from ambient light, and from time-aging of indicator dyes themselves. As a chemical indicator ages, the intensity of its response to excitation (fluorescence) or its absorbency, or both, diminishes, and the corresponding diminished readings need to be distinguished from lower readings that are due to changes in the water the chemical indicator is being used to measure. For example, if a monitoring system/unit interprets a low reading as indicating that the level of a particular constituent of the water is below a predetermined threshold, then the monitoring system/unit might recommend that a certain additive be added to the water to bring the level of that constituent back up into tolerance. However, if that low reading was in fact due to aging of the chemical indicator rather than the level of the constituent being low, then the instruction to dose the water with an additive could easily result in the addition of the additive causing the constituent level to be too high. Consequently, it can be seen that tracking and factoring chemical indicator aging into any measurement data and/or dosing instructions generated by a monitoring system/unit can be an important aspect of ensuring dosing accuracy and water quality.

Figure 28:
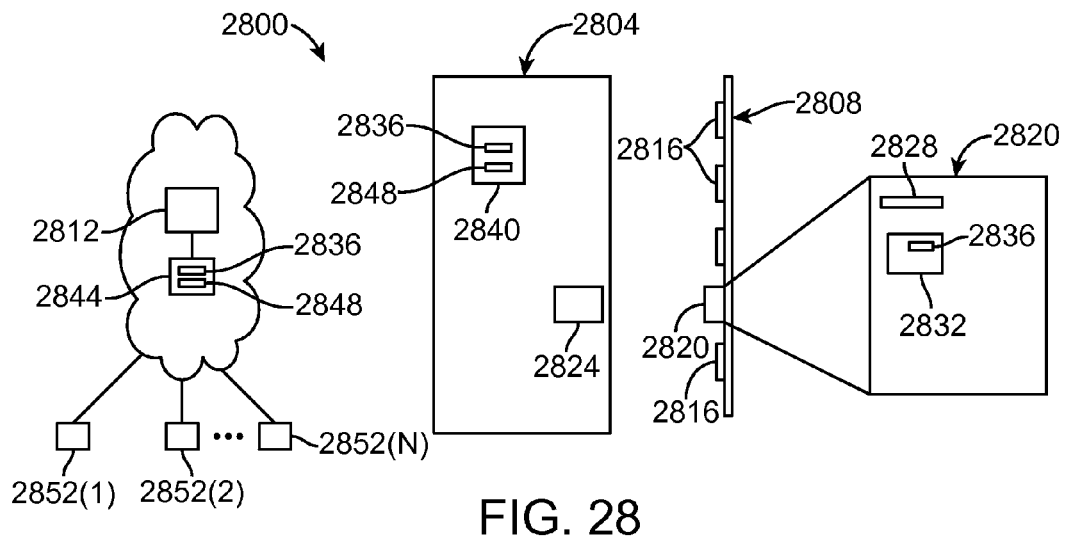
FIG. 28 is a schematic/block diagram of a system that enables storage of data on a chemical indicator apparatus.

To at least partially account for photo-aging, a measurement/monitoring system/unit of the present disclosure can be configured to track the amount of light to which each region of a chemical indicator is exposed over the life of the chemical indicator. For example, FIG. 28 illustrates a water quality monitoring system 2800 that includes a monitoring unit 2804, a chemical indicator disc 2808 engaged with the monitoring unit, and a shared, for example, cloud-computing-based, software application 2812 that is in at least intermittent communication with the monitoring unit. Chemical indicator disc 2808 includes a plurality of chemical indicators 2816 and a read/writable RFID device 2820. Correspondingly, monitoring unit 2804 includes an RFID reader/writer 2824. When disc 2808 is manufactured, it is provided with a unique ID 2828 and a data structure 2832 that holds various data, including light exposure data 2836 for the various chemical indicators 2816. In one example, exposure data 2836 is expressed in watt-seconds, which can be readily determined by knowing the output of the relevant light source(s) (not shown) and the cumulative amount of time that each light source is on when exposing a particular indicator, and a particular region on that indicator.

When chemical indicator disc 2808 is first used and it is engaged with monitoring unit 2804, monitoring unit 2804 causes RFID reader/writer 2824 to read unique ID 2828, which the monitoring unit can store and/or send to software application 2812 for product registration and tracking. As monitoring unit 2804 continually takes measurement and/or contamination detection readings from chemical indicator disc 2808 during use, at certain times, for example, regular intervals, continually, at certain clock times, it can cause RFID reader/writer 2824 to write pertinent exposure data 2836 or updating data, etc., to RFID device 2820 on the disc. Monitoring unit 2804 can alternatively or additionally store such data 2836 internally in a suitable memory 2840 and/or upload the data to a data store 2844 of shared software application 2812 for tracking/redundant tracking. Writing exposure data 2836 to RFID device 2820 on chemical indicator disc 2808 can be useful, for example, if the disc is later used with another monitoring unit that is not in communication with shared software application 2812, among other reasons. Those skilled in the art will readily understand that the physical components used in the example are merely illustrative and that other physical components that provide the same or similar functionality can readily be substituted with no undue experimentation.

With continual tracking of exposure of chemical indicator disc 2808 to light from monitoring unit 2804, which due to its intensity, can typically be considered to be at least the majority of light to which the disc is exposed over time, exposure data 2836 can be compared to known benchmark photo-aging data 2848 determined, for example, in a laboratory for like chemical indicators, and any adjustments to the reading data acquired from the aged chemical indicators 2816 can be made as needed. Such adjustments can be made internally within monitoring unit 2804, by shared software application 2812, or both. A benefit to having adjustments made by shared software application 2812 is that benchmark photo-aging data 2848 can be updated and/or newly added easily at a central location without the need to provide the revised data to each of the monitoring units, such as monitoring unit 2804 and other monitoring units 2852(1) to 2852(N), that utilize the shared software application.

Figure 29:
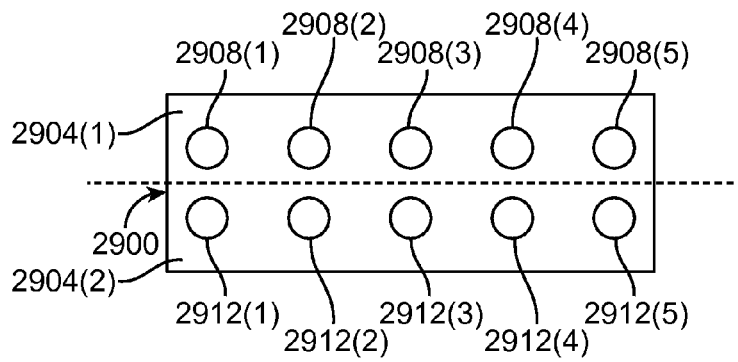
FIG. 29 is a plan view of a chemical indicator and ten measurement illumination spots, five being of one brightness and five being of a second brightness, for illustrating a method of compensating for photo-aging of the chemical indicator.

Another way of compensating for aging of a chemical indicator is to use redundant light sources having the same wavelength profiles but that provide differing brightness levels. In this manner, the differing regions of a chemical indicator exposed to the light of differing brightness will photo-age at differing rates. For example, FIG. 29 illustrates a chemical indicator 2900 that is divided into first and second aging regions 2904(1) and 2904(2). In first aging region 2904(1), chemical indicator 2900 is exposed to illumination of brightness x, which is applied at each of illumination spots 2908(1) to 2908(5). However, in second aging region 2904(2), chemical indicator 2900 is exposed to reduced-brightness illumination x/y (wherein y>1), which is applied at each of illumination spots 2912(1) to 2912(5). While the value of y can be any in the range noted above, simple examples include y=2 and y=3, such that brightness in second aging region 2904(2) would be one-half and one-third, respectively, of the brightness of the illumination in first aging region 2904(1). These examples are merely illustrative and not limiting.

Figure 30:
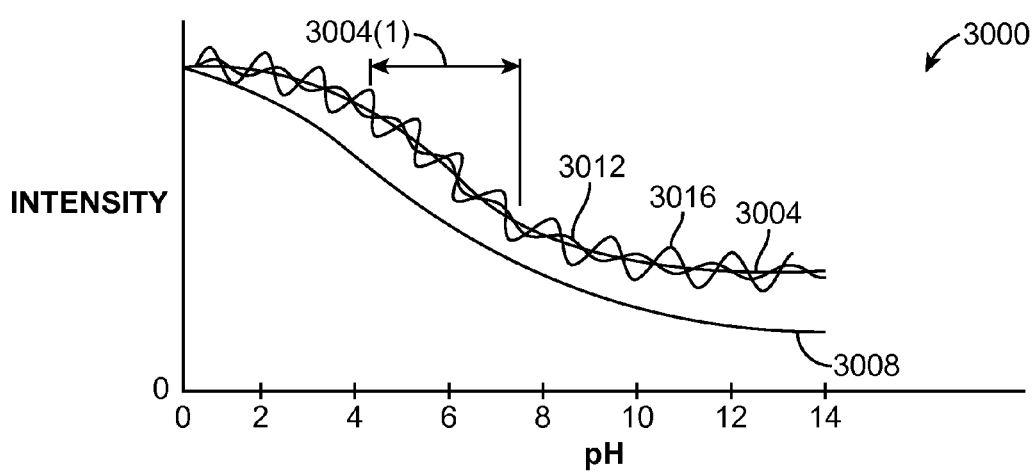
FIG. 30 is an exemplary plot of reading intensity versus expose time for a particular chemical indicator illustrating a method of compensating for photo-aging of the chemical indicator.

FIG. 30 is an exemplary graph 3000 of optical reading intensity (e.g., digitizer counts) versus parameter value for a particular chemical indicator. In the example shown, the parameter is the pH level of the water. In graph 3000, "New x" curve 3004 indicates the reading intensity over a range of the parameter when the chemical indicator is new and exposed to measurement illumination of brightness x. As can be seen, the region 3004(1) of curve 3004 is the most useful part of the curve, since changes in the parameter in this region result in the greatest changes in the reading intensity. Thus, in this example, the chemical indicator would be most useful for monitoring pH in the range of about pH 4.5 to pH 7.5. However, "Aged x" curve 3008 indicates the reading intensity over the range of the parameter when the chemical indicator is aged a certain amount and exposed to measurement illumination of brightness x. As can be seen by comparing curves 3008 and 3004, as chemical indicator ages, the intensity of the readings at brightness x is reduced.

Similarly, "New x/3" curve 3012 and "Aged x/3" curve 3016 indicate, respectively, the reading intensity over the range of parameter when the chemical indicated is new and aged a certain amount and exposed to measurement illumination of brightness x/3, i.e., illumination that is one-third the brightness of x. A drawback of using light of reduced brightness is that there can be quite a bit more noise than if a higher brightness is used. This noise is seen in curves 3012 and 3016 in the form of the undulations of the curves. However, it can be seen that the reading intensities of both the new and aged readings at reduced brightness x/3 are substantially the same as the intensity of the new readings at brightness x. This information, and knowing benchmark aging profile data for brightness x (such as "Aged x" curve 3008) can be used to make adjustments to the measurement readings over time as the chemical indicator ages. Benefits of using this procedure is that historical light exposure data is not needed and it accounts for light exposure, such as ambient light exposure during use and/or during periods of nonuse, storage, etc. As noted above, these adjustments can be desirable to increase the accuracy of the measurements provided to a user and/or to increase the likelihood that the water being monitored is receiving the proper dosing and is remaining within its target quality tolerances.

Friction Testing

When a chemical indicator apparatus is driven to multiple reading positions using a coupling having significant play, such as a magnetic coupling, friction between the chemical indicator apparatus and the support structure(s) with which it is engaged can be so great that the monitoring system/unit may "believe" it is reading one chemical indicator when it is actually reading another. As an illustration, envision that chemical indicator disc 2500 of FIG. 25 is engaged with monitoring unit 812 of FIG. 8 and is driven by the magnetic coupling illustrated in FIG. 9. As can be seen in FIG. 25, chemical indicators 2500 and 2520 are relatively close together, and if enough friction is present, monitoring unit 812 (FIG. 8) could be "thinking" it is taking a reading on chemical indicator 2500, when friction has interfered with the rotation of disc 2508 to the extent that the reading at issue is actually from chemical indicator 2520, assuming a clockwise rotation of the disc as seen in FIG. 25.

Figure 31:
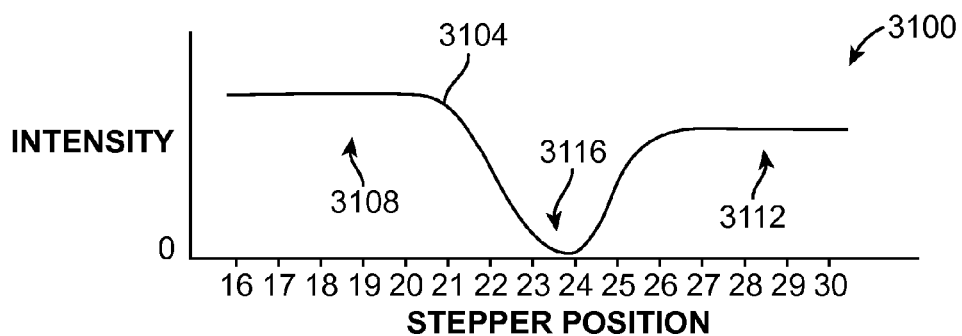
FIG. 31 is a graph of reading intensity versus stepper position for readings of two chemical indicators when moving a chemical indicator disc in a clockwise direction.

One way that monitoring unit 812 (FIG. 8) can determine how much friction is present between disc 2508 and the monitoring unit is to take readings in both a clockwise direction and a counterclockwise direction, correlate the readings to one another, and analyze the correlation data. This is illustrated with FIGS. 31 to 34. Referring to these figures as noted, and also to FIG. 25 where indicated, FIG. 31 is a graph 3100 of reading intensities versus stepper motor position for readings taken while driving chemical indicator disc 2508 (FIG. 25) in a clockwise direction relative to FIG. 25. While readings are taken at discrete stepper motor positions, the curve 3104 in graph 3100 is a fitted curve fitted to the data points. Region 3108 of curve 3104 corresponds to readings taken from chemical indicator 2520 (FIG. 25) and region 3112 of the curve corresponds to readings taken from chemical indicator 2500. Region 3116 of curve 3104 corresponds to readings taken at space 2524 (FIG. 25) between chemical indicators 2520 and 2500. In this example, holder 2528 (FIG. 25) is made of black plastic, which is exposed at space 2524, so the intensities of the readings are low because of the high absorbance of the black plastic to the illuminating light.

Figure 32:
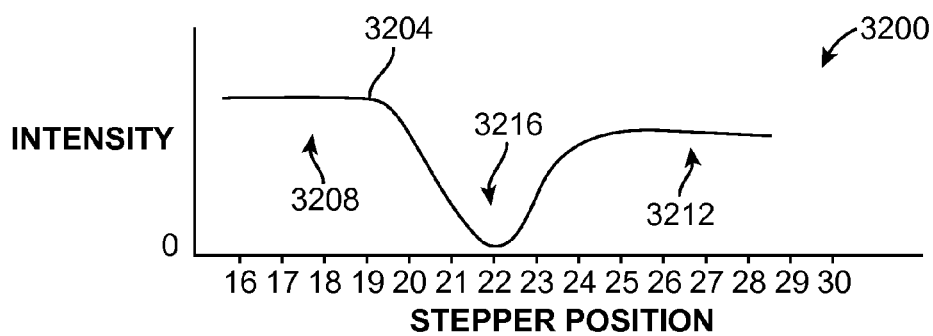
FIG. 32 is a graph of reading intensity versus stepper position for readings of two chemical indicators when moving the chemical indicator disc in a counterclockwise direction.
Figure 33:
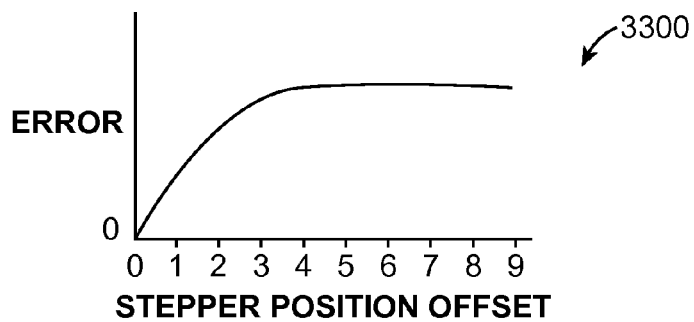
FIG. 33 is a graph of combined error between clockwise and counterclockwise chemical indicator readings versus stepper offset wherein no friction is present between the chemical indicator disc and its mount(s)

FIG. 32 is a graph 3200 of reading intensities versus stepper motor position for readings taken while driving chemical indicator disc 2508 (FIG. 25) in a counterclockwise direction relative to FIG. 25. As with curve 3104 of FIG. 31, curve 3204 of graph 3200 is a fitted curve fitted to the data points. Region 3208 of curve 3204 corresponds to readings taken from chemical indicator 2520 (FIG. 25) and region 3212 of the curve corresponds to readings taken from chemical indicator 2500. Region 3216 of curve 3204 corresponds to readings taken at space 2524 (FIG. 25) between chemical indicators 2520 and 2500, which, again is black plastic in this example. Those skilled in the art will understand that the stepper motor positions shown in graphs 3100 and 3200 are absolute and not directional. Therefore, assuming the stepper motor positions increase as disc 2508 is rotated in a clockwise direction, the readings of graph 3100 of FIG. 31 are taken in the stepper motor position order 16, 17, 18, 19, etc., and the readings of graph 3200 of FIG. 32 are actually taken in reverse order, for example, 28, 27, 26, 25, etc.

Figure 34:
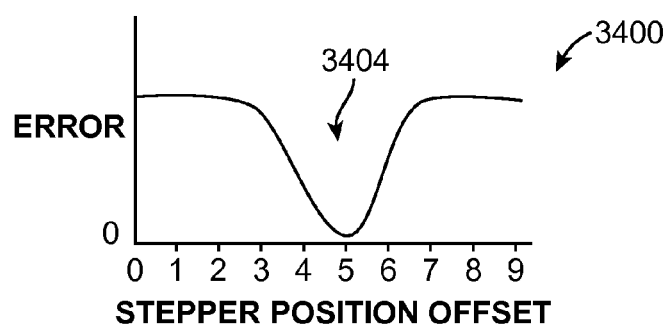
FIG. 34 is a graph of combined error between clockwise and counterclockwise chemical indicator readings versus stepper offset wherein friction is present between the chemical indicator disc and its mount(s)

Once intensity data has been obtained for readings taken in both the clockwise and counterclockwise direction, such as the data illustrated, respectively, by graphs 3100 and 3200, the data can be compared, for example, using a cross-correlation function that compares the data points at each stepper motor position and finds the differences between them to provide an error for that position. Indeed, the amount of friction, in terms of stepper motor positions, can be determined, for example, by shifting one of curves 3100 and 3200 relative to the other in one-step increments in both directions and calculating the sum of the errors at each stepper motor position. When the two curves are at their position of greatest alignment, the sum of the errors at that stepper motor position will be at a minimum. With due noting of the stepper position offset at which the minimum sum of errors occurs, the collected data can be adjusted accordingly. As can be readily appreciated, where the reading intensities in the two directions are the same or substantially the same at each and every position and the readings are taken very close to one another in time so that differences due to changes in the water parameter being measured can be neglected, then there is little to no friction in the system. This is illustrated by error curve 3300 of FIG. 33 where the error is nearly zero at zero offset, indicating that friction is not an issue. In contrast, error curve 3400 of FIG. 34 illustrates a situation in which friction is present. As can be seen in FIG. 34, in region 3404 of error curve 3400, which is at about an offset of five stepper positions, the cumulative error in intensity readings is relatively small, indicating that friction is causing the data collected in the two opposing directions to be about five stepper positions off from one another.

It is noted that if the monitoring system/unit determines that the friction and corresponding lag is excessive, it can take any one or more of a number of actions, such as: 1) attempting to solve the friction problem (e.g., in a disc-based example, by spinning the disc rapidly in one or both directions and performing another friction analysis after such spinning); 2) warning a user that the friction is too great; and 3) instructing a user to remove the chemical indicator apparatus (e.g., disc) from the monitoring system/unit, clean the contacting parts of the chemical indicator apparatus and monitoring system/unit; and 4) instruct a user to replace the chemical indicator apparatus or other part that may be causing the friction. It is noted that these actions may be performed in a certain sequence, such as action 4 being taken only after performing action 1 one or more times and after performing action 3 one or more times, among other sequences.

Dosing Protection/Action Matrix

Over time and for a variety of reasons, the readings/measurements taken by a water quality measuring/monitoring system/unit, such as any of such systems and units described in this disclosure, become less accurate. For example, reading error can be introduced due to any one or more of the following: 1) light output imbalance between "identical" light sources; 2) light source degradation over time; 3) chemical indicator photo-aging; 4) chemical indicator water-aging; 5) chemical indicator water-borne fouling; 6) optical system water-borne fouling; and 7) friction between a chemical indicator apparatus and a measuring/monitoring system/unit, among others. With so many sources of error and with the desire to reasonably ensure that the aquatic environment being measured/monitored is being properly measured/monitored and/or is receiving proper dosing of additives, it is desirable to determine the level of confidence that can be placed on the readings being taken at any point in time. By determining a confidence level, the measuring/monitoring system/unit can then take certain actions (or not) as the confidence level decreases (or uncertainty increases).

Figure 35:
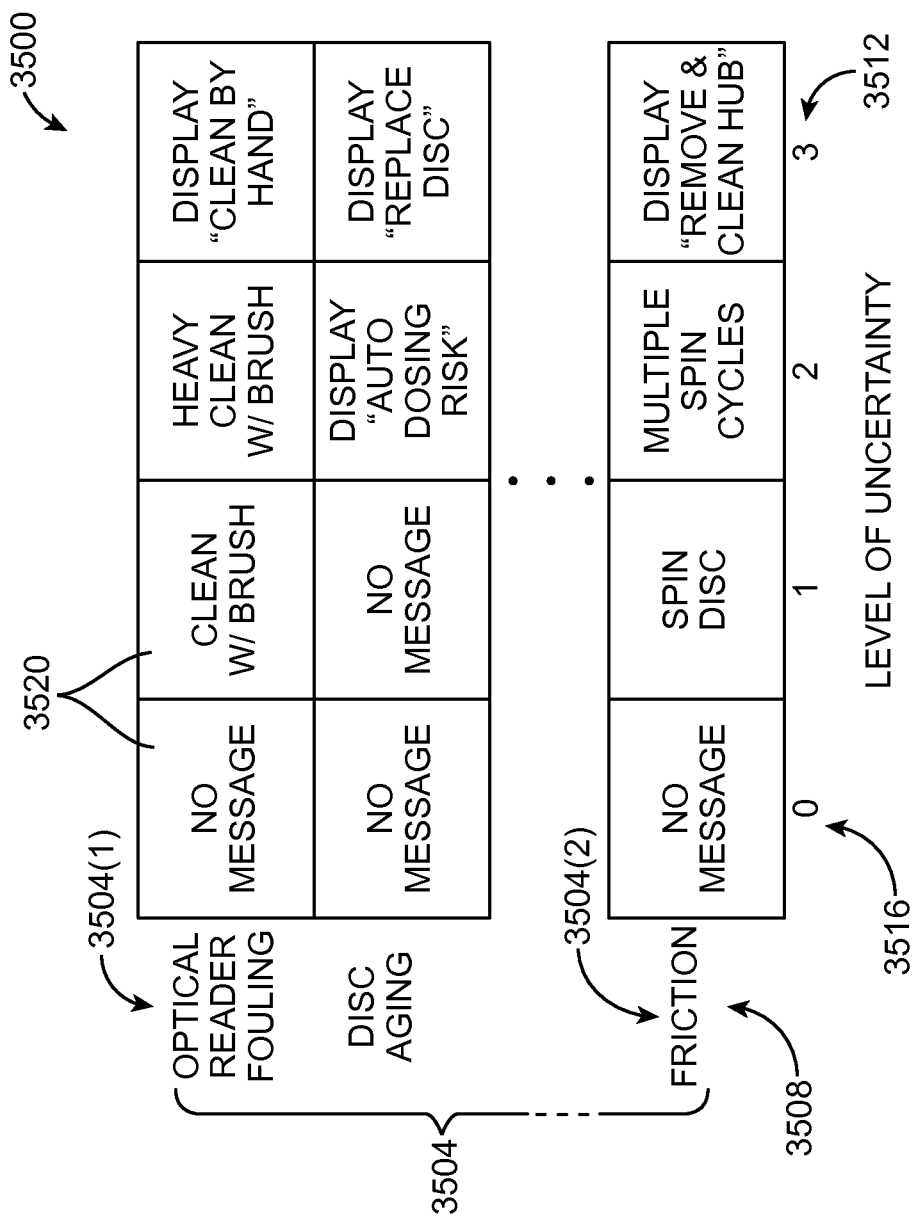
FIG. 35 illustrates a confidence matrix for a water quality monitoring system for use in determining actions as a function of uncertainty of reading accuracy based on various error inducers.

FIG. 35 depicts an exemplary action matrix 3500 for a set of error sources 3504. In this example, which is merely illustrative and should not be considered limiting, each error source 3504 is assigned to a row 3508 of matrix 3500, and each column 3512 corresponds to an uncertainty level 3516. Here, uncertainty levels 3516 range from "0" (i.e., effectively no uncertainty) to "3" (highest uncertainty), with the level being determined based on suitable information, such as photo-aging data, water-aging data, friction-test data, light-balance data, etc., that depends on the error source 3504 at issue. The various cells 3520 of action matrix 3500 are actions that the corresponding measuring/monitoring system/unit, such as any one of the measuring/monitoring systems/units described in this disclosure, takes relative to each of error sources 3504 for each uncertainty level 3516. For example, when optical system water-borne fouling 3504(1) is the error source 3504 at issue, when the measuring/monitoring system/unit at issue determines that uncertainty level 3516 is a relatively low "1", then it may simply try to clean the optical system itself, such as by using a cleaning element (e.g. cleaning element 1904 of FIG. 19) onboard the system, such as on the chemical indicator apparatus. However, if the measuring/monitoring system/unit determined that uncertainty level 3516 for optical system water-borne fouling 3504(1) is moderate to high, i.e., "2" or "3", for example after attempting to self-clean the optical system, then the system/unit may issue an instruction (e.g., via a GUI) that instructs the user to remove the chemical indicator apparatus and clean it manually. As another example, when chemical indicator apparatus/monitoring unit friction 3504(2) is the error source 3504 at issue, when the measuring/monitoring system/unit at issue determines that uncertainty level 3516 is a relatively low "1", then it may simply try to correct the friction problem. For example, if the chemical indicator apparatus is a disc, then the measuring/monitoring system/unit can spin the disc at a high speed for a certain amount of time. However, if the measuring/monitoring system/unit determined that uncertainty level 3516 for friction 3504(2) is moderate to high, i.e., "2" or "3", for example after attempting to self-correct the friction problem, then the system/unit may issue an instruction (e.g., via a GUI) that instructs the user to remove the chemical indicator apparatus and clean the faying surfaces manually. Of course, these examples are only illustrative, and those skilled in the art will readily be able to develop an action matrix for any particular embodiment and application.

As mentioned above, it is desirable to have a certain level of confidence in the measurements/readings that a given measurement/monitoring system/unit is making to inhibit improper dosing of the water in the aquatic environment that is being measured/monitored. Because errors can be cumulative, it can be desirable to calculate an overall dosing confidence value based on the uncertainty levels for multiple error sources. In addition, because some error sources may not be as important to determining an overall dosing confidence value as others, any dosing confidence formula can include weighting. Following is an example of a formula that can be used to calculate a dosing confidence value, C:

$$C = w_1 U_1 + w_2 U_2 + w_3 U_3 + \ldots + w_n U_n \quad (1)$$

wherein:

$U_n$ is the uncertainty level for a particular error source, such as one of uncertainty levels 3516 for any one of error sources 3504 of FIG. 35; and $W_n$ is a weight indicating the importance of the corresponding error source in the determination of the dosing confidence value C.

As will be readily appreciated, with this formula using the value of uncertainty level 3516 of FIG. 35 for uncertainty levels and using positive real numbers for weights, the higher the dosing confidence value C, the lower the confidence that the dosing instructions (e.g., automated dosing instructions 2428 and/or assisted dosing instructions 2468 of FIG. 24) are correct. In an attempt to prevent improper dosing that may severely negatively impact the aquatic environment, for example, by killing fish, killing plants, killing coral, etc., if the measurement/monitoring system/unit determines that the calculated dosing confidence value C exceeds a predetermined threshold, then the system/unit may stop issuing dosing instructions altogether and/or issue one or more alerts, for example, via a GUI for the system/unit, providing one or more warnings to a user, such as that the monitoring system/unit will no longer issue dosing instructions, the monitoring system/unit should be checked, etc. Those skilled in the art will be able to determine a suitable threshold for a given situation. Those skilled in the art will also readily understand that Equation (1) for the determination of a dosing confidence value is merely illustrative and that any of a variety of other formulas can be used.

Dosing Rate Protection

Depending on the type of aquatic environment at issue, when dosing is needed, there may be limits imposed on how quickly one or more dosing additives should be added to the water. For example, for some species of fish, rapid changes in the pH of the water can cause inflammation of gill membranes. In some cases, the reaction to the rapid change can be so severe that the fish's ability to breathe is severely inhibited and death can result. In another example, if the aquatic environment is a saltwater-based coral environment and the water is at or near its carbonate/calcium saturation point, then adding calcium too quickly to the water can cause the precipitation of calcium carbonate, the effect of which is to undesirably reduce the level of those constituents. In both of these examples, as with many other examples that those skilled in the art will be familiar with or otherwise understand, it is desirable to avoid negative effects by ensuring that dosing is performed at a rate that the negative consequences, such as the gill inflammation in the first example and the calcium carbonate precipitation in the second example, do not occur.

In order to avoid the negative consequences for any particular aquatic environment and dosing situation, a dosing calculator of the present disclosure, such as any of dosing calculators 120 (FIG. 1), 240 (FIG. 2), and 2436 (FIG. 24), can make intelligent dosing rate decisions based on appropriate information about the aquatic environment and provide either automated dosing instructions and/or assisted dosing instructions, such as automated dosing instructions 2428 and 2468 of FIG. 24, respectively, based on those decisions. In this connection, a user interface, such as a GUI 3600 illustrated in FIG. 36 can be provided to allow a user to select/input any information that the dosing calculator would need to know in order to calculate dosing rate limitations for any one or more of the additives that may need to be added to the aquatic environment. As those skilled in the art will readily appreciate, any user interface provided for this purpose can be configured in any one or more of a variety of manners to allow a user to enter the necessary information. For example, the user interface can include one or more selection devices (hardware and/or software), such as drop-down menus, radio buttons, check boxes, etc., that allow a user to input the necessary information.

Figure 36:
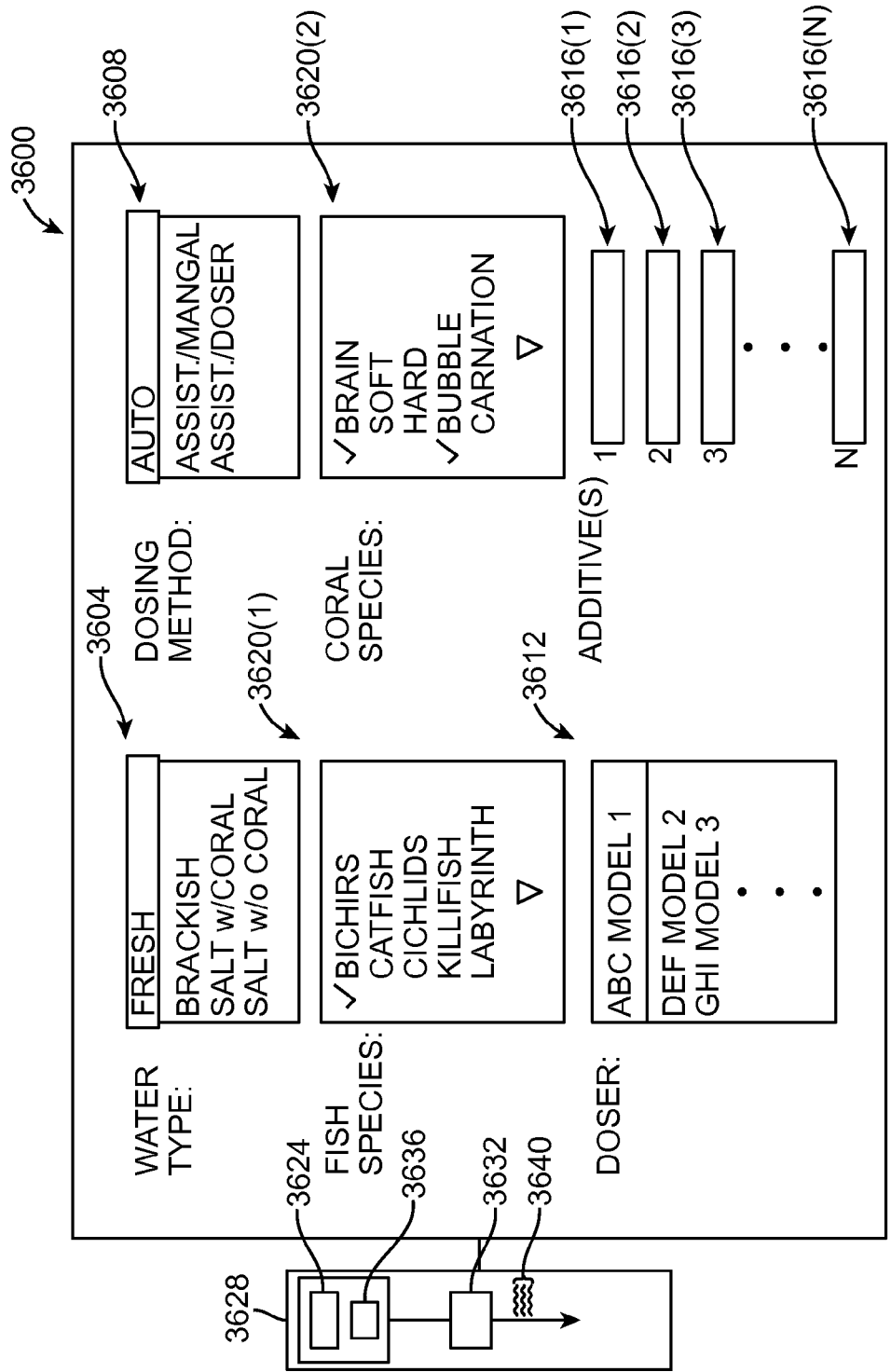
FIG. 36 illustrates a screenshot of a graphical user interface that allows a user to input information for implementing a water-quality monitoring and dosing system in an aquarium setup.

For example, GUI 3600 of FIG. 36, which is for a relatively large-screened computing device, such as a tablet computer, a laptop computer, or a desktop computer, includes 1) a drop-down water-type selector 3604 that allows the user to select the water type, 2) a dosing method selector 3608 that allows the user to indicate the method of dosing, 3) a drop-down doser make/model selector 3612 that allows the user to input the doser being used, if any, 4) a number of additive selectors 3616(1) to 3616(N) that each allow the user to select the brand/type of each additive available for adding to the water, and 5) one or more supported species selectors, here, selectors 3620(1) and 3620(2) for fish species and coral species, respectively. It is noted that one or more of the selectors 3612, 3616(1) to 3616(N), 3620(1), and 3620(2) can be dynamically generated based on selections made on one or more other selectors. For example, doser make/model selector 3612 may only be displayed when either the "AUTO" or "ASSISTED/DOSER" are selected, fish species selector 3620(1) may be populated with only the species of fish compatible with the water type selected (e.g., only freshwater fish are displayed when "FRESH" is selected), the coral species selector 3620(2) may appear only if "SALT W/CORAL" is selected, and the number and type of additive selectors 3616(1) to 3616(N) displayed can be based on, for example, the water type selected alone or in combination with one or more of the fish and coral species selected. Once the user has input all of the appropriate parameters, they can be stored as aquatic environment parameters 3624 in a suitable data store 3628. A properly programmed dosing calculator 3632 can use aquatic environment parameters 3624, along with a knowledge base 3636 of known problems that arise with dosing too fast and corresponding dosing rates that avoid those problems, to determine one or more proper dosing instructions 3640 that avoid the relevant excessive-dosing-rate problem(s). As mentioned above, dosing instructions 3640 can be of the automated dosing type, assisted dosing type, or both, like dosing instructions 2428 and 2468 of FIG. 24.

Confidence Levels Generally

As discussed above, a confidence level in one or more measurements by a measurement/monitoring system/unit may be influenced by one or more errors (i.e., adverse conditions) in aquatic environment monitoring and/or dosing system. Examples of adverse conditions that may influence a confidence level in one or more measurements include, but are not limited to, of a degradation in a chemical indicator due to photo-aging, a degradation in a chemical indicator due to water-aging, a physical contamination of a chemical indicator, an illumination imbalance related to an optical reader, a degradation of a light source of an optical reader, a physical contamination in water between an optical reader and a chemical indicator, a displacement due to friction between a chemical indicator apparatus and a monitoring unit, an error intrinsic in a chemical indicator, an error in distance between a chemical indicator apparatus and an optical reader, and any combinations thereof. In one exemplary aspect, one or more measured values for one or more errors/conditions can be used to determine a confidence level for a measurement taken from a chemical indicator. Different ways to measure error/conditions are discussed throughout the current disclosure. In one example, a determination of a confidence level and/or generation of instructions for correcting the condition (e.g., automatically acting to correct the condition using one of the components of a aquatic environment monitoring/dosing system according to the current disclosure, alerting a user to the condition, such that the user may act to correct the condition, discarding data, etc.) can be executed by a dosing calculator or other component of an aquatic environment monitoring and/or dosing system.

In certain examples, when a value of a confidence level exceeds a threshold (e.g., a threshold stored in a memory associated with an aquatic environment monitoring and/or dosing system as discussed herein) or moves to a position of interest, a confidence adjustment can be generated (e.g., by a dosing calculator or other processing component of a system). A confidence adjustment can be used to instruct an action. Example actions include, but are not limited to, actions by a monitor device, actions by a dosing device, actions by another component of the system, actions by a user of the system, and any combinations thereof. Additionally, an action or an instruction to take an action related to correcting a condition of a component of the system can occur to correct one or more of the errors/adverse conditions discussed herein. For example, a measured value for a constituent of an aquatic environment (e.g., calcium, magnesium, pH, carbonate, etc.) may be modified based on a confidence value. Other examples include, but are not limited to, providing an alert or other instruction to a user (e.g., via a graphical user interface), automatically addressing an adverse condition, changing a rate of dosing, providing a modified assisted dosing instruction, and any combinations thereof.

Figure 37A:
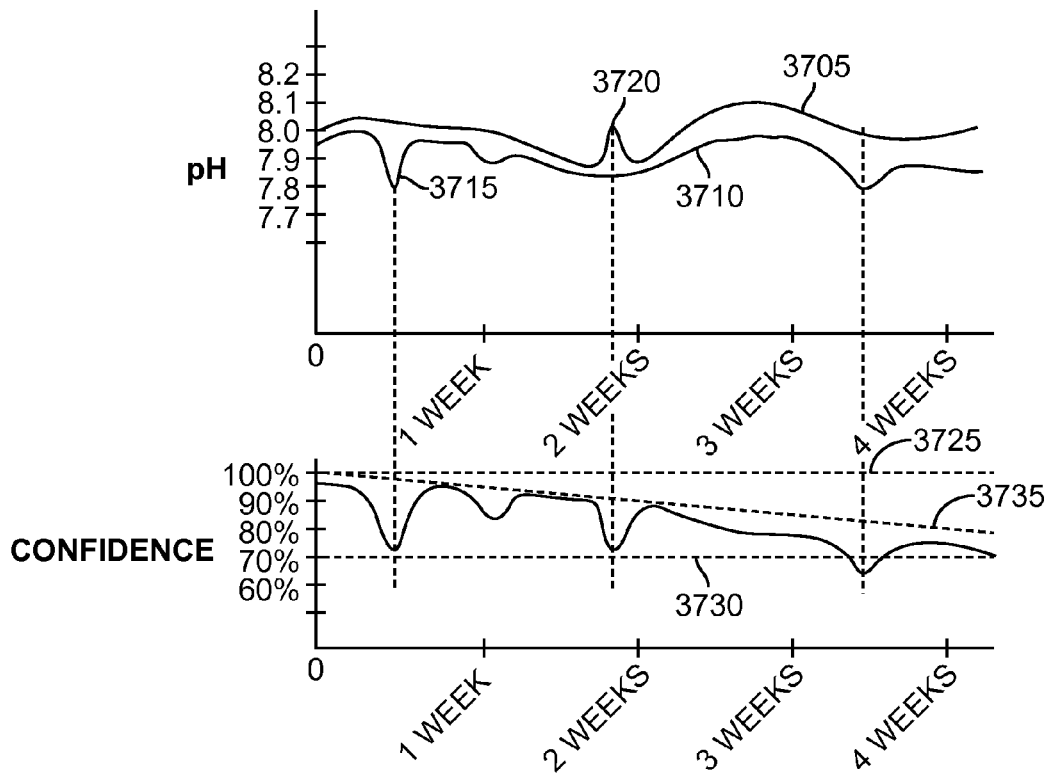
FIG. 37A illustrates one example of a confidence level plot for exemplary measured pH values.

Several ways of utilizing a confidence level are discussed above (e.g., with respect to an action matrix, such as the action matrix shown in FIG. 35; with respect to Equation (1) discussed above for combining confidence level values for a plurality of errors/conditions. In other examples, confidence level data may be plotted and/or measured over time for a plurality of data readings to show trends in confidence for the readings over that time period. FIG. 37A illustrates an example of pH measured data over a four week time (top graph of the figure) with corresponding confidence level data (lower graph of the figure). In this example, pH values are obtained using a plurality (e.g., ten) optical spot readings on an chemical indicator, such as is discussed above with respect to FIG. 29. At each time interval a plurality of pH values are obtained with the upper value of the plurality of values plotted over time as line 3705 and the lower value of the plurality of values plotted over time as line 3710. Where the upper value line 3705 and lower value line 3710 are closer together, the range of values measured from the multiple optical spots on the chemical indicator is small. Where the upper value line 3705 and lower value line 3710 deviate from each other, such as at location 3715 (where the lower values deviate greatly from the upper values) and at location 3720 (where the upper values deviate greatly from the lower values), the range between the values measured from the multiple optical spots on the chemical indicator is large. A large range can be an indication of an obstruction or other error condition in one or more regions of the chemical indicator. The lower confidence plot in the figure shows confidence level in the measurements in percentages. Where the range of measured pH values differ greatly, the confidence is shown to decrease (such as at locations in time 3715 and 3720). The lower confidence plot also shows a 100% confidence level 3725 (indicated by the horizontal dotted line) and a confidence threshold indicated by the dotted line 3730. Confidence values below the confidence threshold 3730 may trigger one or more actions, as discussed above (such as alerting a user, discarding one or more measured values, automatically taking action (e.g., changing a rate of dosing, stopping dosing, spinning an indicator disc at a high rate of speed, engaging a cleaning mechanism to clean an optical reader optic, etc.))

The lower confidence plot also shows a sloping dotted line 3735 illustrating the decreasing confidence in measurements over time (e.g., due to known photo aging, aging of a chemical indicator due to water exposure, etc.). Thus, in this example, confidence values decrease with variations in the range of pH values and also decrease steadily over time. Due in part to the decreasing confidence over time, the likelihood of exceeding the threshold line 3730 increases with time in this example.

Figure 37B:
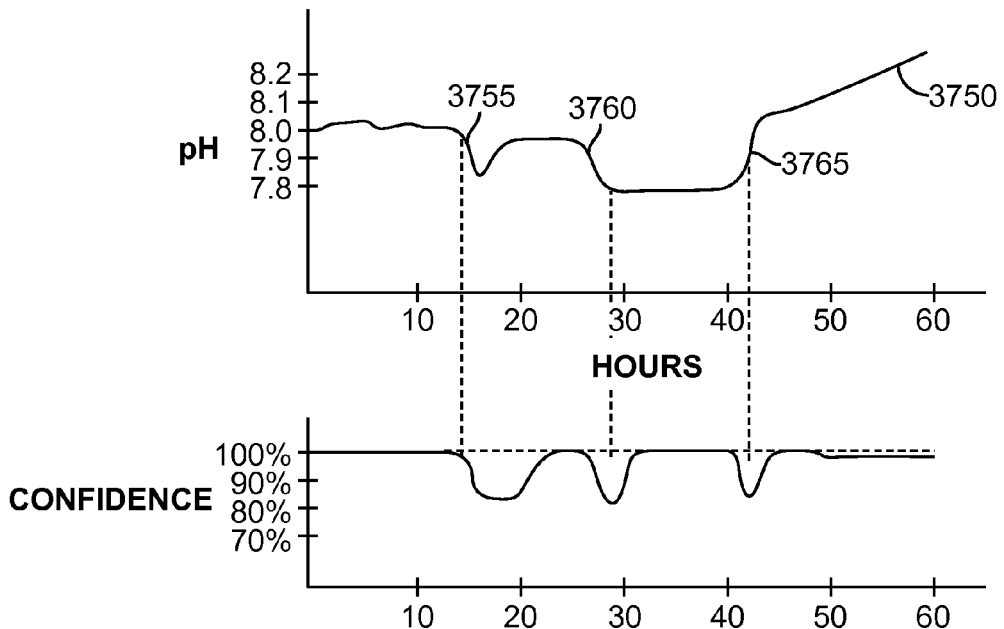
FIG. 37B illustrates another example of a confidence level plot for exemplary measured pH values.

Confidence levels may also be influenced by measured data that changes rapidly over time. A rapid change surrounded by steady data values can be indicative of a sudden change in environment, such as may be caused by a contaminant or other error condition in the monitoring system. FIG. 37B illustrates another example of plotted confidence values. In this example, pH values each measured at one location on a chemical indicator (or alternatively an average of multiple measurements) at each iteration in time is plotted 3750 over a time of approximately 60 minutes. In this example, confidence levels (in the lower plot) are shown to decrease when the pH data has a rapid rate of change over time, such as at locations 3755, 3760, and 3765.

Exemplary Enhancing Features and Alternatives

This section presents various features that can enhance any of the systems and/or components thereof, as well as alternatives to various parts of one or more of those systems and components. It is noted that each of the features and alternatives described herein need not necessarily be implemented in conjunction with any particular system or component of the present disclosure, but rather can be implemented separately so as to include only the necessary supporting features and elements.

Linear Combined I/LC and Line Camera

Figure 38:
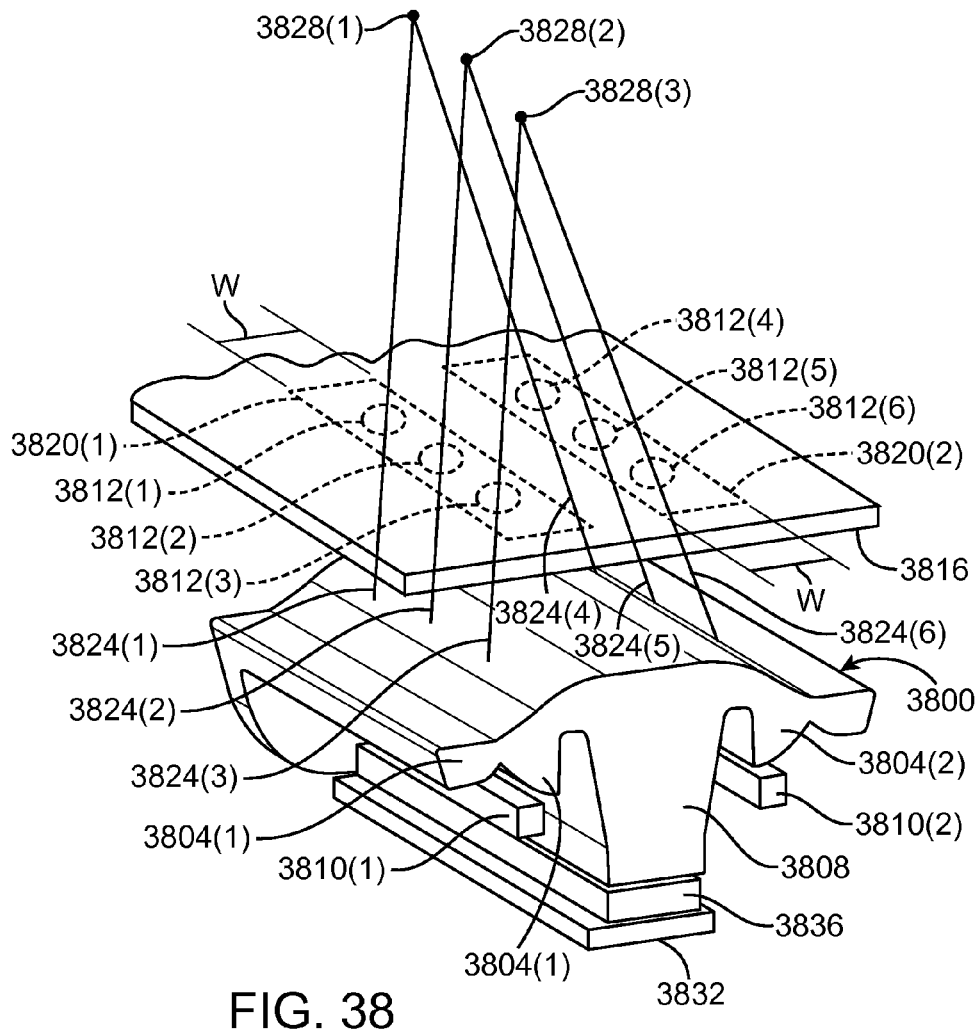
FIG. 38 is an isometric view of an exemplary linear combined I/LC that can be used in an optical reader.

FIGS. 16 and 18 illustrate combined I/LCs 1600 and 1800, respectively, that are generally circular in form. FIG. 38, however, illustrates a combined I/LC 3800 that utilizes the same components as combined I/LCs 1600 and 1800, but uses them in a linear form. As seen in FIG. 38, combined I/LC 3800 includes two linear spot lensings 3804(1) and (2) and a central linear light collector 3808 located between the two spot lensings. Depending on the number and configuration of the light sources (here, linear light sources 3810(1) and 3810(2)) used, each spot lensing 3804(1) and 3804(2) can be used to form a plurality of discrete spots 3812(1) to 3812(6) of light on a suitable target 3816 (such as a chemical indicator having a length that is equal to or greater than the length of combined I/LC 3800) or a continuous line-shaped "spot" 3820(1) and 3820(2) of light along the length of that spot lensing. In the case of individual discrete spots, the size and location of spots 3812(1) to 3812(6) can be carefully controlled by selecting the proper target distance between combined I/LC 3800 and target 3816 and carefully designing the optics of each of spot lensing 3804(1) and 3804(2) so that the discrete beams 3824(1) to 3824(6) of light converge at the proper focal points 3828(1) to 3828(3), as described above relative to FIG. 16. In the case of elongated light sources that provide line-spots 3820(1) and 3820(2), the width, W, of each of the lines can be carefully controlled in the same manner. Central light collector 3808 can be designed using the same principles described above relative to central light pipe 1644 of FIG. 16 so that the light collected from spots 3812(1) to 3812(6) or 3820(1) and 3820(2) is maximized and conducted to one or more light sensors, here, a single line camera 3832, with or without one or more intervening light filters 3836, as needed.

In one example, the light source(s) corresponding to spot lensing 3804(1) can be of one wavelength and the light source(s) corresponding to spot lensing 3804(2) can be of another wavelength. This would allow for the use of a ratio or reference wavelength, as discussed above in the context of reference illumination relative to FIG. 25, to assist in the calibration of readings taken by line camera 3832 or other sensor(s) that may be used. Use of linear camera 3832, such as a linear charge-coupled device (CCD), can enable fine resolution in the process of scanning the surface of target 3816 such that small imperfections and contaminations of the target (e.g., chemical indicator) can be identified and isolated during the data analysis process. A linear combined I/LC, such as combined I/LC 3800 of FIG. 38 can also help a cleaning element, such as a bristled element, be more effective since the bristles will all be hitting a surface that is at the same height at the same time and, therefore, will have more uniform forces along the bristles as they glide over top of the light pipe. It is noted that the linear elongated shape of combined I/LC 3800 is merely illustrative and that other elongated shapes, such as laterally curved, wavy, zig-zag, and ring-shaped, among many others, are possible.

Apparatus for Ambient Light Analysis

FIG. 10 illustrates a chemical indicator disc (FF16) that fits, for example, monitoring unit 812 of FIGS. 8 and 9. As described above, disc 816 of FIG. 10 includes ten chemical indicator patches 1004(1) to 1004(10) for taking readings indicative of various levels of parameters of the water in which the disc is submerged during use, such as water 804 of FIG. 8. In some applications, such as aquarium monitoring, it is desirable to know the quality of the light(s) being used with the aquarium. Light sources can degrade over time, resulting in decreased light quality over time. An optically based chemical indicator monitoring/measuring system/unit of the present disclosure can readily be adapted to take readings of the ambient light in the particular aquatic environment at issue.

In one embodiment using monitoring unit 812 of FIGS. 8 and 9 as an example, when ambient light readings are desired, a user can temporarily replace chemical indicator disc 816 with a similar disc, but which has various translucent color filters in place of various ones of chemical indicator patches 1004(1) to 1004(10). Each color filter, which could be a gel-type filter, among others, would permit a different set of wavelengths of the ambient light to pass through. In this manner, one or more optical readers aboard monitoring unit 812, such as reader system 400 of FIG. 4, can be used to take intensity readings of the filtered light passing through one or more of the translucent color filters. Monitoring unit 812 could then use the information about the ambient light collected using all of the color filters to analyze the spectral makeup and brightness of the ambient light. A purpose of making these spectral and brightness analyses is to ensure that coral and/or plants in the aquatic environment have optimum light conditions for photosynthesis. This special ambient light analysis disc could be used, for example, every month or so to check the quality of the light being used. Replacing each of patches 1004(1) to 1004(10) of FIG. 10 with a unique color filter relative to the other filters provided on the disc would provide ten different light filters. This will typically be enough to perform a good spectral analysis. However, if more filters are needed, any of a number of modifications could be made, such as splitting each patch location into two or more different color filters.

Stationary Magnetic Element Disc Drive

Figure 39:
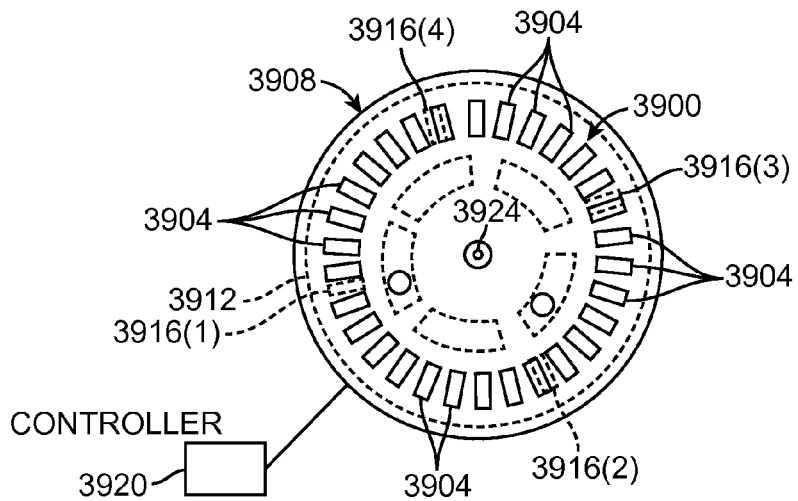
FIG. 39 is an elevational view of a water quality monitor having a stationary magnetic drive for driving a chemical indicator disc.

FIG. 39 illustrates a stationary-magnet-element disc drive 3900 that can be used in a rotary-type monitoring/measuring system/unit of the present disclosure, such as in the place of the stepper motor arrangement illustrated in FIG. 22. Referring to FIG. 39, disc drive 3900 includes a plurality of magnetically switchable magnet elements 3904 (only a handful labeled for convenience (e.g., electromagnets, rotatable magnets, magnets having movable magnetic shields, etc.) that are individually switchable to change polarity, to change the location of the poles, and/or to change the magnetic state (e.g., from non-polarized to polarized). Each magnetic element 3904 is located at a fixed location (i.e., stationary (note that the magnetic element could be moveable in place in some embodiments) on a monitoring/measuring unit 3908 and is capable of magnetically coupling with a disc 3912, such as a chemical indicator disc or an ambient light analysis disc, that includes one or more corresponding magnets, here magnets 3916(1) to 3916(4). As those skilled in the art can readily appreciate, monitoring unit 3908 can include a suitable controller 3920 that is configured, for example, via software and/or hardware, to control the states of magnetic elements 3904 so that their interaction with magnets 3916(1) to 3916(4) causes disc 3912 to rotate about its central rotational axis 3924. The number and arrangement of the magnetic elements, as well as the switching scheme implemented, can be varied to achieve the desired number of steps in a full revolution of disc 3912. In one example, the arrangement and controlling of the magnetic elements could be executed to create the small incremental steps described above in connection with the multi-reading scheme of FIG. 25.

Cylindrical Chemical Indicator Apparatus and Monitoring/Measuring Therefor

Figure 40:
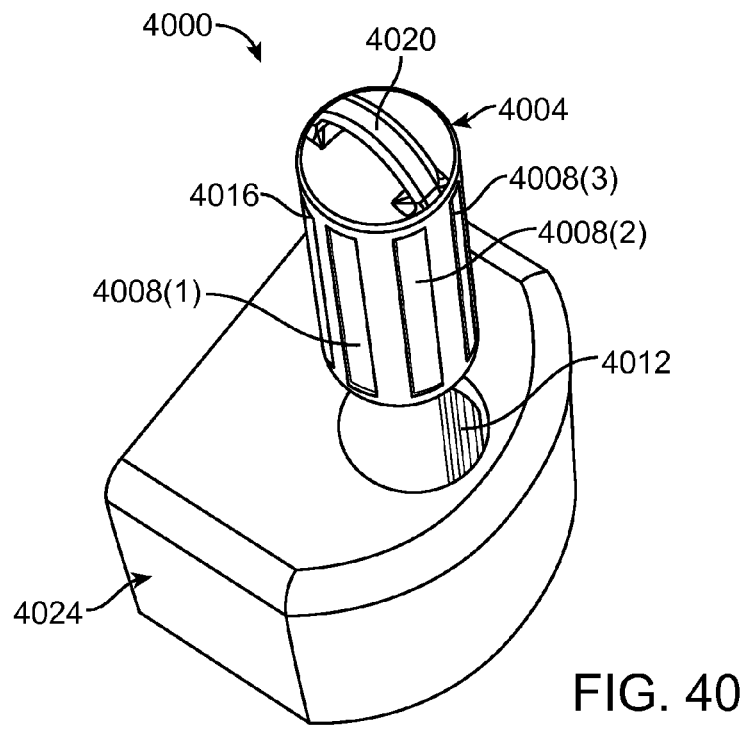
FIG. 40 is a partially exploded view of a water quality monitoring system having a cylindrical chemical indicator apparatus.

FIG. 40 illustrates a monitoring/measuring system 4000 that includes a chemical indicator apparatus that is in the form of a chemical indicator cylinder 4004. Cylinder 4004 has a plurality of longitudinal chemical indicators, of which 4008(1) to 4008(3) are visible in FIG. 40. Each of these indicators can be any one of the chemical indicator types described above, or other type that will be known to those skilled in the art. In this embodiment, chemical indicators 4008(1) to 4008(3) are optically readable, for example, in any of the manners noted above, and they are read using a reader (not shown) having a linear combined I/LC 4012. As those skilled in the art will readily appreciate, combined I/LC 4012 can be similar to linear combined I/LC 3800 of FIG. 38, including having all of the appurtenances described in connection therewith, such as line camera 3832, filter(s) 3836 and other features. In this example, cylinder 4004 of FIG. 40 includes a holder 4016 that supports the chemical indicators. For convenience, a handle 4020 is attached to holder 4016 to allow a user to readily handle cylinder 4004, especially during insertion and removal of the cylinder from a corresponding monitoring/measuring unit 4024. Although not shown, monitoring/measuring unit 4024 can include any one or more of the features described above with respect to other monitoring/measuring units, including unit 2202 of FIG. 22 and unit 2300 of FIG. 23, among others. In addition, cylinder 4004 can include any one or more of the features described above relative to other chemical indicator apparatuses, including, for example, flow promoting features (passages, fins, etc.) for promoting the flow of water around the chemical indicators, one or more cleaning elements for cleaning combined I/LC 4012, and replaceable elements for replacing individual ones or groups of the chemical indicators, among others. In addition, monitoring/measuring system 4000 can be used in any of the automated dosing, assisted dosing, monitoring, and measuring systems described herein.

Chemical Indicator Apparatuses Having Replaceable Elements

Each of the chemical indicator apparatuses shown in the drawings up to this point of the disclosure suggest that the chemical indicators on each of those apparatuses are fixed. Thus, even if only one or fewer than all of the chemical indicators on a particular apparatus have aged to the point that they should no longer be used, a user's only option to restore reading accuracy and reliability to overcome this aging is to replace the entire apparatus. However, in some cases it would be desirable to have chemical indicator apparatuses wherein the chemical indicators can be individually replaced and/or replaced in groups for any of a variety of reasons. In addition to being able to use slower-aging chemical indicators for longer periods of time before replacement, providing chemical indicator apparatuses with replaceable chemical indicators allows, for example, for the replacement of damaged indicators (such as an indicator that is accidentally scratched while being handled) and for modifying a particular apparatus for reading a different set of water parameters than the apparatus was previously set up for.

Figure 41:
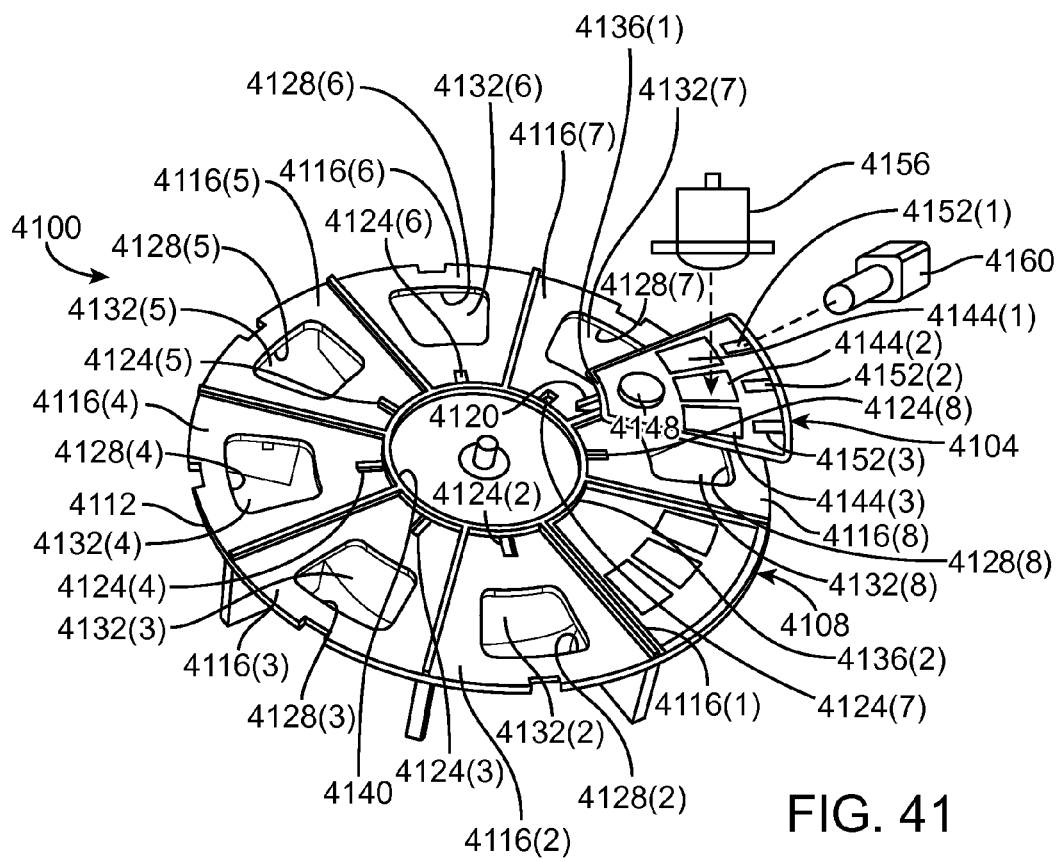
FIG. 41 is a partial schematic/partial isometric view diagram illustrating a rotary chemical indicator apparatus having replaceable chemical indicator elements.

FIG. 41 illustrates a chemical indicator apparatus 4100 having individually replaceable elements, two of which being illustrated in FIG. 41 as disengaged element 4104 and engaged element 4108. Apparatus 4100 includes a holder 4112 that, in this example, is configured to receive up to eight individually replaceable elements in sectorized receivers 4116(1) to 4116(8). In the embodiment shown, each element, such as elements 4104 and 4108, is removably engaged with holder 4112 via a tab 4120 that engages, in this example, a corresponding one of eight like slots 4124(2) to 4124(8) so as to form an interference fit when the element is fully engaged with the holder, as is illustrated by element 4108. Though not shown, each element is secured in place by a snap-lock latch tab on its underside (i.e., the side that faces the holder when properly engaged). In this example, the latch tab forms an interference fit with an edge 4128(2) to 4128(8) of a corresponding opening 4132(2) to 4132(8) and urges the radially inward end 4136(1) and 4136(2) into engagement with, in this case, a circular stop 4140 on holder.

In the example shown, element 4104 includes three chemical indicators 4144(1) to 4144(3) that can be of the same type or of differing types. Depending on the motivation for elementizing chemical indicator apparatus 4100 (e.g., for differing aging characteristics, adaption for differing water chemistries, etc.), the grouping of chemical indicators 4144(1) to 4144(3) can be selected accordingly. It is noted that while three chemical indicators 4144(1) to 4144(3) are shown, each element, including element 4104, can have more or fewer chemical indicators and also/alternatively have one or more other features, such as one or more cleaning elements, one or more optical filters, one or more information containing devices, such as RFID tag 4148, one or more indexing markings, such as optical markings 4152(1) to 4152(3), etc. In this example, at least chemical indicator 4144(2) is read by a corresponding optical reader 4156, which can be any suitable optical measuring reader, such as any one of the optical readers described above. Optical indexing markings 4152(1) to 4152(3) are read by a corresponding optical indexing reader 4160. Of course, other replaceable elements need not include any of these additional features, depending on the application at issue. Of course, chemical indicator apparatus 4100 is merely illustrative of the many apparatuses that can be composed in an elementized fashion.

Figure 42:
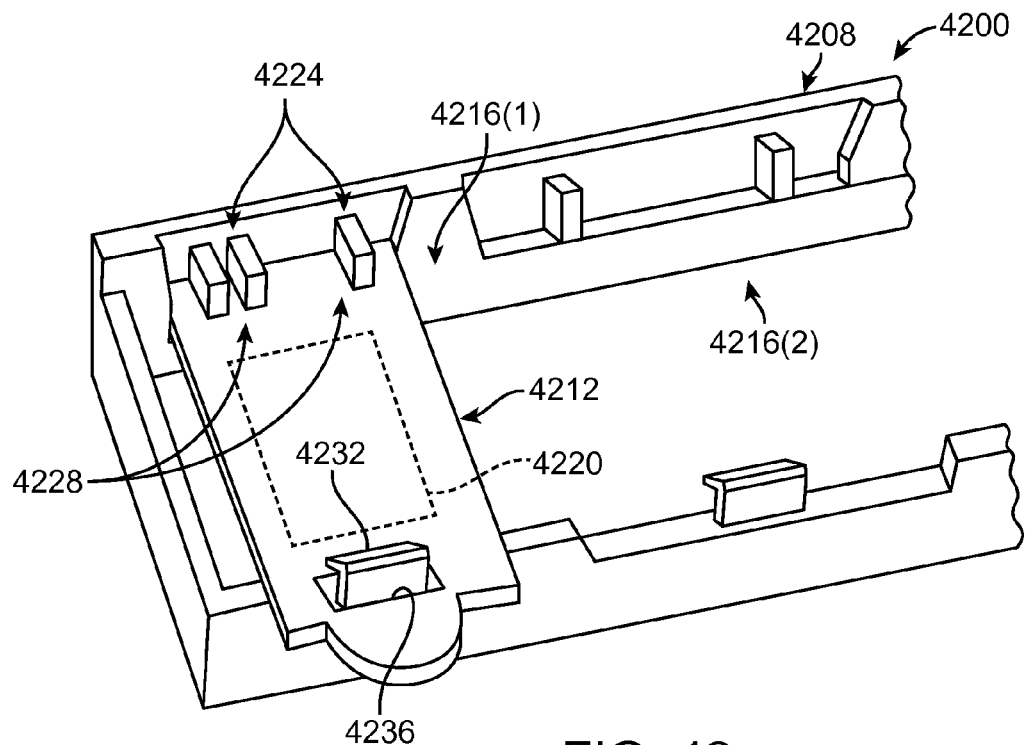
FIG. 42 is a partial isometric view of a linear chemical indicator apparatus having replaceable keyed chemical indicator elements.

FIG. 42 illustrates a generally rectangular chemical indicator apparatus 4200 that includes a holder 4208 and one individually replaceable element 4212 engageable with a corresponding receiver 4216(1). As with the replaceable elements of apparatus 4100 of FIG. 41, each replaceable element (of which only one 4212 is shown) can have any number of chemical indicators and/or other features, such as the other features described above with respect to FIG. 41. In this example, though, element 4212 contains only a single chemical indicator 4220. In this example, receiver 4216(1) is uniquely keyed with key features 4224 designed and configured to receive only a complementarily keyed replaceable element, such as element 4212, having complementary key features 4228. In systems wherein the type of chemical indicator being read can only be determined by position, keying, for example via key features 4224 and 4228 shown, can be a way of ensuring that the proper chemical indicator is in the proper position. It is noted that the same or similar keying system can be used on a wide variety of chemical indicator apparatuses having replaceable elements, including chemical indicator apparatus 4100 of FIG. 41. In the embodiment shown, element 4212 is held in position via a latch 4232 that engages a corresponding slot 4236 in the element. Other holding devices can be used in other embodiments.

In the view of FIG. 42, holder includes a second receiver 4216(2) for receiving a replaceable chemical indicator element (not shown) that is larger than element 4212 shown. The different size can be due to any one or more of a number of reasons, including enabling easy replacement of a group of chemical indicators having roughly the same aging characteristics, easy switching of a group of chemical indicators for one set of monitoring scenario for another monitoring scenario (e.g., fresh water to saltwater), and enabling easy replacement of a chemical indicator that needs to be larger than other chemical indicators, such as chemical indicator 4220, among others.

Control of Flora and/or Fauna Growth Rates

Figure 43:
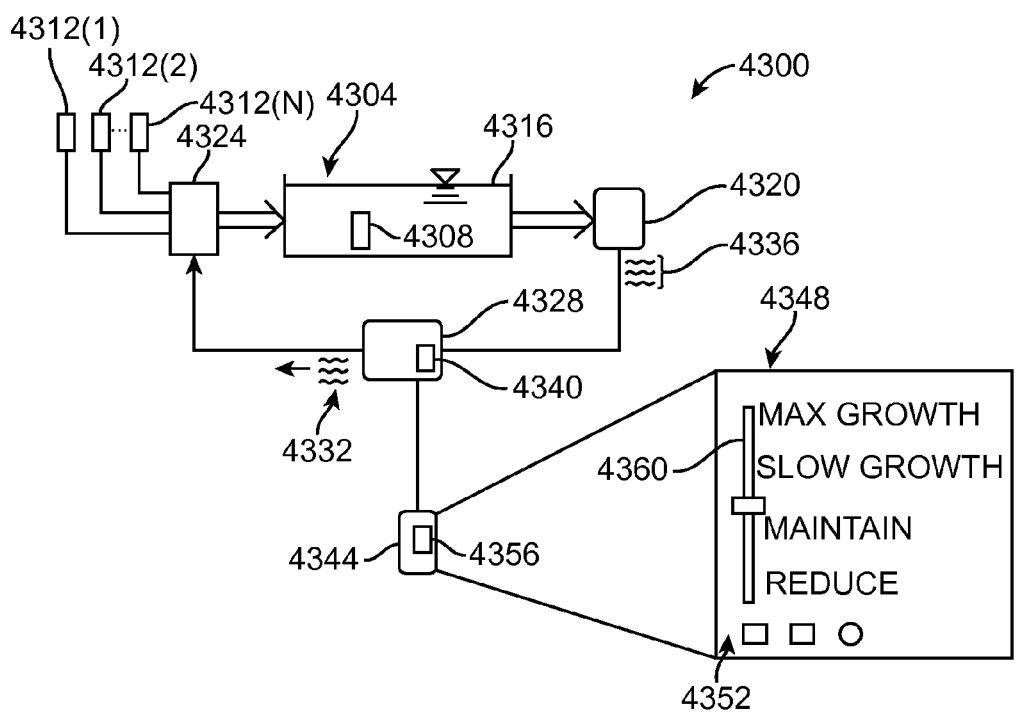
FIG. 43 is a schematic/block diagram of a coral aquarium setup having an automated dosing system that can control the growth rate of coral.

FIG. 43 illustrates a setup 4300 that includes an aquatic environment 4304 that supports one or more aquatic life forms 4308, the growth of which is/are controllable by controlling the amounts of one or more additives 4312(1) to 4312(N) added to the water 4316 in the aquatic environment. For example, if life form 4308 is coral, the growth rate of the coral can be controlled by controlling, for example, the amount of calcium added to water 4316. As another example, if life form 4308 is a particular type of plant that has a growth rate dependent on the amount of carbon dioxide present in water 4316, the amount of light, and/or the amount of fertilizer, then the growth rate of the plant can be controlled by controlling the amount of carbon dioxide and/or fertilizer added to the water and/or the amount of light provided to aquatic environment 4304.

In this example, setup 4300 includes a monitoring system 4320, which can be any one of the monitoring systems described herein or similar system utilizing one or more of the disclosed features. Setup also includes an auto-doser 4324 and a dosing calculator 4328 that generates dosing instructions 4332 based on water-quality measurements 4336 acquired via monitoring system 4320 and programmed-in parameters 4340 specific to aquatic environment 4304, such as water type, fish species, water volume, coral species, plant species, etc. In operative communication with dosing calculator 4328 is a growth controller 4344, which in this example allows user to select the amount of growth that the user would like the coral (life form 4308) to experience. As those skilled in the art will readily understand, the growth rate of coral is affected by calcium and alkalinity relative to the saturation limit of water 4316. If calcium and alkalinity are kept a small amount below the saturation limit, the growth rate will be the fastest. However, if the free calcium ($Ca^{2+}$) is around 400 parts per million (ppm), the "growth" will be more of maintenance of the current growth rate. If the free calcium goes below about 400 ppm, for example, then the coral (life form 4308) "growth" will be negative, i.e., the amount of coral will shrink. Growth controller 4344 allows the user to select the rate of coral growth desired and then modifies the dosing calculations that dosing calculator 4328 performs for the relevant parameter and additives. For example, if the user selects a fast growth rate, growth controller 4344 would cause dosing calculator 4328 to base its dosing calculations for calcium and alkalinity so that they remain close to the saturation point. In contrast, if the user selects a low or negative growth rate, growth controller 4344 would cause dosing calculator 4328 to base its relevant calculations on keeping the free calcium around or below 400 ppm.

To assist a user in setting a desired growth rate, growth controller 4344 may include a suitable UI 4348 that includes one or more controls 4352 that allow the user to select a desired coral growth rate. The one or more controls 4352 can take any of a wide variety of forms. For example, when UI 4348 is a GUI implemented in software, such as mobile computing device app 4356, the one or more controls 4352 can be one or more soft controls, such as a slider 4360 that can be positioned adjacent the desired one of "Reduce", "Maintain", "Slow Growth", and "Maximum Growth". Alternatively, for example, slider 4360 can be replaced by a set of soft radio buttons (not shown) or a soft dial, among other things. If UI 4348 is hardware based, the one or more controls 4352 could be hard controls, such as a physical slider, physical radio buttons, physical dial, etc. As mentioned above, similar features can be implements for plants and/or any other life forms the growth of which can be regulated via controlling the dosing of one or more additives 4312(1) to 4312(N) added to the water 4316 and/or the amount of light provided to aquatic environment 4304.

Social Networking and Targeted Marketing

As described above, some embodiments of the various systems of this disclosure are utilized in a cloud-computing environment. A cloud-computing environment can allow for providing software-based services to multiple subscribers to the services. In the context of the present disclosure, a cloud-computing implementation of water-quality monitoring systems can be configured to allow multiple subscribers, each with one or more water-quality monitoring systems, to become linked with one another, for example, via a social-networking platform. For example and in the context of aquariums, cloud-computing software for providing social networking and/or related services can be configured to receive information about each subscriber's aquarium setup(s), including, but not limited to, any one or more of the following: tank size; water type; fish species; coral species; plant species; dosing additives, and type(s) of tank-support equipment, such as equipment for lighting, heating, filtering, pumping, dosing, etc. In addition, the cloud-computing software can also be configured to receive information from the subscribers' water quality monitoring systems, including, but not limited to, any one or more of the following: aquarium conditions, such as chemical levels, temperature, light readings, pumping status; alarms and/or notifications, such as alarms and/or notifications for out-of-tolerance water-quality conditions, monitoring systems errors and/or confidence levels (e.g., for chemical indicator photo-aging, chemical indicator water aging, indicator wheel friction, optics fouling, etc.; and dosing instructions, among others.

Using the forgoing and/or other information known to the cloud-computing software for multiple subscribers, the software can be configured to provide the subscribers with any one or more of a variety of useful functionalities. For example, the software may automatically group subscribers into one or more social groups based on any one or more pieces of information that the software knows, such as any one or more of the pieces of information known about the subscribers' setup and/or any one or more of the pieces of information known from the subscribers' monitoring systems. As examples of automated grouping, the software may automatedly assign subscribers to the one or more relevant groups or automatedly notify subscribers of the relevant group(s) they may want to join. Examples of social groups include groups based on water type (e.g., brackish, saltwater, freshwater), groups based on species (e.g., coral, fish, plants, etc.), groups based on problems with setup (e.g., problems with maintaining calcium levels, problems with maintaining pH levels, problems with excess algae growth, problems with their monitoring systems, etc.) among many others. With such social grouping, subscribers that share one or more commonalities relating to their aquarium setups can also share their problems and their resolutions to those problems, share their dosing regimes, as well as other information, such as sharing photos, videos, and stories concerning their setups with others that may be interested because of the shared commonalities. In addition, when a subscriber to the cloud computing software wishes to chat with other subscribers of the online aquarium community, the software can be configured to automatically permit sharing of data, trends, fish species, etc., to enable other subscribers to understand the setup, problems, and/or successes of other users. In essence, such cloud-computing software marries physical data collection and diagnostics to social networking.

Regarding targeted marketing, any networked implementation of a monitoring system of the present disclosure can include a targeted-marketing feature that sends relevant advertising to a subscriber as a function of information known about that subscriber's system, such as any one or more of the pieces of information noted above relative to the social networking features. In one example, if a problem or alert condition happens and a subscriber receives a notification via a smartphone or other method, they can also be target marketed for a solution to the issue they have. For instance, if the subscriber's carbonate hardness is too low, the cloud application can suggest commercial additives that might correct their water issues. The manufacturers of these additives can bid on marketing space for specific product suggestions to end users of the system.

Exemplary Installations

As mentioned above, a monitoring/measuring system/unit of the present disclosure can be used in a wide variety of applications. Following are some exemplary installations of monitoring/measuring systems/units to illustrate the variety of differing applications and number of ways the various components of such systems/units can be configured to suit a particular application. Of course, the following installations are merely illustrative and, therefore, should not be taken as limiting the number and type of installation and system/unit configurations.

Plumbed-In System

Figure 44:
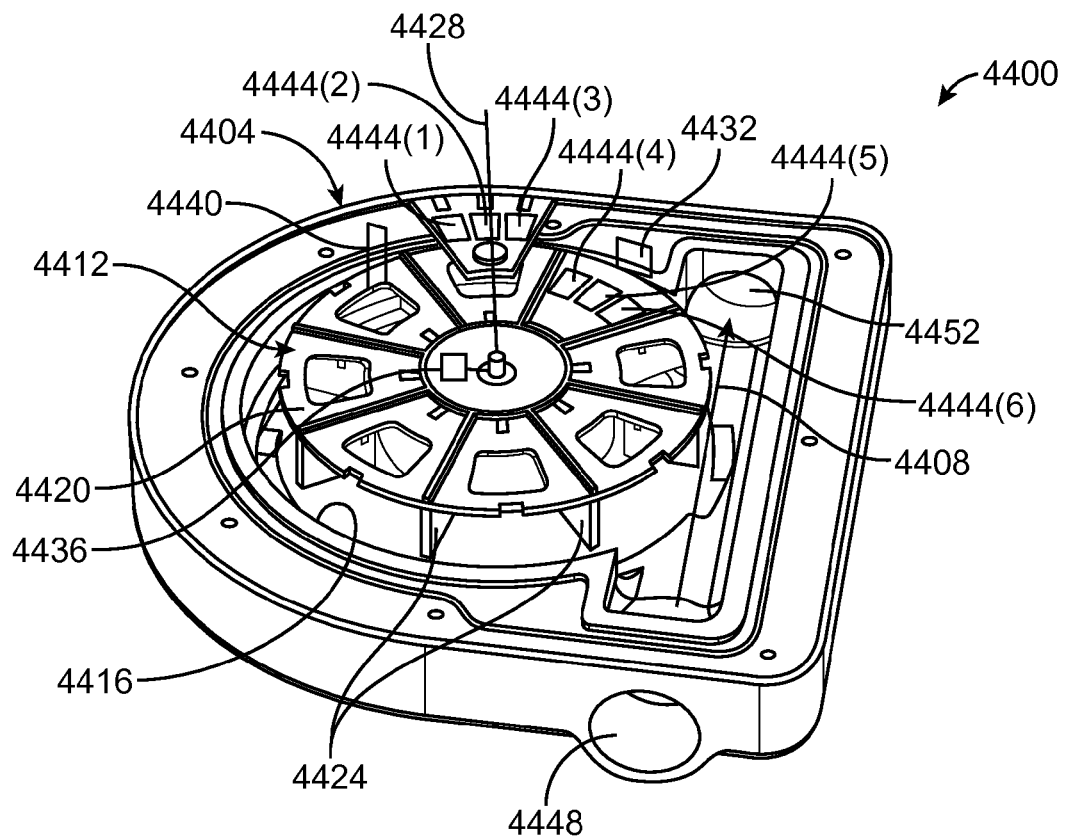
FIG. 44 is an isometric view of part of a water quality monitoring system designed and configured to be installed in plumbing.

FIG. 44 illustrates a monitoring system 4400 integrated into a watertight unit 4404 that can be inserted into plumbing (not shown) that is used to circulate water (illustrated by arrow 4408) within an aquatic environment (not shown, but could be, for example, any of the aquatic environments shown or mentioned herein). Monitoring system 4400 includes a chemical indicator apparatus 4412 that, when unit 4404 is closed, is free to rotate within a water chamber 4416 within the unit under the influence of water 4408 flowing through the unit. In this example, the flow of water 4408 provides the motive force that rotates apparatus 4412 during use for monitoring. In this connection, apparatus 4412 includes a holder 4420 that has a plurality of paddles 4424 that water 4408 strikes as it moves through unit 4404 so as to cause the holder to rotate about rotational axis 4428. While some embodiments can be designed carefully in conjunction with the flow of water 4408 so that the rotation of apparatus 4412 is suitable for readings to be taken, other embodiments may optionally include one or more speed/position control devices 4432, such as a caliper brake, an escapement mechanism, etc., that ensure that the proper speed and/or reading locations are utilized. As another alternative, monitoring system 4400 may also or alternatively include a speed sensing system 4436 that senses the rotational speed of apparatus and adjusts the acquisition of readings accordingly. Such a speed sensing system 4436 may include a rotary sensor system (not shown) or an indexed sensing system (e.g., optical, magnetic, etc.), among many others Like other monitoring systems/units described herein, monitoring system 4400 includes one or more optical readers 4440 for taking one or more readings of each of the chemical indicators, here six chemical indicators 4444(1) to 4444(6) are shown. In this example, unit 4404 includes single water inlet 4448 and a single water outlet 4452, though other embodiments can contain more of either or both. The rotation of chemical indicator apparatus 4412 induces sufficient circulation of water within chamber 4416. While not shown, those skilled in the art will readily appreciate that monitoring system 4400 can be deployed in any suitable environment, such as any of the wireless, wired, networked, cloud-computing, standalone, etc., environments described herein with suitable modifications that will be clear to those skilled in the art after reading this entire disclosure.

Standard Aquarium Sump Setup

Figure 45:
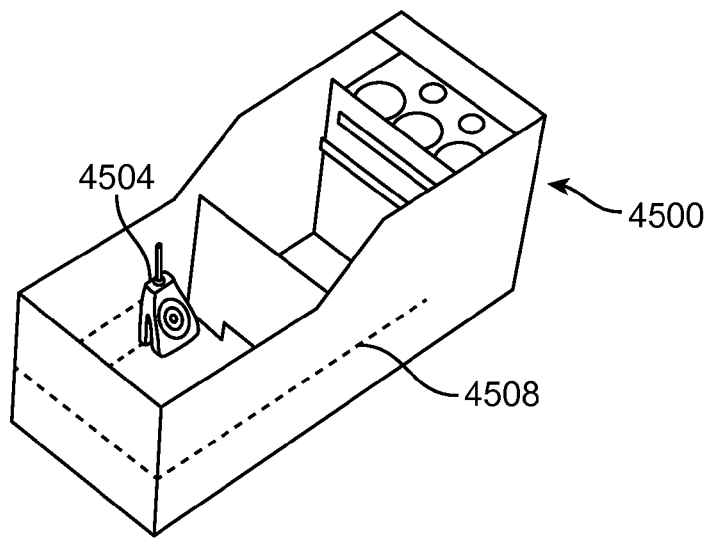
FIG. 45 is an isometric view of an aquarium sump containing a water quality monitoring system.

Various figures already described illustrate monitoring and/or dosing systems deployed in the context of aquariums. For example, FIGS. 8 and 24 describe various aquarium-centric setups in which the corresponding respective monitoring systems 812 and 2404 are submerged directly in the corresponding aquarium 808 and 2420, respectively. However, some aquarium setups, especially setups having larger aquariums, have sumps. In such cases, it can be desirable to deploy a monitoring system of the present disclosure in the sump. FIG. 45 shows an aquarium sump 4500 with a monitoring system 4504 positioned in the sump. In this example, monitoring system 4504 is the same as or similar to the monitoring system illustrated in FIG. 9 as comprising monitoring unit 812 and chemical indicator disc 816. However, it should be understood that monitoring system 4504 can be any other monitoring system described herein. That said, since the monitoring system of FIG. 9 is a partially submersible system, FIG. 45 illustrates a waterline 4508 that indicates the level of the water (not shown) that should be present in sump 4500 when monitoring system 4504 is operating. As can be seen and appreciated, waterline 4508 of FIG. 45 corresponds to waterline 920 of FIG. 9. Those skilled in the art will readily understand that aquarium sumps vary in configuration and that sump 4500 is merely illustrative and, therefore, non-limiting.

Customized Aquarium Setup

Figure 46:
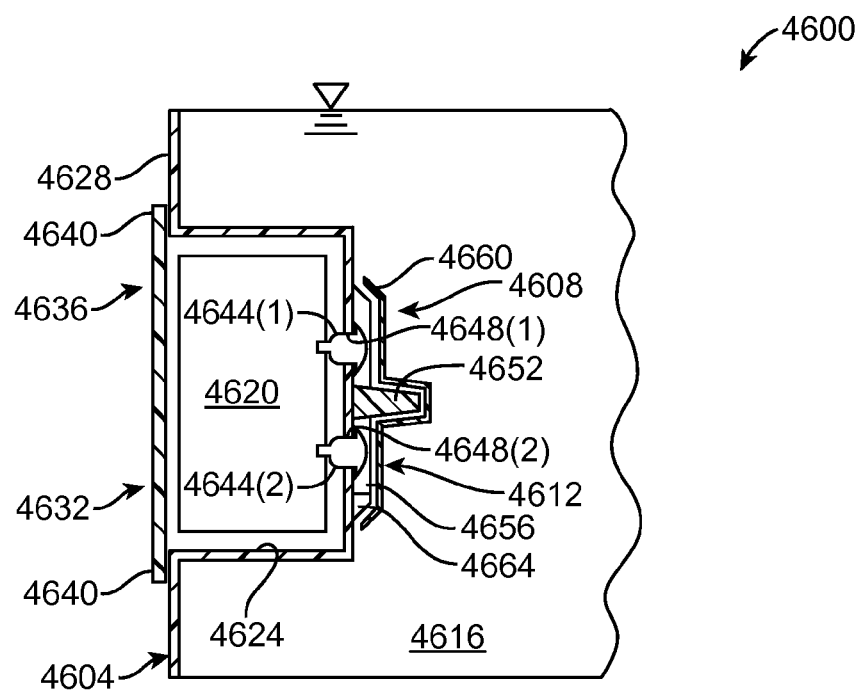
FIG. 46 is a partial cross-sectional view of a water quality monitoring system in which electrical components are located outside of the water being monitored.

FIG. 46 illustrates an aquarium setup 4600 having a tank 4604 that is "customized" to include features that enable implementing a monitoring system 4608 in which only the chemical indicator apparatus, here chemical indicator disc 4612, is submerged in the water 4616 within the tank. In this manner, all of the electronics 4620 and other components can be kept completely out of water 4616. In this example, the "custom" features include a recess 4624 formed within a wall 4628 (e.g., side wall or bottom wall) of tank 4604 that receives most or all of the components of the monitoring unit 4632 portion of monitoring system 4608. It is noted that in other embodiments, recess 4624 need not be so large (e.g., so that it does not include all or nearly all of monitoring unit 4632) or it need not be present at all, in which case monitoring unit 4632 would be on the outside of an otherwise flat wall. However, in the illustrated embodiment, with all components of monitoring unit 4632 located in recess 4624, a closure 4636 is provided to generally seal the monitoring unit in the recess. It is noted that closure 4636 can be integrated with monitoring unit 4632 such that its portions that engage wall 4628 can be flanges 4640 that can be used to secure the monitoring unit to tank 4604.

The "custom" features also include one or more combined I/LCs, here two combined I/LCs 4644(1) and 4644(2) that extend through corresponding respective openings 4648(1) and 4648(2) in wall 4628. Each combined I/LC 4644(1) and I/LC 46(2) is engaged with the corresponding opening 4648(1) and 4648(2) so that a watertight seal is created to keep water 4616 from entering recess 4624. Though not shown, other features can be provided through wall 4628, such as conductivity electrodes described elsewhere herein. It is noted that in other embodiments, the sealing member(s) can be of a different type. For example, the sealing member can be an insert (not shown) that contains combined I/LCs 4644(1) and 4644(2) and that itself is sealingly inserted into an opening in wall 4628 within recess 4624. In the example shown, chemical indicator disc 4612 is rotatably engaged with a suitable receiver 4652 that is fixedly secured to wall 4628 and is driven by a magnetic coupling, for example, like either of the magnetic couplings illustrated in FIGS. 13 and 39. In this manner, monitoring unit 4632 can be removed entirely without any leakage of water 4616 into recess 4624. To inhibit ambient light from reaching the space 4656 between disc 4612 and wall 4628, disc 4612 includes an apron 4660 and the wall of tank 4604 includes a corresponding generally annular flange 4664. Features and aspects of each of monitoring unit 4632 and disc 4612 can be the same or similar to features and aspects of other monitoring units and chemical indicator apparatuses described herein.

Hidden Aquarium Monitoring System Setup

Figure 47:
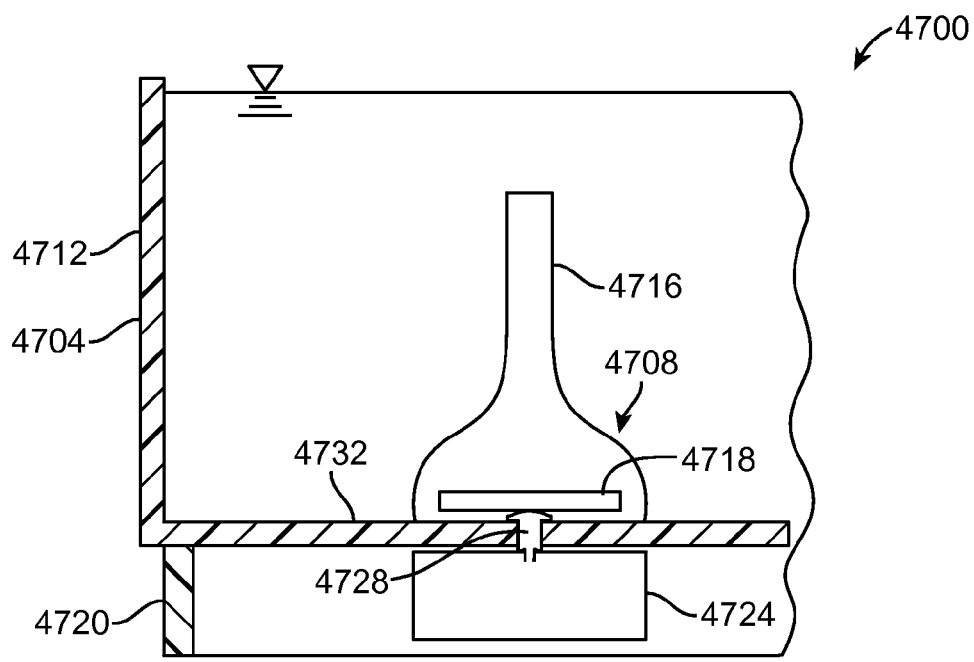
FIG. 47 is a partial cross-sectional view/partial block diagram of a water quality monitoring system concealed in an aesthetic feature inside an aquarium.

FIG. 47 illustrates an aquarium setup 4700 having an aquarium tank 4704 in which a monitoring system 4708 is hidden from view by an observer looking into the tank through at least a side wall 4712 of the tank. In this example, the concealment is due to the use of an aesthetic feature inside tank 4704, here an artificial tube coral structure 4716 that conceals a chemical indicator apparatus 4718 of monitoring system 4708 and an opaque tank stand 4720 that conceals a monitoring unit 4724 of the monitoring system. In other embodiments, a monitoring system can be concealed using one or more different types of aesthetic features within an aquarium tank and/or one or more different types of external features. In addition, it is noted that in other embodiments, an entire monitoring system, such as monitoring system 2200 of FIG. 22, can be located within tank 4704 in place of just apparatus 4718. In that case, the only part on the outside of tank 4704, here in place of monitoring unit 4724 could be the inductive power source, for example, second transformer component 2270 of FIG. 22. Returning to FIG. 47, it is noted that monitoring system 4708 can be similar to monitoring system 4608 of FIG. 46 in that it can have one or more combined I/LCs 4728 (FIG. 47) integrated with a bottom wall 4732 of tank 4704. More generally, monitoring system 4708 of FIG. 47 can be the same as or similar to any other monitoring system described herein.

Non-Aquarium Closed-Loop Systems

While the foregoing setups focus on aquarium setups, monitoring and/or dosing systems of the present disclosure can be implemented in virtually any aquatic environment having a closed-loop circulation system. For example, FIG.

48 illustrates the deployment of a monitoring system 4800 of the present disclosure in an exemplary non-aquarium closed-loop setup 4804. In this example, setup 4804 includes one or more bodies of water 4908, such as a swimming pool, hot tub, pond, fountain, etc., in which the water is treated to maintain its clarity and/or healthfulness. Setup 4804 also includes a support system 4812 that includes plumbing 4816 and equipment for maintaining water 4808. In the embodiment shown, support system 4912 includes a circulation pump 4820 and a filter system 4824. In exemplary setup 4804, monitoring system 4800 is installed in an appropriate location within support system 4812, such as in plumbing 4816. In one example, monitoring system 4800 can be configured in a manner similar to plumbed-in system 4400 of FIG. 16. However, in other embodiments, monitoring system 4800 can be located elsewhere within setup 4804 in any suitable manner, such as within a component of filter system 4824, a part of circulation pump 4820, among many other locations. In addition, monitoring system 4800 can be the same as or similar to any of the other monitoring systems described herein.

Figure 48:
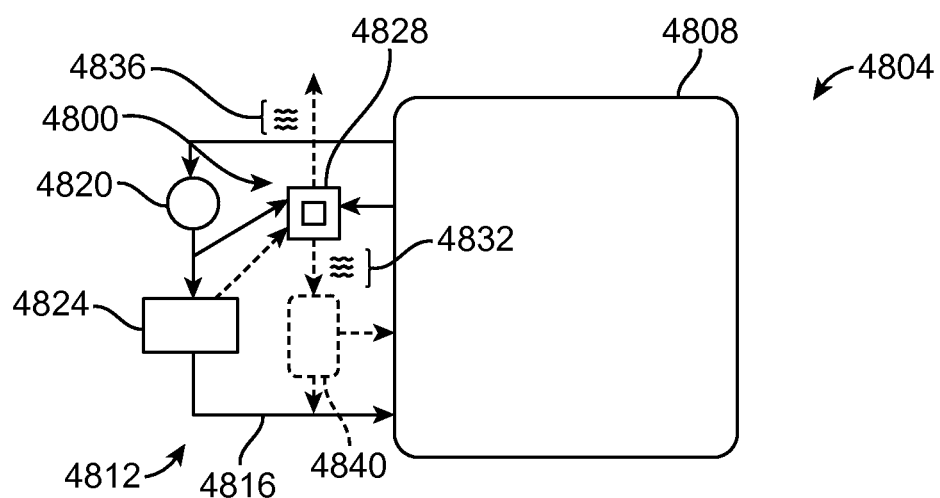
FIG. 48 is a high-level schematic diagram of a closed-loop setup having a water circulation system containing a water quality monitoring system and optional dosing system.

In the embodiment shown, closed-loop setup 4804 optionally includes a dosing calculator 4828, which depending on how additives are dosed to water 4808 when needed, can generate automated dosing instructions 4832, assisted dosing instructions 4836, or both types of instructions. In this example, setup 4804 optionally includes an automated dosing system 4840 designed and configured to add one or more additives to water 4808 according to automated dosing instructions 4832. Depending on how many additives are needed to maintain the quality of water 4808 and how many of those additives auto-dosing system 4840 can dispense, the dosing of the water can be complemented, or not, by dosing performed manually either by hand or a manually controlled doser (not shown) based on assisted dosing instructions 4836. Various examples of automated dosing and assisted dosing instructions suitable for implementation as automated dosing instructions 4832 and assisted dosing instructions 4836 are described above. In addition, various ways in which dosing calculator 4828 can function and receive the various information needed for determining and generating automated dosing instructions 4832 and/or assisted dosing instructions 4836 are described above. All of the aspects and features described above relative to dosing calculators, automated dosing instructions, and assisted dosing instructions can be applied to dosing calculator 4828, automated dosing instructions 4832, and assisted dosing instructions 4836 of FIG. 48.

Open-Loop Systems

Figure 49:
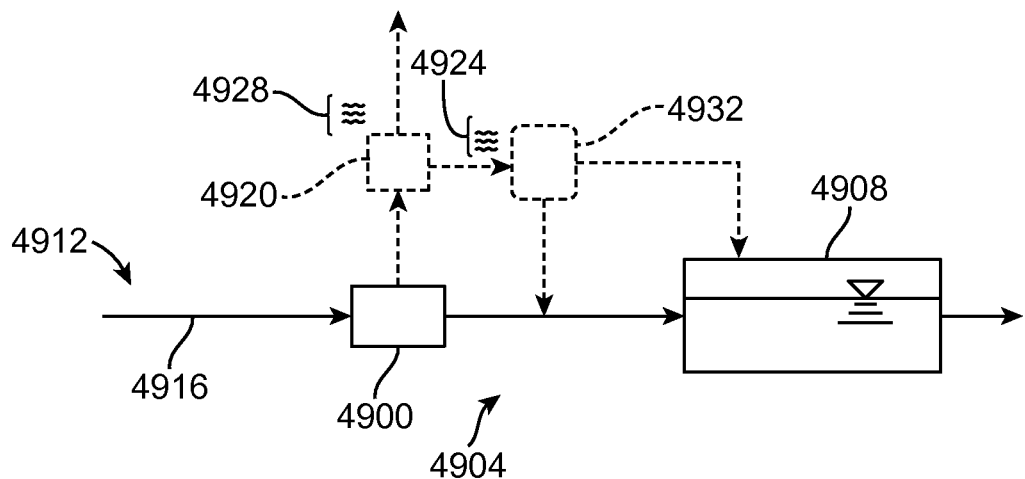
FIG. 49 is a high-level schematic diagram of an open-loop setup having a feed-water system containing a water quality measuring system and optional dosing system.

While the foregoing setups largely focus on closed-loop setups, monitoring/measuring and/or dosing systems of the present disclosure can be implemented in virtually any aquatic environment having an open-loop circulation system. For example, FIG. 49 illustrates the deployment of a monitoring system 4900 of the present disclosure in an exemplary open-loop setup 4904. In this example, setup 4904 includes monitored/measured water 4908, such as water in a domestic water distribution system, a wastewater treatment facility, an industrial processing process, etc. Setup 4904 also includes a feed-water system 4912 that includes plumbing 4916 and in some cases equipment (not shown) for processing water 4908. Examples of such equipment include but are not limited to filters, softeners, etc. In exemplary setup 4904, monitoring system 4900 is installed in an appropriate location within support system 4912, such as in plumbing 4916. In one example, monitoring system 4900 can be configured in a manner similar to plumbed-in system 4400 of FIG. 16. However, in other embodiments, monitoring system 4900 can be located elsewhere within setup 4904 in any suitable manner. In addition, monitoring system 4900 can be the same as or similar to any of the other monitoring systems described herein.

In the embodiment shown, open-loop setup 4904 optionally includes a dosing calculator 4920, which depending on how additives are dosed to water 4908 when needed, can generate automated dosing instructions 4924, assisted dosing instructions 4928, or both types of instructions. In this example, setup 4804 optionally includes an automated dosing system 4932 designed and configured to add one or more additives to water 4808 according to automated dosing instructions 4924. Depending on how many additives are needed to maintain the quality of water 4908 and how many of those additives auto-dosing system 4932 can dispense, the dosing of the water can be complemented, or not, by dosing performed manually either by hand or a manually controlled doser (not shown) based on assisted dosing instructions 4928. Various examples of automated dosing and assisted dosing instructions suitable for implementation as automated dosing instructions 4924 and assisted dosing instructions 4928 are described above. In addition, various ways in which dosing calculator 4920 can function and receive the various information needed for determining and generating automated dosing instructions 4924 and/or assisted dosing instructions 4928 are described above. All of the aspects and features described above relative to dosing calculators, automated dosing instructions, and assisted dosing instructions can be applied to dosing calculator 4920, automated dosing instructions 4924, and assisted dosing instructions 4928 of FIG. 49.

It is to be noted that the aspects and embodiments described herein may be conveniently implemented using one or more machines (e.g., one or more computing devices/computer systems that are part of an aquatic environment monitoring and/or dosing system) including hardware and special programming according to the teachings of the present specification, as will be apparent to those of ordinary skill in the computer art. Appropriate software coding can readily be prepared by skilled programmers based on the teachings of the present disclosure, as will be apparent to those of ordinary skill in the software art.

Such software may be a computer program product that employs a machine-readable hardware storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable hardware storage medium include, but are not limited to, a magnetic disk (e.g., a conventional floppy disk, a hard drive disk), an optical disk (e.g., a compact disk "CD", such as a readable, writeable, and/or re-writable CD; a digital video disk "DVD", such as a readable, writeable, and/or rewritable DVD), a magneto-optical disk, a read-only memory "ROM" device, a random access memory "RAM" device, a magnetic card, an optical card, a solid-state memory device (e.g., a flash memory), an EPROM, an EEPROM, and any combinations thereof. A machine-readable medium, as used herein, is intended to include a single medium as well as a collection of physically separate media, such as, for example, a collection of compact disks or one or more hard disk drives in combination with a computer memory. As used herein, a machine-readable storage medium does not include a signal.

Such software may also include information (e.g., data) carried as a data signal on a data carrier, such as a carrier wave. Such a data signal or carrier wave would not be considered a machine-readable hardware storage medium. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, a computer workstation, a terminal computer, a server computer, a handheld device (e.g., tablet computer, a personal digital assistant "PDA", a mobile telephone, etc.), a web appliance, a network router, a network switch, a network bridge, any machine capable of executing a sequence of instructions that specify an action to be taken by that machine, and any combinations thereof. In one example, a computing device may include and/or be included in, a kiosk. In another example, a dosing calculator (as discussed herein) may be associated with (e.g., be part of, be connected to, be included in, etc.) a computing device or any part thereof.

Figure 50:
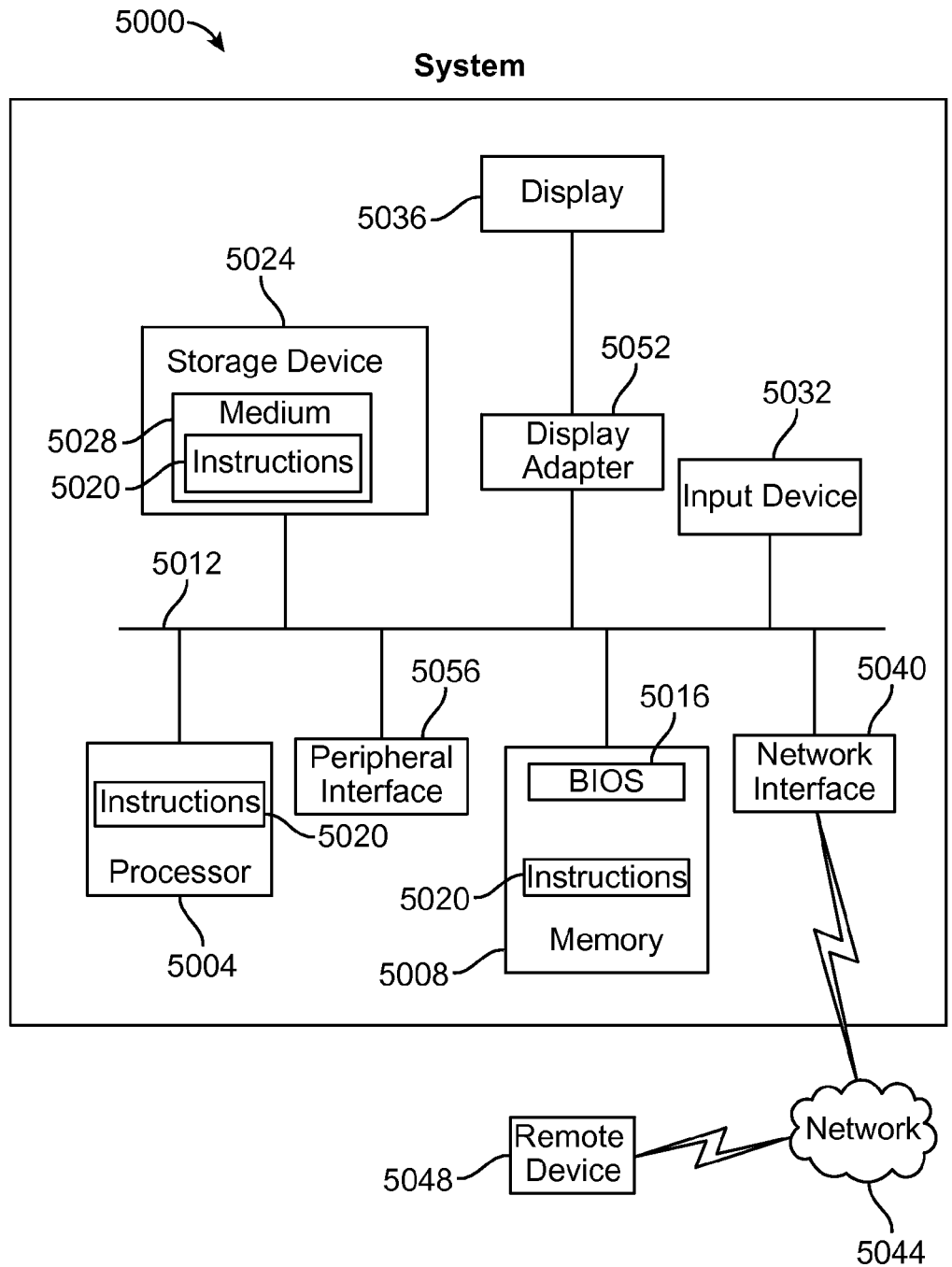
FIG. 50 is a high-level diagram of a computing system that can be used to contain and execute software instructions for implementing one or more of the functionalities described herein.

FIG. 50 shows a diagrammatic representation of one exemplary embodiment of a computing system 5000, within which a set of instructions for causing one or more processors 5004 to perform any one or more of the functionalities, aspects, and/or methodologies of the present disclosure. It is also contemplated that multiple computing systems may be utilized to implement a specially configured set of instructions for performing any one or more of the functionalities, aspects, and/or methodologies of the present disclosure in a distributed computing matter.

Computing system 5000 can also include a memory 5008 that communicates with the one or more processors 5004, and with other components, for example, via a bus 5012. Bus 5012 may include any of several types of bus structures including, but not limited to, a memory bus, a memory controller, a peripheral bus, a local bus, and any combinations thereof, using any of a variety of bus architectures.

Memory 5008 may include various components (e.g., machine-readable hardware storage media) including, but not limited to, a random access memory component (e.g., a static RAM "SRAM", a dynamic RAM "DRAM", etc.), a read only component, and any combinations thereof. In one example, a basic input/output system 5016 (BIOS), including basic routines that help to transfer information between elements within computing system 5000, such as during start-up, may be stored in memory 5008. Memory 5008 may also include (e.g., stored on one or more machine-readable hardware storage media) instructions (e.g., software) 5020 embodying any one or more of the aspects and/or methodologies of the present disclosure. In another example, memory 5008 may further include any number of program modules including, but not limited to, an operating system, one or more application programs, other program modules, program data, and any combinations thereof.

Computing system 5000 may also include a storage device 5024, such as, but not limited to, the machine readable hardware storage medium described above. Storage device 5024 may be connected to bus 5012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 5024 (or one or more components thereof) may be removably interfaced with computing system 5000 (e.g., via an external port connector (not shown)). Particularly, storage device 5024 and an associated machine-readable medium 5028 may provide nonvolatile and/or volatile storage of machine-readable instructions, data structures, program modules, and/or other data for computing system 5000. In one example, software instructions 5020 may reside, completely or partially, within machine-readable hardware storage medium 5028. In another example, software instructions 5020 may reside, completely or partially, within processors 5004.

Computing system 5000 may also include an input device 5032. In one example, a user of computing system 5000 may enter commands and/or other information into computing system 5000 via one or more input devices 5032. Examples of an input device 5032 include, but are not limited to, an alphanumeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), touch screen, and any combinations thereof. Input device(s) 5032 may be interfaced to bus 5012 via any of a variety of interfaces (not shown) including, but not limited to, a serial interface, a parallel interface, a game port, a USB interface, a FIREWIRE interface, a direct interface to bus 5012, and any combinations thereof. Input device(s) 5032 may include a touch screen interface that may be a part of or separate from display(s) 5036, discussed further below. Input device(s) 5032 may be utilized as a user selection device for selecting one or more graphical representations in a graphical interface as described above.

A user may also input commands and/or other information to computing system 5000 via storage device 5024 (e.g., a removable disk drive, a flash drive, etc.) and/or network interface device(s) 5040. A network interface device, such as any one of network interface device(s) 5040 may be utilized for connecting computing system 5000 to one or more of a variety of networks, such as network 5044, and one or more remote devices 5048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network, a telephone network, a data network associated with a telephone/voice provider, a direct connection between two computing devices, and any combinations thereof. A network, such as network 5044, may employ a wired and/or a wireless mode of communication. In general, any network topology may be used. Information (e.g., data, software instructions 5020, etc.) may be communicated to and/or from computing system 5000 via network interface device(s) 5040.

Computing system 5000 may further include one or more video display adapter 5052 for communicating a displayable image to one or more display devices, such as display device(s) 5036. Examples of a display device include, but are not limited to, a liquid crystal display (LCD), a cathode ray tube (CRT), a plasma display, a light emitting diode (LED) display, and any combinations thereof. Display adapter(s) 5052 and display device(s) 5036 may be utilized in combination with processor(s) 5004 to provide a graphical representation of a utility resource, a location of a land parcel, and/or a location of an easement to a user. In addition to a display device, computing system 5000 may include one or more other peripheral output devices including, but not limited to, an audio speaker, a printer, and any combinations thereof. Such peripheral output devices may be connected to bus 5012 via a peripheral interface 5056. Examples of a peripheral interface include, but are not limited to, a serial port, a USB connection, a FIREWIRE connection, a parallel connection, and any combinations thereof.

General Disclosure Aspects

The systems, methods, apparatuses, software, etc. of the present invention have been exemplified by various exemplary embodiments and implementations as shown in the accompanying drawings and as described above. However, it should be understood that the discrete presentation of these embodiments and implementations should not be construed as requiring that: 1) these embodiments and implementations stand in isolation from one another; 2) that individual components, features, aspects, and/or functionalities described relative to each one of the embodiments and implementations cannot be used independently of the corresponding embodiment or implementation; and 3) that individual components, features, aspects, and/or functionalities described cannot be used individually in connection with other embodiments and implementations, either described herein or derivable therefrom, alone and/or in any combination with one another. On the contrary, those skilled in the art will appreciate that the individual components, features, aspects, and functionalities of a particular embodiment or implementation can, as appropriate under the circumstances, be utilized alone and in any subcombination with other components, features, aspects, and/or functionalities of that particular embodiment or implementation and with any other embodiment or implementation, including the specific examples described herein in connection with FIGS. 1 through 50.

For example, it is noted that some implementations described above include a monitoring system, a dosing calculator, and a dosing system. However, in alternative embodiments of those implementations, only one or only two of the three components may be present. For example, some implementations may include only a monitoring system, other implementations may include only a dosing calculator, still other implementations may include only a dosing system, further implementations may include a monitoring system and a dosing calculator, still further implementations may include a dosing calculator and a dosing system, and yet still further implementations may include a monitoring system and a dosing system.

In other examples, specific components, features, aspects, and functionalities of chemical indicator apparatuses, such as shape of the holder, presence or absence of one or more cleaning elements, type of chemical indicator(s), number of indicators, presence or absence of one or more water passages, presence or absence of one or more water filters, presence or absence of one or more light filters, presence or absence of a temperature sensor, presence or absence of one or more information storage devices, presence or absence of one or more position indicators, arrangement of indicator(s), etc., can be used on any chemical indicator apparatus that fall within the scope of the present disclosure, individually, or together within one another in any suitable combination or subcombination. In addition, any resulting chemical indicator apparatus made accordingly can be used with any suitably configured monitoring system that fall within the scope of the present disclosure, such as any one of the monitoring systems specifically illustrated in the accompanying figures and/or described above.

Similarly, any one or more of the robustness features, aspects, and functionalities described above, such as multi-read fault detection, fluorescent-reading contamination compensation, ambient light compensation, chemical indicator age compensation, friction testing, dosing protection, and dosing rate protection, among others, can be used individually and in any combination with one another and/or with any other suitable components, features, aspects, and functionalities, such as the components, features, aspects, and functionalities, described herein with respect to specific embodiments and implementations of non-robustness features, aspects, and functionalities. In addition, the robustness features, aspects, and functionalities can be used with any monitoring system, measuring system, and monitor falling within the scope of the present disclosure, including the specific monitoring systems, measuring systems, and monitors described herein.

Likewise, any one or more of the components, features, aspects, and functionalities of the exemplary enhancements and alternatives described above, such as a linear combined I/LC, an ambient light analysis apparatus, a stationary-magnet magnetic drive, a cylindrical chemical indicator apparatus, individually and group-wise replaceable chemical indicator elements, and growth-rate control, among others, can be used individually and in any combination with one another and/or with any other suitable components, features, aspects, and functionalities, such as the components, features, aspects, and functionalities, described herein with respect to specific embodiments and implementations of monitoring systems, measuring systems, monitors, chemical indicator apparatuses, and dosing calculators falling within the scope of the present disclosure, including the specific monitoring systems, measuring systems, monitors, chemical indicator apparatuses, and dosing calculators described herein.

Furthermore, it is noted that all of the forgoing description of the vastness of inter-combinability, combinations, and subcombinations of the various components, features, aspects, and functionalities of embodiments and implementations that fall within the scope of the present disclosure, including the specific examples of such described herein and illustrated in FIGS. 1-44 and 50, is equally applicable to any of the specific setups described herein, including, but not limited to, standard aquarium setups, customized aquarium setups, hidden aquarium setups, non-aquarium closed-loop setups, and open-loop setups.

Exemplary embodiments have been disclosed above and illustrated in the accompanying drawings. It will be understood by those skilled in the art that various changes, omissions and additions may be made to that which is specifically disclosed herein without departing from the spirit and scope of the present invention. The following claims include dependent claims for each independent claim that are shown without multiple dependencies. It is contemplated that each of the dependent claims for a given independent claim could alternatively be multiply dependent from any one or more of the preceding claims for that independent claim.

What is claimed is:

1. A water-quality monitoring system for monitoring quality of water in an aquatic environment, comprising:
   a chemical indicator wheel designed and configured to be submerged in the water of the aquatic environment during monitoring of changes in levels of one or more constituents of the water, said chemical indicator wheel including:
      a holder having a rotational axis; and
      a plurality of chemical indicators fixedly supported by said holder, wherein said plurality of chemical indicators are designed and configured to continuously undergo optically detectable changes in response to increasing and decreasing changes over time in levels of corresponding respective differing constituents of the water; and
   a monitoring unit that includes:
      an optical reader designed and configured to acquire optical readings of each of said plurality of indicators; and a drive system designed and configured to drive said chemical indicator wheel to at least one reading position for each of said plurality of chemical indicators, wherein said optical reader can take a reading of each of said plurality of chemical indicators while the chemical indicator wheel is submerged in the water of the aquatic environment.

2. A water-quality monitoring system according to claim 1, wherein said holder is discoidal in shape.

3. A water-quality monitoring system according to claim 1, wherein each of said plurality of indicators is an immobilized-dye indicator.

4. A water-quality monitoring system according to claim 3, wherein said chemical indicator wheel includes at least four immobilized-dye indicators.

5. A water-quality monitoring system according to claim 1, wherein said optical reader includes at least one light source, at least one detector, and a combined illuminator/light collector designed and configured to, sequentially, direct light from said at least one light source to each of said plurality of chemical indicators, and to collect, sequentially, from each of said plurality of chemical indicators.

6. A water-quality monitoring system according to claim 5, wherein said optical reader includes a plurality of light sources, said combined illuminator/light collector including spot lensing designed and configured to direct light from said plurality of light sources so as to form a corresponding plurality of illumination spots, sequentially, on each of said plurality of chemical indicators.

7. A water-quality monitoring system according to claim 5, wherein said optical reader includes a light detector, said combined illuminator/light collector including a central light conductor for conducting collected light to said light detector.

8. A water-quality monitoring system according to claim 7, wherein said combined illuminator/light collector further includes dispersive lensing located adjacent to said spot lensing so as to disperse a portion of light emitted by each of said plurality of light sources away from each of said corresponding plurality of illumination spots.

9. A water-quality monitoring system according to claim 1, wherein said drive system comprises a plurality of paddles designed and configured to be driven by flow of the water.

10. A water-quality monitoring system according to claim 1, wherein said drive system includes a magnetic coupling between said chemical indicator wheel and said monitoring unit.

11. A water-quality monitoring system according to claim 10, wherein said drive system includes a stepper motor that drives a magnet holder.

12. A water-quality monitoring system according to claim 10, wherein said drive system includes a plurality of magnetic elements driven to sequentially attract a plurality of magnetic elements on said chemical indicator wheel so as to impart rotation to said chemical indicator wheel.

13. A water-quality monitoring system according to claim 1, wherein said chemical indicator wheel includes a radio-frequency identification (RFID) tag that stores calibration data for said plurality of chemical indicators, and said monitoring unit includes an RFID tag reader for reading said RFID tag.

14. A water-quality monitoring system according to claim 1, wherein said optical reader includes an optic having a surface exposed to said water, and said indicator wheel includes a cleaning element designed, configured, and located for cleaning said surface of said optic when said chemical indicator wheel is driven.

15. A water-quality monitoring unit for monitoring quality of water in an aquatic environment, wherein the monitoring unit is designed and configured to rotatably drive a chemical indicator wheel designed and configured to be submerged in the water of the aquatic environment during monitoring of changes in levels of one or more constituents in the water, the chemical indicator wheel having a rotational axis and including a plurality of chemical indicators designed and configured to undergo optically detectable changes in response to increasing and decreasing changes over time in levels of corresponding respective differing constituents of the water, the monitoring unit including:
an optical reader designed and configured to acquire optical readings of each of the plurality of indicators; and
a drive system designed and configured to drive said chemical indicator wheel to at least one reading position for each of said plurality of chemical indicators, wherein said optical reader can take a reading each of said plurality of chemical indicators while the chemical indicator wheel is submerged in the water of the aquatic environment.

16. A water-quality monitoring unit according to claim 15, wherein said optical reader includes at least one light source, at least one detector, and a combined illuminator/light collector designed and configured to, sequentially, direct light from said at least one light source to each of the plurality of chemical indicators, and to collect, sequentially, light from each of the plurality of chemical indicators.

17. A water-quality monitoring unit according to claim 16, wherein said optical reader includes a plurality of light sources, said combined illuminator/light collector including spot lensing designed and configured to direct light from said plurality of light sources so as to form a corresponding plurality of illumination spots, sequentially, on each of the plurality of chemical indicators.

18. A water-quality monitoring unit according to claim 17, wherein said optical reader includes a light detector, said combined illuminator/light collector including a central light conductor for conducting collected light to said light detector.

19. A water-quality monitoring unit according to claim 18, wherein said combined illuminator/light collector further includes dispersive lensing located adjacent to said spot lensing so as to disperse a portion of light emitted by each of said plurality of light sources away from each of said corresponding plurality of illumination spots.

20. A water-quality monitoring unit according to claim 15, wherein said drive system comprises a plurality of paddles designed and configured to be driven by flow of the water.

21. A water-quality monitoring unit according to claim 15, wherein said drive system includes a magnetic coupling between the chemical indicator wheel and the monitoring unit.

22. A water-quality monitoring unit according to claim 21, wherein said drive system includes a stepper motor that drives a magnet holder.

23. A water-quality monitoring unit according to claim 21, wherein said drive system includes a plurality of magnetic elements driven to sequentially attract a plurality of magnetic elements on the chemical indicator wheel so as to impart rotation to the chemical indicator wheel.

24. A water-quality monitoring unit according to claim 15, wherein the chemical indicator wheel includes a radio-frequency identification (RFID) tag that stores calibration data for the plurality of chemical indicators, and said monitoring unit includes an RFID tag reader for reading the RFID tag.

* * * * *